US012595264B2

(12) United States Patent
Meng et al.

(10) Patent No.: US 12,595,264 B2
(45) Date of Patent: Apr. 7, 2026

(54) HETEROCYCLIC GLP-1 AGONISTS

(71) Applicant: Gasherbrum Bio, Inc., South San Francisco, CA (US)

(72) Inventors: Qinghua Meng, Shanghai (CN); Weiqiang Xing, Shanghai (CN); Haizhen Zhang, Shanghai (CN); Xichen Lin, Shanghai (CN); Hui Lei, Shanghai (CN); Andrew Jennings, San Francisco, CA (US)

(73) Assignee: Gasherbrum Bio, Inc., South San Francisco, CA (US)

( * ) Notice: Subject to any disclaimer, the term of this patent is extended or adjusted under 35 U.S.C. 154(b) by 396 days.

(21) Appl. No.: 18/044,743

(22) PCT Filed: Sep. 8, 2021

(86) PCT No.: PCT/CN2021/117263

§ 371 (c)(1),
(2) Date: Mar. 9, 2023

(87) PCT Pub. No.: WO2022/052958

PCT Pub. Date: Mar. 17, 2022

(65) Prior Publication Data

US 2023/0331732 A1 Oct. 19, 2023

(30) Foreign Application Priority Data

Sep. 10, 2020 (WO) ................ PCT/CN2020/114319

(51) Int. Cl.

| | |
|---|---|
| ***C07D 487/04*** | (2006.01) |
| ***A61K 31/155*** | (2006.01) |
| ***A61K 31/4985*** | (2006.01) |
| ***A61K 31/675*** | (2006.01) |
| ***A61K 38/26*** | (2006.01) |
| ***C07F 9/6561*** | (2006.01) |

(52) U.S. Cl.

CPC .......... *C07D 487/04* (2013.01); *A61K 31/155* (2013.01); *A61K 31/4985* (2013.01); *A61K 31/675* (2013.01); *A61K 38/26* (2013.01); *C07F 9/6561* (2013.01); *C07B 2200/07* (2013.01)

(58) Field of Classification Search

CPC ... C07D 487/04; C07F 9/6561; A61K 31/155; A61K 31/4985; A61K 31/675; A61K 38/26; C07B 2200/07

See application file for complete search history.

(56) References Cited

U.S. PATENT DOCUMENTS

| | | | | |
|---|---|---|---|---|
| 6,927,214 | B1 | 8/2005 | Teng et al. | |
| 10,858,356 | B2 | 12/2020 | Yoshino et al. | |
| 11,492,365 | B2 | 11/2022 | Meng et al. | |
| 11,584,751 | B1 * | 2/2023 | Ren | A61P 1/16 |
| 12,037,339 | B2 * | 7/2024 | Ren | C07D 519/00 |
| 12,291,529 | B2 * | 5/2025 | Huang | C07D 519/00 |
| 2004/0009573 | A1 | 1/2004 | Strobel et al. | |
| 2007/0015812 | A1 | 1/2007 | Boehringer et al. | |
| 2009/0197863 | A1 | 8/2009 | Chu et al. | |
| 2011/0190343 | A1 | 8/2011 | Gochin et al. | |
| 2011/0306542 | A1 | 12/2011 | Boehm et al. | |
| 2015/0119412 | A1 | 4/2015 | Kasai et al. | |
| 2015/0133448 | A1 | 5/2015 | Okano et al. | |
| 2016/0141517 | A1 | 5/2016 | Yang | |
| 2018/0092908 | A1 | 4/2018 | Stockwell et al. | |
| 2019/0300526 | A1 | 10/2019 | Fan et al. | |
| 2020/0017505 | A1 | 1/2020 | Maeba et al. | |
| 2023/0174565 | A1 | 6/2023 | Meng et al. | |
| 2023/0322771 | A1 | 10/2023 | Meng et al. | |
| 2024/0360166 | A1 | 10/2024 | Chen et al. | |
| 2024/0366639 | A1 | 11/2024 | Meng et al. | |
| 2025/0042899 | A1 | 2/2025 | Allian et al. | |

FOREIGN PATENT DOCUMENTS

| | | |
|---|---|---|
| CN | 103421006 | 12/2013 |
| CN | 110325530 | 10/2019 |
| CN | 110804059 | 2/2020 |
| CN | 111217796 | 6/2020 |
| CN | 111217842 | 6/2020 |
| EP | 461079 | 12/1991 |

(Continued)

OTHER PUBLICATIONS

International Search Report and Written Opinion for PCT/CN2021/117263 dated Dec. 9, 2021, 9 pages.

Kawai et al., "Structural basis for GLP-1 receptor activation by LY3502970, an orally active nonpeptide agonist", Proceedings of the National Academy of Sciences of the United States of America (2020), 117(47), 29959-29967.

Finkbeiner et al., "Phosphine Oxides from a Medicinal Chemist's Perspective: Physicochemical and in Vitro Parameters Relevant for Drug Discovery", Journal of Medicinal Chemistry (2020), 63(13), 7081-7107.

(Continued)

*Primary Examiner* — Timothy R Rozof

(74) *Attorney, Agent, or Firm* — Sheppard Mullin Richter & Hampton LLP

(57) ABSTRACT

This disclosure relates to GLP-1 agonists of Formula (I), including pharmaceutically acceptable salts and solvates thereof, and pharmaceutical compositions including the same.

(I)

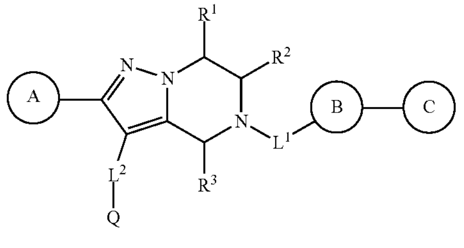

24 Claims, No Drawings

(56) References Cited

FOREIGN PATENT DOCUMENTS

| | | | |
|---|---|---|---|
| EP | 1625847 | | 2/2006 |
| EP | 3539948 | | 9/2019 |
| EP | 3539950 | | 9/2019 |
| JP | 08295646 | | 11/1996 |
| JP | 2012223714 | | 11/2012 |
| JP | 2012224760 | | 11/2012 |
| JP | 2019099571 | | 6/2019 |
| KR | 2013088577 | | 8/2013 |
| WO | WO-95/01961 | | 1/1995 |
| WO | WO-97/32848 | | 9/1997 |
| WO | WO-98/30569 | | 7/1998 |
| WO | WO-99/01457 | | 1/1999 |
| WO | WO-2001/003680 | | 1/2001 |
| WO | WO-2002/046164 | | 6/2002 |
| WO | WO-2002/046183 | | 6/2002 |
| WO | WO-2003/000682 | | 1/2003 |
| WO | WO-2004/026836 | | 4/2004 |
| WO | WO-2004/107958 | | 12/2004 |
| WO | WO-2005/030758 | | 4/2005 |
| WO | WO-2005/040169 | | 5/2005 |
| WO | WO-2005/066136 | | 7/2005 |
| WO | WO-2005/112932 | | 12/2005 |
| WO | WO-2005/121138 | | 12/2005 |
| WO | WO-2006/024837 | | 3/2006 |
| WO | WO-2006/034419 | | 3/2006 |
| WO | WO-2006/083869 | | 8/2006 |
| WO | WO-2006/111169 | | 10/2006 |
| WO | WO-2007/039172 | | 4/2007 |
| WO | WO-2007/054453 | | 5/2007 |
| WO | WO-2007/091107 | | 8/2007 |
| WO | WO-2008/014219 | | 1/2008 |
| WO | WO-2008/053341 | | 5/2008 |
| WO | WO-2008/077597 | | 7/2008 |
| WO | WO-2008/117061 | | 10/2008 |
| WO | WO-2008/130581 | | 10/2008 |
| WO | WO-2009/019505 | | 2/2009 |
| WO | WO-2009/036275 | | 3/2009 |
| WO | WO-2009/126691 | | 10/2009 |
| WO | WO-2010/037050 | | 4/2010 |
| WO | WO-2010/091176 | | 8/2010 |
| WO | WO-2012/065065 | | 5/2012 |
| WO | WO-2012/068274 | | 5/2012 |
| WO | WO-2013/151975 | | 10/2013 |
| WO | WO-2014/055634 | | 4/2014 |
| WO | WO-2014/101120 | | 7/2014 |
| WO | WO-2014/105666 | | 7/2014 |
| WO | WO-2014/122067 | | 8/2014 |
| WO | WO-2015/007669 | | 1/2015 |
| WO | WO-2015/049624 | | 4/2015 |
| WO | WO-2015/150564 | | 10/2015 |
| WO | WO-2016/038045 | | 3/2016 |
| WO | WO-2017/182983 | | 10/2017 |
| WO | WO-2017/182984 | | 10/2017 |
| WO | WO-2017/182986 | | 10/2017 |
| WO | WO-2018/056453 | | 3/2018 |
| WO | WO-2018/106818 | | 6/2018 |
| WO | WO-2018/109607 | | 6/2018 |
| WO | WO-2018/178947 | | 10/2018 |
| WO | WO-2019/013311 | | 1/2019 |
| WO | WO-2019/089670 | | 5/2019 |
| WO | WO-2019/126424 | | 6/2019 |
| WO | WO-2019/166951 | | 6/2019 |
| WO | WO-2019/158731 | | 8/2019 |
| WO | WO 2019166951 | A1 | 9/2019 |
| WO | WO-2019/239319 | | 12/2019 |
| WO | WO-2019/239371 | | 12/2019 |
| WO | WO-2020/001321 | | 1/2020 |
| WO | WO-2020/024232 | | 1/2020 |
| WO | WO-2020/089453 | | 5/2020 |
| WO | WO-2020/089455 | | 5/2020 |
| WO | WO-2020/103815 | | 5/2020 |
| WO | WO 2020089453 | A1 | 5/2020 |
| WO | WO 2020089455 | A1 | 5/2020 |
| WO | WO-2020/135513 | | 7/2020 |
| WO | WO-2020/163236 | | 8/2020 |
| WO | WO-2020/182990 | | 9/2020 |
| WO | WO-2020/207474 | | 10/2020 |
| WO | WO-2020/263695 | | 12/2020 |
| WO | WO-2021/018023 | | 2/2021 |
| WO | WO-2021/081207 | | 4/2021 |
| WO | WO-2021/096284 | | 5/2021 |
| WO | WO-2021/096304 | | 5/2021 |
| WO | WO-2021/155841 | | 8/2021 |
| WO | WO-2021/160127 | | 8/2021 |
| WO | WO-2021/219019 | | 11/2021 |
| WO | WO-2022/017338 | | 1/2022 |
| WO | WO-2022/048665 | A1 | 3/2022 |
| WO | WO-2022/053010 | A1 | 3/2022 |
| WO | WO-2023/016546 | A1 | 2/2023 |
| WO | WO-2023/169456 | A1 | 9/2023 |
| WO | WO-2024/169952 | A1 | 2/2024 |
| WO | WO-2024/125602 | A1 | 6/2024 |
| WO | WO-2024/137426 | A1 | 6/2024 |
| WO | WO-2024/153070 | A1 | 7/2024 |
| WO | WO-2025/002250 | A1 | 1/2025 |

OTHER PUBLICATIONS

Huang et al., "Discovery of Brigatinib (AP26113), a Phosphine Oxide-Containing, Potent, Orally Active Inhibitor of Anaplastic Lymphoma Kinase", Journal of Medicinal Chemistry (2016), 59(10), 4948-4964.

Paternoster, et al. Dissecting the Physiology and Pathophysiology of Glucagon-Like Peptide-1. Frontiers in Endocrinology. Oct. 2018; vol. 9, Article 584. pp. 1-26.

Taing, et al. GLP-1 (28-36) amide, the Glucagon-like peptide-1 metabolite: friend, foe, or pharmacological folly? Drug Design, Development and Therapy 2014, 8, 677-688.

Montrose-Rafizadeh, et al. Pancreatic Glucagon-Like Peptide-1 Receptor Couples to Multiple G Proteins and Activates Mitogen-Activated Protein Kinase Pathways in Chinese Hamster Ovary Cells. Endocrinology 1999, 40(3), 1132-1140.

Tomas, et al. New Insights into Beta-Cell GLP-1 Receptor and cAMP Signaling. Journal of Molecular Biology. (2020) 432, 1347-1366.

Bavec, et al. Different role of intracellular loops of glucagon-like peptide-1 receptor in G-protein coupling. Regul Pept. 2003, 111:137-144.

Hallbrink, et al. Different domains in the third intracellular loop of the GLP-1 receptor are responsible for Galpha(s) and Galpha(i)/Galpha(o) activation. Biochim Biophys Acta. 2001, 1546:79-86.

Walsh, et al. Eating Disorders. in Harrison's Principles of Internal Medicine (McGraw-Hill Book Company, New York, 2005 Kasper, Dennis L., Harrison, Tinsley Randolph. Eds. pp. 430-433.

Ramos, et al. Designing drugs that combat kidney damage. Expert Opinion on Drug Discovery. (2015), 10(5), 541-556.

Nauck, et al. GLP-1 receptor agonists in type 1 diabetes: a MAG1C bullet? The Lancet Diabetes & Endocrinology. vol. 8, Issue 4, Apr. 2020, p. 262.

Petit-Demouliere, et al. Forced swimming test in mice: a review of antidepressant activity. Psychopharmacology. 2005, 177, 245-255.

Miyamoto "Pharmacological treatment of schizophrenia: a critical review of the pharmacology and clinical effects of current and future therapeutic agents" Molecular Psychiatry (2012) 17, 1206 -1227.

Marcotte, et al. Animal models of schizophrenia: a critical review. Psychiatry Neurosci. 2001; 26(5):395-410.

DeWeerdt. Parkinson's disease 4 Big Questions. Nature. vol. 538, Oct. 2016, S17.

Bergman et al. Safety, Tolerability, Pharmacokinetics, and Pharmacodynamics of a Liver-Targeting Acetyl-CoA Carbonxylase Inhibitor (PF-05221304): A Three-Part Randomized Phase 1 Study, Clinical Pharmacology in Drug Development, 2020, 9(4) 514-526 (with Supporting Information, Figure S1, 1 page).

Ulrich Lucking "Sulfoximines in Medicinal Chemistry: Emerging Trends and Opportunities from the Drug Designer's Perspective" May 18, 2022, pp. 1-11.

(56) References Cited

OTHER PUBLICATIONS

Yu Han, "Application of Sulfoximines in medicinal chemistry from 2013 to 2020" European Journal of Medicinal Chemistry, vol. 209, Jan. 1, 2021, 1 page.
Stambirskyi, M. V., et al, (2021). Phosphine oxides (-POME2) for Medicinal chemistry: synthesis, properties, and applications. The Journal of Organic Chemistry, 86(18), 12783-12801.

* cited by examiner

HETEROCYCLIC GLP-1 AGONISTS

CROSS REFERENCE TO RELATED APPLICATION

This application is a National Stage application under 35 U.S.C. § 371 of International Patent Application No. PCT/CN2021/117263, filed on Sep. 8, 2021, which claims the benefit of International Patent Application Number PCT/CN2020/0114319, filed on Sep. 10, 2020, each of which is incorporated herein by reference in its entirety.

TECHNICAL FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take antidiabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

Accordingly, provided herein are compounds of Formula I:

Formula (I)

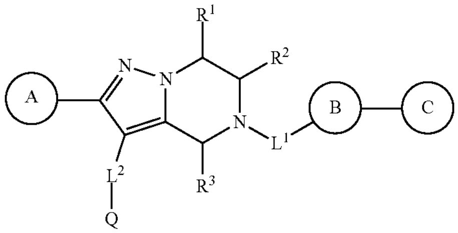

or a pharmaceutically acceptable salt or solvate thereof, wherein:

Ring A is $C_{6-10}$ aryl, $C_{5-10}$ cycloalkyl, 5-10 membered heterocyclyl, or 5-10 membered heteroaryl, each of which is optionally substituted with from 1-5 substituents each independently selected from the group consisting of: halo, $C_{1-6}$ alkyl, $C_{1-6}$ haloalkyl, and $C_{1-6}$ alkoxy;

$R^1$, $R^2$ and $R^3$ are each independently selected from the group consisting of H and $C_{1-6}$ alkyl which is optionally substituted with from 1-6 substituents each independently selected from the group consisting of halo, —OH, and $C_{1-6}$ alkoxy;

$L^1$ is selected from the group consisting of: —C(=O)—, —$CH_2$—, —CH($C_{1-6}$ alkyl)-, and —S(=O)$_2$;

Ring B is selected from the group consisting of:

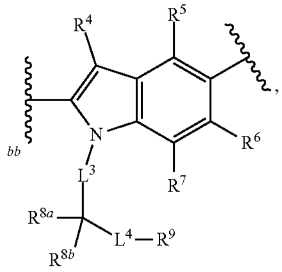,

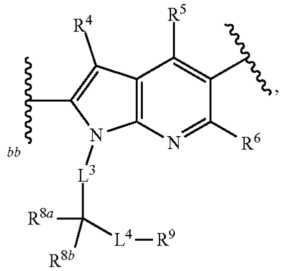,

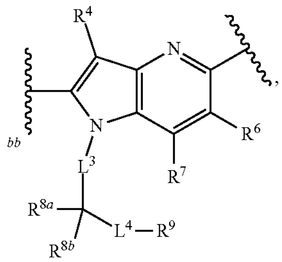, and

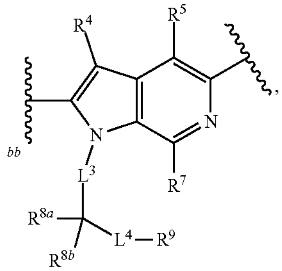, wherein bb represents point of attachment to L;

$R^4$, $R^5$, $R^6$, and $R^7$ are independently selected from the group consisting of: H, halo, and $C_{1-6}$ alkyl;

$L^3$ is a bond or $C_{1-3}$ alkylene;

$L^4$ is a bond or $C_{1-5}$ alkylene;

$R^{8a}$ and $R^{8b}$ are independently selected from the group consisting of: H and $C_{1-6}$ alkyl optionally substituted with one or more substituents independently selected from the group consisting of: halo and $C_{3-15}$ cycloalkyl; or $R^{8a}$ and $R^{8b}$ taken together with the carbon atom to which each is attached forms a $C_{3-15}$ cycloalkyl ring which is optionally substituted with from 1-3 independently selected $C_{1-6}$ alkyl, wherein the $C_{1-6}$ alkyl is optionally substituted with from 1-6 independently selected $R^f$;

$R^9$ is selected from the group consisting of: C(═O)OH, C(═O)(OC$_{1-6}$ alkyl), C(═O)NR$^{9a}$R$^{9b}$, (IX-1), (IX-2), (IX-3), and (IX-4):

(IX-1)

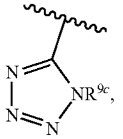

(IX-2)

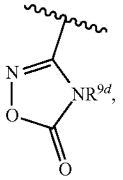

(IX-3)

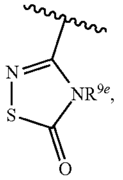 and (IX-4)

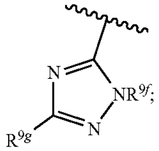

$R^{9a}$ is H or $C_{1-6}$ alkyl;

$R^{9b}$ is H, $C_{1-6}$ alkyl, C(═O)(C$_{1-6}$ alkyl), S(O)$_{0-2}$(C$_{1-6}$ alkyl), or cyano;

$R^{9c}$, $R^{9d}$, $R^{9e}$, $R^{9f}$, and $R^{9g}$ are each independently selected from the group consisting of: H; $C_{1-6}$ alkyl optionally substituted with from 1-6 independently selected halo and $C_{1-6}$ alkoxy; and C(═O)(C$_{1-6}$ alkyl);

Ring C is selected from the group consisting of 3-12 membered heterocyclyl; $C_{3-10}$ cycloalkyl; and 5-10 membered heteroaryl, each of which is optionally substituted with from 1-3 $R^{Ca}$;

each $R^{Ca}$ is independently selected from the group consisting of: halo, $C_{1-6}$ alkyl, $C_{1-6}$ haloalkyl, $C_{1-6}$ alkoxy, and $NR^cR^d$;

or a pair of $R^{Ca}$ on the same or different ring atoms, taken together with the ring atom(s) to which each is attached, forms a carbocyclic ring including from 3-8 ring atoms;

$L^2$ is selected from the group consisting of:

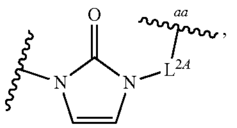

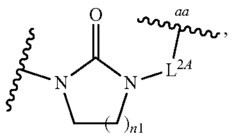

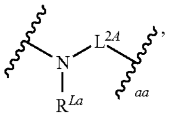

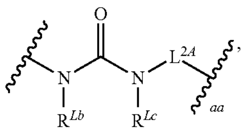 and

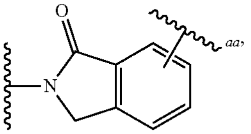

wherein aa represents the point of attachment to Q;

n1 is an integer from 1-3;

$L^{2A}$ is a bond or $C_{1-10}$ alkylene;

$R^{La}$ is selected from the group consisting of H, $C_{1-6}$ alkyl, and C(═O)(C$_{1-6}$ alkyl);

each of $R^{Lb}$ and $R^{Lc}$ is independently selected from the group consisting of H and $C_{1-6}$ alkyl;

Q is selected from the group consisting of: $C_{1-10}$ alkyl; $C_{3-15}$ cycloalkyl; 3-12 membered heterocyclyl; 5-10 membered heteroaryl; and $C_{6-10}$ aryl, each of which is optionally substituted with from 1-6 independently selected $R^Q$;

each $R^Q$ is independently selected from the group consisting of:

(a) halo;

(b) cyano;

(c) OH or oxo;

(d) —NR$^c$R$^d$;

(e) —C(═O)NR$^c$R$^d$ or —S(O)$_2$NR$^c$R$^d$;

(f) —S(═O)$_{0-2}$R$^e$;

(g) $C_{1-6}$ alkyl optionally substituted with from 1-6 independently selected $R^f$;

(h) $C_{1-6}$ alkoxy optionally substituted with from 1-6 independently selected $R^f$;

(i) 3-12 membered heterocyclyl optionally substituted with from 1-6 independently selected $R^g$;

(j) $C_{6-10}$ aryl optionally substituted with from 1-6 independently selected $R^g$;

(k) 5-10 membered heteroaryl optionally substituted with from 1-6 independently selected $R^g$;

(l) $C_{3-8}$ cycloalkyl optionally substituted with from 1-6 independently selected $R^g$;

(m) P(═O)R$^a$R$^b$; and (n) —(CR$^h$R$^h$)$_{q1}$—S(O)$_2$-L$^e$-R$^e$, wherein q1 is 1, 2, or 3;

$R^a$ and $R^b$ are independently selected from the group consisting of $C_{1-6}$ alkyl which is optionally substituted with from 1-6 substituents each independently selected from the group consisting of $C_{1-6}$ alkoxy, $C_{3-6}$ cycloalkyl, and halo; $C_{3-6}$ cycloalkyl optionally substituted with from 1-3 substituents each independently selected from the group consisting of $C_{1-3}$ alkyl and halo; and $C_{6-10}$ aryl optionally substituted with from 1-3 independently selected $C_{1-3}$ alkyl; or $R^a$ and $R^b$ taken together with the phosphorous atom to which each is attached forms a ring including from 5-8 ring atoms, wherein from 0-2 ring atoms (in addition to the phosphorous attached to $R^a$ and $R^b$) are heteroatoms each independently selected from the group consisting of: O, S, and N, wherein the ring is optionally substituted with from 1-3 independently selected $C_{1-6}$ alkyl;

each $R^c$ and $R^d$ are independently selected from the group consisting of: H, $C_{1-6}$ alkyl, $C_{3-6}$ cycloalkyl, C(═O)($C_{1-6}$ alkyl), C(═O)($C_{3-6}$ cycloalkyl), C(═O)O($C_{1-6}$ alkyl), $S(O)_{1-2}$($C_{1-6}$ alkyl), and $S(O)_{1-2}$($C_{3-6}$ cycloalkyl), wherein the $C_{1-6}$ alkyl, C(═O)($C_{1-6}$ alkyl), C(═O)($C_{3-6}$ cycloalkyl), C(═O)O($C_{1-6}$ alkyl), $S(O)_{1-2}$($C_{1-6}$ alkyl), and $S(O)_{1-2}$($C_{3-6}$ cycloalkyl) are each optionally substituted with from 1-6 substituents independently selected from the group consisting of: —OH, halo, and $C_{1-6}$ alkoxy;

$R^e$ is H, or $R^e$ is selected from the group consisting of: $C_{1-6}$ alkyl, $C_{1-6}$ haloalkyl, $C_{1-6}$ alkoxy, $C_{1-6}$ haloalkoxy, $C_{3-6}$ cycloalkyl, and 3-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $NH_2$, NH($C_{1-3}$ alkyl), N($C_{1-3}$ alkyl)$_2$, $C_{1-3}$ alkoxy, and $C_{1-3}$ haloalkoxy;

$L^e$ is a bond, $NR^c$, or O;

each $R^f$ is independently selected from the group consisting of halo, —OH, $NR^cR^d$, $C_{1-6}$ alkoxy, $C_{1-6}$ haloalkoxy, and 3-12 membered heterocyclyl which is optionally substituted with from 1-4 substituents each independently selected from the group consisting of —OH, $C_{1-6}$ alkyl, and 3-12 membered heterocyclyl;

each $R^g$ is independently selected from the group consisting of: $C_{1-6}$ alkyl, $C_{1-6}$ haloalkyl, $C_{1-6}$ alkoxy, $C_{1-6}$ haloalkoxy, $NR^cR^d$, cyano, halo, $C_{3-6}$ cycloalkyl, and 3 to 12 membered heterocyclyl optionally substituted with one or more substituents each independently selected from the group consisting of $C_{1-6}$ alkyl and C(═O)$C_{1-6}$ alkyl; and each occurrence of $R^h$ is independently selected from the group consisting of: H, $C_{1-6}$ alkyl, $C_{1-6}$ haloalkyl, $C_{3-6}$ cycloalkyl, and halo; or a pair of $R^h$ on the same or different carbon atom(s), taken together with the carbon atom(s) connecting them forms $C_{3-6}$ cycloalkyl or 4-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $C_{1-3}$ alkoxy, and $C_{1-3}$ haloalkoxy.

Also provided herein are pharmaceutical compositions comprising a compound of Formula I, or a pharmaceutically acceptable salt or solvate thereof, and a pharmaceutically acceptable excipient.

Also provided herein are methods for treating type 2 diabetes mellitus in a patient in need thereof, the methods comprising administering to the patient a therapeutically effective amount of a compound of Formula I, or a pharmaceutically acceptable salt or solvate thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula I, or a pharmaceutically acceptable salt or solvate thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula I, or a pharmaceutically acceptable salt or solvate thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin A1c (HbA1c), fasting plasma glucose, non-fasting plasma glucose, or any combination thereof. In some embodiments, the level of HbA1c is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 kg/m$^2$. In some embodiments, the patient has a BMI greater than or about 30 kg/m$^2$.

In some embodiments, the methods for the treatment of type 2 diabetes mellitus comprise a reduction in fasting plasma glucose levels. In some embodiments, the fasting plasma glucose levels are reduced to about or below 100 mg/dL.

In some embodiments, the methods for the treatment of type 2 diabetes mellitus comprise a reduction in HbA1c levels. In some embodiments, the HbA1c levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 kg/m$^2$.

In some embodiments, the compound of Formula I, or a pharmaceutically acceptable salt or solvate thereof, or a pharmaceutical composition thereof, is administered orally.

In some embodiments, the methods of treatment for type 2 diabetes mellitus further comprise administering an additional therapy or therapeutic agent to the patient.

In some embodiments, the additional therapy or therapeutic agent is selected from the group consisting of an antidiabetic agent, an anti-obesity agent, a GLP-1 receptor agonist, an agent to treat non-alcoholic steatohepatitis (NASH), anti-emetic agent, gastric electrical stimulation, dietary monitoring, physical activity, or any combinations thereof. In some embodiments, the antidiabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the anti-obesity agent is selected from the group consisting of neuropeptide Y receptor type 2 (NPYR2) agonist, a NPYR1 or NPYR5 antagonist, a human proislet peptide (HIP), a cannabinoid receptor type 1 (CB1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, or any combinations thereof. In some embodiments, the compound of Formula I, or a pharmaceutically acceptable salt or solvate thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula I, or a pharmaceutically acceptable salt or solvate thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the invention will be apparent from the following detailed description and FIGURES, and from the claims.

DETAILED DESCRIPTION

Provided herein are heterocyclic GLP-1 agonists for use in the management of T2DM and other conditions where activation of GLP-1 activity is useful.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "halo" or "halogen" means —F (sometimes referred to herein as "fluoro" or "fluoros"), —Cl (sometimes referred to herein as "chloro" or "chloros"), —Br (sometimes referred to herein as "bromo" or "bromos"), and —I (sometimes referred to herein as "iodo" or "iodos").

As used herein, the term "alkyl" refers to saturated linear or branched-chain monovalent hydrocarbon radicals, containing the indicated number of carbon atoms. For example, "$C_{1-6}$ alkyl" refers to saturated linear or branched-chain monovalent hydrocarbon radicals of one to six carbon atoms. Non-limiting examples of alkyl include methyl, ethyl, 1-propyl, isopropyl, 1-butyl, isobutyl, sec-butyl, tert-butyl, 2-methyl-2-propyl, pentyl, neopentyl, and hexyl.

As used herein, the term "alkylene" refers to a divalent alkyl containing the indicated number of carbon atoms. For example, "$C_{1-3}$ alkylene" refers to a divalent alkyl having one to three carbon atoms (e.g., $—CH_2—$, $—CH(CH_3)—$, $—CH_2CH_2—$, or $—CH_2CH_2CH_2—$).

As used herein, the term "alkenyl" refers to a linear or branched mono-unsaturated hydrocarbon chain, containing the indicated number of carbon atoms. For example, "$C_{2-6}$ alkenyl" refers a linear or branched mono unsaturated hydrocarbon chain of two to six carbon atoms. Non-limiting examples of alkenyl include ethenyl, propenyl, butenyl, or pentenyl.

As used herein, the term "alkynyl" refers to a linear or branched di-unsaturated hydrocarbon chain, containing the indicated number of carbon atoms. For example, "$C_{2-6}$ alkynyl" refers to a linear or branched di-unsaturated hydrocarbon chain having two to six carbon atoms. Non-limiting examples of alkynyl include ethynyl, propynyl, butynyl, or pentynyl.

As used herein, the term "cycloalkyl" refers to a saturated or partially saturated cyclic hydrocarbon, containing the indicated number of carbon atoms. For example, "$C_{3-6}$ cycloalkyl" refers to a saturated or partially saturated cyclic hydrocarbon having three to six ring carbon atoms. Non-limiting examples of cycloalkyl include cyclopropyl, cyclobutyl, cyclopentyl, and cyclohexyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

As used herein, the term "heterocyclyl" refers to a mon-, bi-, tri-, or polycyclic nonaromatic ring system containing indicated number of ring atoms (e.g., 3-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or $S(O)_{0-2}$ (e.g., carbon atoms and 1-3, 1-6, or 1-9 heteroatoms of N, O, or $S(O)_{0-2}$ if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heteorocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, the term "aryl" refers to a mono-, bi-, tri- or polycyclic hydrocarbon group containing the indicated numbers of carbon atoms, wherein at least one ring in the system is aromatic (e.g., $C_6$ monocyclic, $C_{10}$ bicyclic, or $C_{14}$ tricyclic aromatic ring system). Examples of aryl groups include phenyl, naphthyl, tetrahydronaphthyl, and the like.

As used herein, the term "heteroaryl" refers to a mono-, bi-, tri- or polycyclic group having indicated numbers of ring atoms (e.g., 5-6 ring atoms; e.g., 5, 6, 9, 10, or 14 ring atoms); wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and $S(O)_{0-2}$. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others.

As used herein, the term "haloalkyl" refers to an alkyl radical as defined herein, wherein one or more hydrogen atoms is replaced with one or more halogen atoms. Non-limiting examples include fluoromethyl, difluoromethyl, trifluoromethyl, 2-fluoroethyl, 2,2-difluoroethyl, 2,2,2-trifluoroethyl, chloromethyl, dichloromethyl, chloroethyl, trichloroethyl, bromomethyl, and iodomethyl.

As used herein, the term "alkoxy" refers to an —O-alkyl radical, wherein the radical is on the oxygen atom. For example, "$C_{1-6}$ alkoxy" refers to an —O—($C_{1-6}$ alkyl) radical, wherein the radical is on the oxygen atom. Examples of alkoxy include methoxy, ethoxy, propoxy, isopropoxy, butoxy and tert-butoxy. Accordingly, as used herein, the term "haloalkoxy" refers to an —O-haloalkyl radical, wherein the radical is on the oxygen atom.

As used herein, "- - -" indicate an optional single or double bond, as allowed by valence. As used herein, "~~~" indicates the point of attachment to the parent molecule.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucose-dependent insulin secretion; suppress inappropriately elevated glucagon levels, both in fasting and postprandial states; and slow gastric emptying. Karla et al., Glucagon-like peptide-1 receptor agonists in the treatment of type 2 diabetes: Past, present, and future, *Indian J Endocrinol Metab.* 2016 March-April; 20(2): 254-267. GLP-1 RAs have been shown to treat type 2 diabetes. Examples of GLP-1 RAs include, but are not limited to, albiglutide (TANZEUM®), dulaglutide (LY2189265, TRULICITY®), efpeglenatide, exenatide (BYETTA®, BYDUREON®, Exendin-4), liraglutide (VICTOZA®, NN2211), lixisenatide (LYXUMIA®), semaglutide (OZEMPIC®), tirzepatide, ZP2929, NNC0113-0987, BPI-3016, and TT401. See, also, for example, additional GLP-1 recceptor agonists described in U.S. Pat. Nos. 10,370,426; 10,308,700; 10,259,823; 10,208,019; 9,920,106; 9,839,664; 8,129,343; 8,536,122; 7,919,598; 6,414,126; 6,628,343; and RE45313.

The term "pharmaceutically acceptable" as used herein indicates that the compound, or salt or composition thereof is compatible chemically and/or toxicologically with the other ingredients comprising a formulation and/or the patient being treated therewith.

The term "therapeutic compound" as used herein is meant to include, without limitation, all compounds of Formula I, or pharmaceutically acceptable salts or solvates thereof (e.g., a compound of any one of Formulas IA and IB, or a pharmaceutically acceptable salt or solvate thereof), and all compositions (e.g., pharmaceutical compositions) wherein a compound of Formula I, or a pharmaceutically acceptable salt or solvate thereof (e.g., a compound of any one of Formulas IA and IB, or a pharmaceutically acceptable salt or solvate thereof) is a component of the composition.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof (e.g., a compound of any one of Formulas IA and IB, or a pharmaceutically acceptable salt or solvate thereof)) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, P A, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009.

The term “pharmaceutical composition” refers to a mixture of a compound of Formula I, or a pharmaceutically acceptable salt or solvate thereof (e.g., a compound of any one of Formulas IA and IB or a pharmaceutically acceptable salt or solvate thereof) as described herein with other chemical components (referred to collectively herein as “excipients”), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms “treat,” “treating,” and “treatment,” in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term “preventing”, as used herein, is the prevention of the onset, recurrence or spread, in whole or in part, of the disease or condition as described herein, or a symptom thereof.

The terms “subject”, “patient” or “individual”, as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the patient is a human. In some embodiments, the subject has experienced and/or exhibited at least one symptom of the disease, disorder, or condition to be treated and/or prevented.

The terms “treatment regimen” and “dosing regimen” are used interchangeably to refer to the dose and timing of administration of each therapeutic agent in a combination of the invention.

The term “pharmaceutical combination”, as used herein, refers to a pharmaceutical treatment resulting from the mixing or combining of more than one active ingredient and includes both fixed and non-fixed combinations of the active ingredients.

The term “combination therapy” as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term “modulation”, as used herein, refers to a regulation or an adjustment (e.g., increase or decrease) and can include, for example agonism, partial agonism or antagonism.

Compounds

In one aspect, provided herein are compounds of Formula (I):

Formula (I)

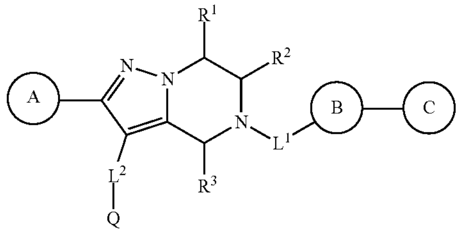

or a pharmaceutically acceptable salt or solvate thereof, wherein:

Ring A is $C_{6-10}$ aryl, $C_{5-10}$ cycloalkyl, 5-10 membered heterocyclyl, or 5-10 membered heteroaryl, each of which is optionally substituted with from 1-5 substituents each independently selected from the group consisting of: halo, $C_{1-6}$ alkyl, $C_{1-6}$ haloalkyl, and $C_{1-6}$ alkoxy;

$R^1$, $R^2$ and $R^3$ are each independently selected from the group consisting of H and $C_{1-6}$ alkyl which is optionally substituted with from 1-6 substituents each independently selected from the group consisting of halo, —OH, and $C_{1-6}$ alkoxy;

$L^1$ is selected from the group consisting of: —C(═O)—, —$CH_2$—, —CH($C_{1-6}$ alkyl)-, and —S(═O)$_2$;

Ring B is selected from the group consisting of:

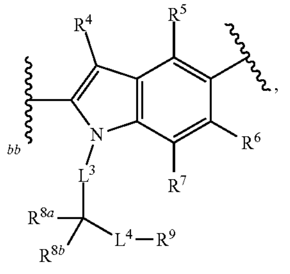

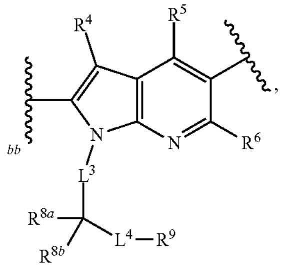

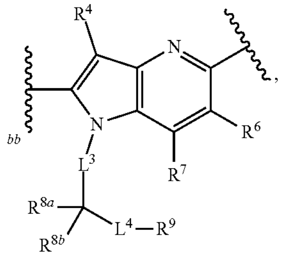

and

-continued

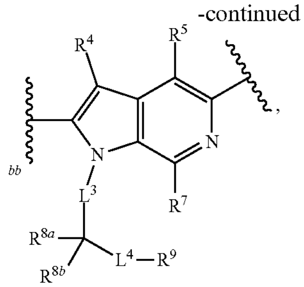

wherein bb represents point of attachment to $L^1$;

$R^4$, $R^5$, $R^6$, and $R^7$ are independently selected from the group consisting of: H, halo, and $C_{1-6}$ alkyl;

$L^3$ is a bond or $C_{1-3}$ alkylene;

$L^4$ is a bond or $C_{1-5}$ alkylene;

$R^{8a}$ and $R^{8b}$ are independently selected from the group consisting of: H and $C_{1-6}$ alkyl optionally substituted with one or more substituents independently selected from the group consisting of: halo and $C_{3-15}$ cycloalkyl; or $R^{8a}$ and $R^{8b}$ taken together with the carbon atom to which each is attached forms a $C_{3-15}$ cycloalkyl ring which is optionally substituted with from 1-3 independently selected $C_{1-6}$ alkyl, wherein the $C_{1-6}$ alkyl is optionally substituted with from 1-6 independently selected R;

$R^9$ is selected from the group consisting of: C(═O)OH, C(═O)(O$C_{1-6}$ alkyl), C(═O)N$R^{9a}R^{9b}$, (IX-1), (IX-2), (IX-3), and (IX-4):

(IX-1)

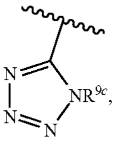

(IX-2)

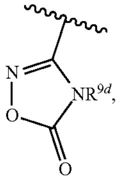

(IX-3)

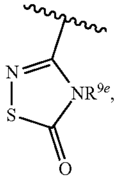

and (IX-4)

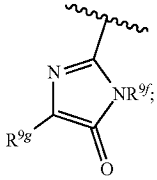

$R^{9a}$ is H or $C_{1-6}$ alkyl;

$R^{9b}$ is H, $C_{1-6}$ alkyl, C(═O)($C_{1-6}$ alkyl), $S(O)_{0-2}$($C_{1-6}$ alkyl), or cyano;

$R^{9c}$, $R^{9d}$, $R^{9e}$, $R^{9f}$, and $R^{9g}$ are each independently selected from the group consisting of: H; $C_{1-6}$ alkyl optionally substituted with from 1-6 independently selected halo and $C_{1-6}$ alkoxy; and C(═O)($C_{1-6}$ alkyl);

Ring C is selected from the group consisting of 3-12 membered heterocyclyl; $C_{3-10}$ cycloalkyl; and 5-10 membered heteroaryl, each of which is optionally substituted with from 1-3 $R^{Ca}$;

each $R^{Ca}$ is independently selected from the group consisting of: halo, $C_{1-6}$ alkyl, $C_{1-6}$ haloalkyl, $C_{1-6}$ alkoxy, and $NR^cR^d$;

or a pair of $R^{Ca}$ on the same or different ring atoms, taken together with the ring atom(s) to which each is attached, forms a carbocyclic ring including from 3-8 ring atoms;

$L^2$ is selected from the group consisting of:

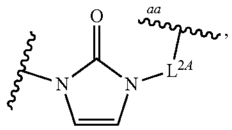

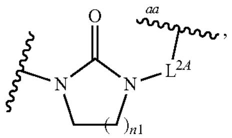

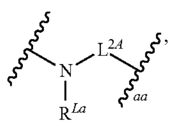

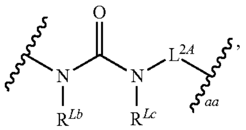

and

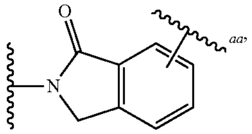

wherein aa represents the point of attachment to Q;

n1 is an integer from 1-3;

$L^{2A}$ is a bond or $C_{1-10}$ alkylene;

$R^{La}$ is selected from the group consisting of H, $C_{1-6}$ alkyl, and C(═O)($C_{1-6}$ alkyl);

each of $R^{Lb}$ and $R^{Lc}$ is independently selected from the group consisting of H and $C_{1-6}$ alkyl;

Q is selected from the group consisting of: $C_{1-10}$ alkyl; $C_{3-15}$ cycloalkyl; 3-12 membered heterocyclyl; 5-10 membered heteroaryl; and $C_{6-10}$ aryl, each of which is optionally substituted with from 1-6 independently selected $R^Q$;

each $R^Q$ is independently selected from the group consisting of:

(a) halo;

(b) cyano;

(c) OH or oxo;

(d) —$NR^cR^d$;

(e) —C(═O)$NR^cR^d$ or —$S(O)_2NR^cR^d$;

(f) —$S(═O)_{0-2}R^e$;

(g) $C_{1-6}$ alkyl optionally substituted with from 1-6 independently selected $R^f$;

(h) $C_{1-6}$ alkoxy optionally substituted with from 1-6 independently selected $R^f$;

(i) 3-12 membered heterocyclyl optionally substituted with from 1-6 independently selected $R^g$;

(j) $C_{6-10}$ aryl optionally substituted with from 1-6 independently selected $R^g$;

(k) 5-10 membered heteroaryl optionally substituted with from 1-6 independently selected $R^g$;

(l) $C_{3-8}$ cycloalkyl optionally substituted with from 1-6 independently selected $R^g$;

(m) P(═O)$R^aR^b$; and (n) —$(CR^hR^h)_{q1}$—$S(O)_2$-$L^e$-$R^e$, wherein q1 is 1, 2, or 3;

$R^a$ and $R^b$ are independently selected from the group consisting of $C_{1-6}$ alkyl which is optionally substituted with from 1-6 substituents each independently selected from the group consisting of $C_{1-6}$ alkoxy, $C_{3-6}$ cycloalkyl, and halo; $C_{3-6}$ cycloalkyl optionally substituted with from 1-3 substituents each independently selected from the group consisting of $C_{1-3}$ alkyl and halo; and $C_{6-10}$ aryl optionally substituted with from 1-3 independently selected $C_{1-3}$ alkyl; or $R^a$ and $R^b$ taken together with the phosphorous atom to which each is attached forms a ring including from 5-8 ring atoms, wherein from 0-2 ring atoms (in addition to the phosphorous attached to $R^a$ and $R^b$) are heteroatoms each independently selected from the group consisting of: O, S, and N, wherein the ring is optionally substituted with from 1-3 independently selected $C_{1-6}$ alkyl;

each $R^c$ and $R^d$ are independently selected from the group consisting of: H, $C_{1-6}$ alkyl, $C_{3-6}$ cycloalkyl, C(═O)($C_{1-6}$ alkyl), C(═O)($C_{3-6}$ cycloalkyl), C(═O)O($C_{1-6}$ alkyl), $S(O)_{1-2}$($C_{1-6}$ alkyl), and $S(O)_{1-2}$($C_{3-6}$ cycloalkyl), wherein the $C_{1-6}$ alkyl, C(═O)($C_{1-6}$ alkyl), C(═O)($C_{3-6}$ cycloalkyl), C(═O)O($C_{1-6}$ alkyl), $S(O)_{1-2}$($C_{1-6}$ alkyl), and $S(O)_{1-2}$($C_{3-6}$ cycloalkyl) are each optionally substituted with from 1-6 substituents independently selected from the group consisting of: —OH, halo, and $C_{1-6}$ alkoxy;

$R^e$ is H, or $R^e$ is selected from the group consisting of: $C_{1-6}$ alkyl, $C_{1-6}$ haloalkyl, $C_{1-6}$ alkoxy, $C_{1-6}$ haloalkoxy, $C_{3-6}$ cycloalkyl, and 3-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $NH_2$, NH($C_{1-3}$ alkyl), N($C_{1-3}$ alkyl)$_2$, $C_{1-3}$ alkoxy, and $C_{1-3}$ haloalkoxy;

$L^e$ is a bond, $NR^c$, or O;

each $R^f$ is independently selected from the group consisting of halo, —OH, $NR^cR^d$, $C_{1-6}$ alkoxy, $C_{1-6}$ haloalkoxy, and 3-12 membered heterocyclyl which is optionally substituted with from 1-4 substituents each independently selected from the group consisting of —OH, $C_{1-6}$ alkyl, and 3-12 membered heterocyclyl;

each $R^g$ is independently selected from the group consisting of: $C_{1-6}$ alkyl, $C_{1-6}$ haloalkyl, $C_{1-6}$ alkoxy, $C_{1-6}$ haloalkoxy, $NR^cR^d$, cyano, halo, $C_{3-6}$ cycloalkyl, and 3 to 12 membered heterocyclyl optionally substituted with one or more substituents each independently selected from the group consisting of $C_{1-6}$ alkyl and C(═O)$C_{1-6}$ alkyl; and each occurrence of $R^h$ is independently selected from the group consisting of: H, $C_{1-6}$ alkyl, $C_{1-6}$ haloalkyl, $C_{3-6}$ cycloalkyl, and halo; or a pair of $R^h$ on the same or different carbon atom(s), taken together with the carbon atom(s) connecting them forms $C_{3-6}$ cycloalkyl or 4-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $C_{1-3}$ alkoxy, and $C_{1-3}$ haloalkoxy.

Embodiments can include any one or more of the features delineated below and/or in the claims.

In some embodiments of Formula (I), Q is selected from the group consisting of: $C_{3-15}$ cycloalkyl; 3-12 membered heterocyclyl; 5-10 membered heteroaryl; and $C_{6-10}$ aryl, each of which is optionally substituted with from 1-6 independently selected $R^Q$. In some embodiments, Q is selected from the group consisting of: 5-10 membered heteroaryl and $C_{6-10}$ aryl, each of which is optionally substituted with from 1-6 independently selected $R^Q$. In some embodiments, Q is 5-10 membered heteroaryl optionally substituted with from 1-6 independently selected $R^Q$. In some embodiments, Q is 9-10 membered heteroaryl optionally substituted with from 1-6 independently selected $R^Q$. In some embodiments, Q is 9 membered heteroaryl optionally substituted with from 1-6 independently selected $R^Q$. In some embodiments, Q is 9 membered heteroaryl optionally substituted with from 1-2 independently selected $R^Q$.

In some embodiments of Formula (I), Q is

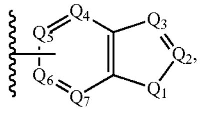

wherein: $Q^1$ is NH or $NR^Q$; $Q^2$ and $Q^3$ are each independently N, CH, or $CR^Q$; one of $Q^4$, $Q^5$, $Q^6$, and $Q^7$ is a carbon atom bonded to $L^2$; and the other three of $Q^4$, $Q^5$, $Q^6$, and $Q^7$ are each independently N, CH, or $CR^Q$. In some embodiments, $Q^1$ is NH or $NR^Q$; $Q^2$ and $Q^3$ are each independently N, CH, or $CR^Q$; one of $Q^4$, $Q^5$, $Q^6$, and $Q^7$ is a carbon atom bonded to $L^2$; and the other three of $Q^4$, $Q^5$, $Q^6$, and $Q^7$ are each independently CH or $CR^Q$. In some embodiments, $Q^1$ is NH or $NR^Q$; $Q^2$ and $Q^3$ are each independently N, CH, or $CR^Q$; one of $Q^4$, $Q^5$, $Q^6$, and $Q^7$ is a carbon atom bonded to $L^2$; and the other three of $Q^4$, $Q^5$, $Q^6$, and $Q^7$ are each independently CH or $CR^Q$.

In some embodiments, $Q^1$ is NH. In some embodiments, $Q^1$ is $NR^Q$.

In some embodiments, $Q^2$ is N and $Q^3$ is N, CH or $CR^Q$.

In some embodiments, one of $Q^4$, $Q^5$, $Q^6$, and $Q^7$ is a carbon atom bonded to $L^2$ two of $Q^4$, $Q^5$, $Q^6$, and $Q^7$ are each CH; and one of $Q^4$, $Q^5$, $Q^6$, and $Q^7$ is CH or $CR^Q$ (e.g., $CR^Q$).

In some embodiments, one $R^Q$ is present. In some embodiments, two $R^Q$ are present. In some embodiments, three $R^Q$ are present. In some embodiments, at least one $R^Q$ is attached to the 6-membered ring. In some embodiments, two $R^Q$ are present, and at least one of the two $R^Q$ is attached to the 6-membered ring.

In some embodiments of Formula (I), Q is

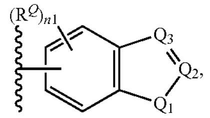

wherein: $Q^1$ is NH or $NR^Q$; $Q^2$ and $Q^3$ are each independently N, CH, or $CR^Q$; and n1 is 0 or 1.

In some embodiments, $Q^1$ is NH. In some embodiments, $Q^1$ is $NR^Q$.

In some embodiments, $Q^2$ is N and $Q^3$ is N, CH or $CR^Q$.

In some embodiments, one $R^Q$ is present. In some embodiments, two $R^Q$ are present. In some embodiments, three $R^Q$ are present. In some embodiments, at least one $R^Q$ is attached to the 6-membered ring. In some embodiments, two $R^Q$ are present, and at least one of the two $R^Q$ is attached to the 6-membered ring.

In some embodiments of Formula (I), Q is

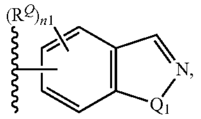

wherein: $Q^1$ is NH or $NR^Q$; and n1 is 0 or 1.

In some embodiments, $Q^1$ is NH. In some embodiments, $Q^1$ is $NR^Q$.

In some embodiments, one $R^Q$ is present. In some embodiments, two $R^Q$ are present. In some embodiments, two $R^Q$ are present, and at least one of the two $R^Q$ is attached to the 6-membered ring.

In some embodiments of Formula (I), Q is

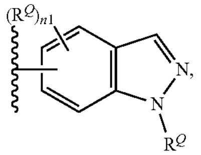

wherein n1 is 0 or 1.

In some embodiments, Q is

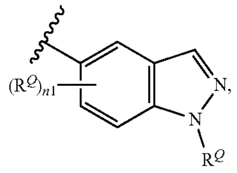

wherein n1 is 0 or 1.

In some embodiments, n1 is 0. In some embodiments, n1 is 1.

In some embodiments of Formula (I), Q is

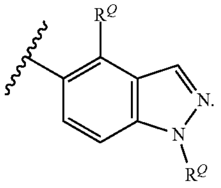

In some embodiments of Formula (I), Q is

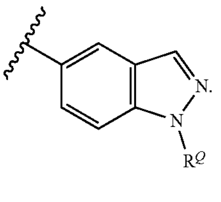

In some embodiments of Formula (I), when at least one $R^Q$ (e.g., an $R^Q$ attached to a ring N) is present, one $R^Q$ is selected from the group consisting of:

(a) halo;
(b) cyano;
(c) OH;
(d) $—NR^cR^d$;
(e) $—C(═O)NR^cR^d$ or $—S(O)_2NR^cR^d$;
(f) $—S(═O)_{0-2}R^e$;
(g) $C_{1-6}$ alkyl optionally substituted with from 1-6 independently selected R;
(h) $C_{1-6}$ alkoxy optionally substituted with from 1-6 independently selected R;
(i) 3-12 membered heterocyclyl optionally substituted with from 1-6 independently selected $R^g$;
(j) $C_{6-10}$ aryl optionally substituted with from 1-6 independently selected $R^g$;
(k) 5-10 membered heteroaryl optionally substituted with from 1-6 independently selected $R^g$;
(l) $C_{3-8}$ cycloalkyl optionally substituted with from 1-6 independently selected $R^g$;
(m) $P(═O)R^aR^b$; and
(n) $—(CR^hR^h)_{q1}—S(O)_2-L^e-R^e$, wherein q1 is 1, 2, or 3;

and each remaining $R^Q$, when present, is independently selected from: halo, cyano, OH, $C_{1-6}$ alkyl, and $C_{1-6}$ alkoxy.

In some embodiments, when at least one $R^Q$ is present, one $R^Q$ (e.g., an $R^Q$ attached to a ring N) is selected from the group consisting of:

(a) halo;
(b) cyano;
(c) OH;
(d) $—NR^cR^d$;
(e) $—C(═O)NR^cR^d$ or $—S(O)_2NR^cR^d$;
(f) $—S(═O)_{0-2}R^e$;
(g) $C_{1-6}$ alkyl optionally substituted with from 1-6 independently selected R; and
(h) $C_{1-6}$ alkoxy optionally substituted with from 1-6 independently selected R; and each remaining $R^Q$, when present, is an independently selected halo.

In some embodiments, when at least one $R^Q$ is present, one $R^Q$ (e.g., an $R^Q$ attached to a ring N) is an independently selected $C_{1-6}$ alkyl optionally substituted with from 1-6 independently selected R; and each remaining $R^Q$, when present, is independently selected halo. In some embodiments, when at least one $R^Q$ is present, one $R^Q$ (e.g., an $R^Q$ attached to a ring N) is an independently selected $C_{1-3}$ alkyl optionally substituted with from 1-6 independently selected R; and each remaining $R^Q$, when present, is fluoro. In some embodiments, when at least one $R^Q$ is present, one $R^Q$ (e.g., an $R^Q$ attached to a ring N) is an independently selected unsubstituted $C_{1-3}$ alkyl; and each remaining $R^Q$, when present, is fluoro. In some embodiments, when at least one $R^Q$ is present, one $R^Q$ (e.g., an $R^Q$ attached to a ring N) is methyl; and each remaining $R^Q$, when present, is fluoro.

In some embodiments, two $R^Q$ are present; one $R^Q$ (e.g., an $R^Q$ attached to a ring N) is an independently selected $C_{1-6}$ alkyl optionally substituted with from 1-6 independently selected R; and the other $R^Q$ is halo. In some embodiments, two $R^Q$ are present; one $R^Q$ (e.g., an $R^Q$ attached to a ring N) is an independently selected $C_{1-3}$ alkyl optionally substituted with from 1-6 independently selected R; and the other $R^Q$ is fluoro. In some embodiments, two $R^Q$ are present; one $R^Q$ (e.g., an $R^Q$ attached to a ring N) is an independently selected unsubstituted $C_{1-3}$ alkyl; and the other $R^Q$, is fluoro. In some embodiments, two $R^Q$ are present; one $R^Q$ (e.g., an $R^Q$ attached to a ring N) is methyl; and the other $R^Q$ is fluoro.

In some embodiments, one $R^Q$ is present (e.g., an $R^Q$ attached to a ring N) and is an independently selected $C_{1-6}$ alkyl optionally substituted with from 1-6 independently selected R. In some embodiments, one $R^Q$ is present (e.g., an $R^Q$ attached to a ring N) and is an independently selected $C_{1-3}$ alkyl optionally substituted with from 1-6 independently selected R. In some embodiments, one $R^Q$ is present (e.g., an $R^Q$ attached to a ring N) and is an independently selected unsubstituted $C_{1-3}$ alkyl. In some embodiments, one $R^Q$ is present (e.g., an $R^Q$ attached to a ring N) and is methyl.

In some embodiments, Q is

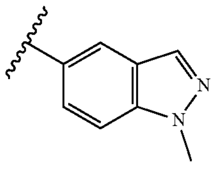

or

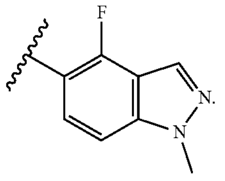

In some embodiments of Formula (I), Q is $C_{6-10}$ aryl optionally substituted with from 1-6 independently selected $R^Q$. In some embodiments, Q is phenyl optionally substituted with from 1-6 independently selected $R^Q$. In some embodiments, Q is phenyl optionally substituted with from 1-2 independently selected $R^Q$. In some embodiments, Q is phenyl optionally substituted with 1-2 independently selected $R^Q$.

In some embodiments of Formula (I), Q is:

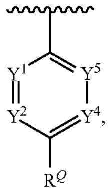

wherein $Y^1$, $Y^2$, $Y^4$, and $Y^5$ are each independently N, CH, or $CR^Q$. In some embodiments, $Y^1$, $Y^2$, $Y^4$, and $Y^5$ are each independently CH or $CR^Q$. In some embodiments, one or two of $Y^1$, $Y^2$, $Y^4$, and $Y^5$ are each independently CH or $CR^Q$; and the remaining $Y^1$, $Y^2$, $Y^4$, and $Y^5$ are CH.

In some embodiments, Q is

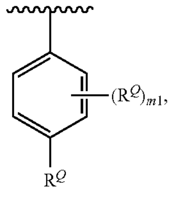

wherein m1 is 0, 1, or 2.

In some embodiments, the $R^Q$ para to $L^2$ is selected from the group consisting of:

(e) $—C(=O)NR^cR^d$ or $—S(O)_2NR^cR^d$;

(f) $—S(=O)_{0-2}R^e$;

(m) $P(=O)R^aR^b$; and (n) $—(CR^hR^h)_{q1}—S(O)_2-L^e-R^e$.

In some embodiments, the $R^Q$ para to $L^2$ is $—P(=O)R^aR^b$.

In some embodiments, $R^a$ and $R^b$ are independently selected $C_{1-6}$ alkyl optionally substituted with from 1-6 substituents each independently selected from the group consisting of $C_{1-6}$ alkoxy, $C_{3-6}$ cycloalkyl, and halo. In some embodiments, $R^a$ and $R^b$ are independently selected $C_{1-6}$ alkyl optionally substituted with from 1-2 substituents each independently selected from the group consisting of $C_{1-6}$ alkoxy, $C_{3-6}$ cycloalkyl, and halo. In some embodiments, $R^a$ and $R^b$ are independently selected $C_{1-3}$ alkyl optionally substituted with from 1-2 independently selected halo. In some embodiments, $R^a$ and $R^b$ are independently selected unsubstituted $C_{1-3}$ alkyl. In some embodiments, $R^a$ and $R^b$ are each ethyl.

In some embodiments, m1 is 0. In some embodiments, m1 is 1. In some embodiments, m1 is 2.

In some embodiments, Q is

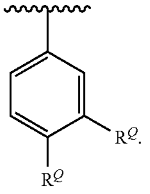

In some embodiments, the $R^Q$ that is meta to $L^2$ is $—NR^cR^d$. In some embodiments, each $R^c$ and $R^d$ are independently selected from the group consisting of: H, $C_{1-6}$ alkyl, $C(=O)(C_{1-6}$ alkyl), wherein the $C_{1-6}$ alkyl and $C(=O)(C_{1-6}$ alkyl) are each optionally substituted with from 1-6 substituents independently selected from the group consisting of: —OH, halo, and $C_{1-6}$ alkoxy. In some embodiments, each $R^c$ and $R^d$ are independently selected from the group consisting of: H, $C_{1-6}$ alkyl, $C(=O)(C_{1-6}$ alkyl), wherein the $C_{1-6}$ alkyl and $C(=O)(C_{1-6}$ alkyl) are each optionally substituted with from 1-6 substituents independently selected from the group consisting of: —OH, halo, and $C_{1-6}$ alkoxy. In some embodiments, each $R^c$ and $R^d$ are independently selected from H and $C_{1-6}$ alkyl, wherein the $C_{1-6}$ alkyl is optionally substituted with from 1-6 substituents independently selected from the group consisting of: —OH, halo, and $C_{1-6}$ alkoxy. In some embodiments, each $R^c$ and $R^d$ are independently selected from H and $C_{1-3}$ alkyl. In some embodiments, one of $R^c$ and $R^d$ is H, and the other of $R^c$ and $R^d$ is $C_{1-3}$ alkyl. In some embodiments, one of $R^c$ and $R^d$ is H, and the other of $R^c$ and $R^d$ is methyl.

In some embodiments, Q is

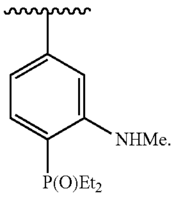

In some embodiments of Formula (I), $R^1$ is H. In some embodiments of Formula (I), $R^2$ is H. In some embodiments of Formula (I), $R^3$ is $C_{1-6}$ alkyl. For example, $R^3$ can be $C_{1-3}$ alkyl such as methyl. In some embodiments, $R^3$ is $C_{1-6}$ alkyl, and the carbon atom to which $R^3$ is attached has (S)-configuration.

In some embodiments of Formula (I), $R^1$, $R^2$, and $R^3$ are H.

In some embodiments of Formula (I), $R^1$ and $R^2$ are H; and $R^3$ is $C_{1-6}$ alkyl. In some embodiments, $R^1$ and $R^2$ are H; and $R^3$ is methyl. In some embodiments, the carbon atom to which $R^3$ is attached has (S)-configuration.

In some embodiments of Formula (I), $L^2$ is:

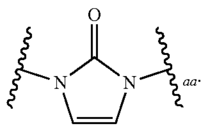 [SMILES: *n1ccn(*)c1=O]

In some embodiments of Formula (I), Ring A is $C_{6-10}$ aryl or 5-10 membered heteroaryl, each of which is optionally substituted with from 1-4 substituents each independently selected from the group consisting of halo, $C_{1-6}$ alkyl, $C_{1-6}$ haloalkyl, and $C_{1-6}$ alkoxy.

In some embodiments of Formula (I), Ring A is phenyl or pyridyl, each of which is optionally substituted with from 2-4 substituents each independently selected from the group consisting of halo, $C_{1-6}$ alkyl, $C_{1-6}$ haloalkyl, and $C_{1-6}$ alkoxy.

In some embodiments of Formula (I), Ring A is phenyl, which is optionally substituted with from 2-4 substituents each independently selected from the group consisting of halo and $C_{1-6}$ alkyl.

In some embodiments of Formula (I), Ring A is:

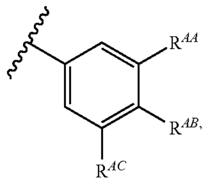

wherein $R^{AA}R^{AB}$, and $R^{AC}$ are independently halo or $C_{1-6}$ alkyl. In some embodiments, $R^{AA}$ and $R^{AC}$ are independently $C_{1-6}$ alkyl (e.g., $C_{1-3}$ alkyl, such as methyl). In some embodiments, $R^{AB}$ is halo (e.g., —F).

In some embodiments of Formula (I), Ring A is pyridyl, which is optionally substituted with from 2-4 substituents each independently selected from the group consisting of halo and $C_{1-6}$ alkyl.

In some embodiments of Formula (I), $L^1$ is C(═O).

In some embodiments of Formula (I), Ring B is:

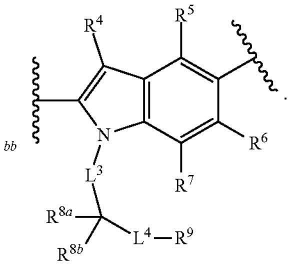

In some embodiments of Formula (I), $R^4$, $R^5$, and $R^6$ are each H or halo. In some embodiments, $R^4$, $R^5$, and $R^6$ are each H or —F. For example, $R^4$, $R^5$, and $R^6$ can each be H. As another non-limiting example, $R^4$ and $R^5$ can be H; and $R^6$ can be —F.

In some embodiments of Formula (I), $R^7$ is H. In some embodiments of Formula (I), $R^7$ is —F.

In some embodiments of Formula (I), Ring B is:

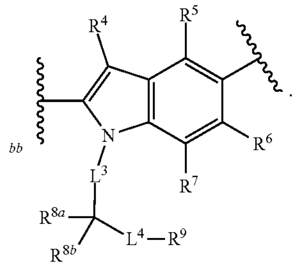

In some embodiments, $R^4$, $R^5$, and $R^6$ are each H or halo. In some embodiments, $R^4$, $R^5$, and $R^6$ are each H or —F. For example, $R^4$, $R^5$, and $R^6$ can each be H. As another non-limiting example, $R^4$ and $R^5$ can be H; and $R^6$ can be —F. In some embodiments, $R^7$ is H. In some embodiments of Formula (I), $R^7$ is —F.

In some embodiments of Formula (I), Ring B is:

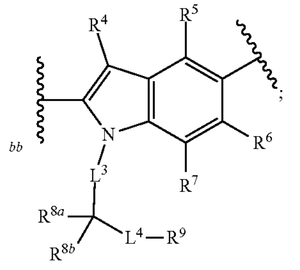

and $R^4$, $R^5$, $R^6$, and $R^7$ are each H.

In some embodiments of Formula (I), at least one of $L^3$ and $L^4$ is a bond. In some embodiments, both of $L^3$ and $L^4$ are bonds. In some embodiments, $L^3$ is a bond; and $L^4$ is $C_{1-2}$ alkylene. In some embodiments, $L^4$ is a bond; and $L^3$ is $C_{1-2}$ alkylene.

In some embodiments of Formula (I), $L^3$ and $L^4$ are each independently $C_{1-2}$ alkylene.

In some embodiments of Formula (I), $R^{8a}$ and $R^{8b}$ taken together with the carbon atom to which each is attached forms a $C_{3-8}$ cycloalkyl ring which is optionally substituted with from 1-2 (e.g., 1) independently selected $C_{1-6}$ alkyl, wherein the $C_{1-6}$ alkyl is optionally substituted with from 1-3 independently selected R. In some embodiments, $L^3$ is a bond; and $L^4$ is a bond.

In some embodiments of Formula (I), $R^{8a}$ and $R^{8b}$ taken together with the carbon atom to which each is attached forms a $C_{3-5}$(e.g., $C_3$ or $C_4$) cycloalkyl ring which is optionally substituted with from 1-2 (e.g., 1) independently selected $C_{1-6}$ alkyl, wherein the $C_{1-6}$ alkyl is optionally substituted with from 1-3 independently selected R. In some embodiments, $L^3$ is a bond; and $L^4$ is a bond.

In some embodiments of Formula (I), $R^{8a}$ and $R^{8b}$ taken together with the carbon atom to which each is attached forms a $C_{3-4}$ cycloalkyl ring which is optionally substituted with from 1-2 (e.g., 1) independently selected $C_{1-6}$ alkyl.

In some embodiments of Formula (I), $R^{8a}$ and $R^{8b}$ taken together with the carbon atom to which each is attached forms:

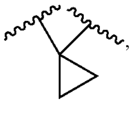, 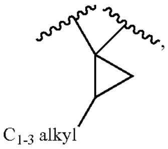, or 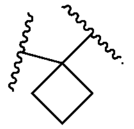.

In some embodiments of Formula (I), $R^{8a}$ and $R^{8b}$ taken together with the carbon atom to which each is attached forms:

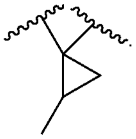.

In some embodiments of Formula (I), $R^9$ is:

(IX-2)

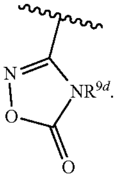.

In some embodiments, $R^{9d}$ is H or $C_{1-6}$ alkyl. For example, $R^{9d}$ can be H.

In some embodiments of Formula (I), the $L^3$-$C(R^{8a}R^{8b})$-$L^4$-$R^9$ moiety is:

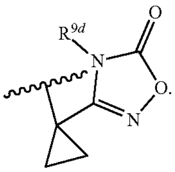.

In some embodiments of Formula (I), the $L^3$-$C(R^{8a}R^{8b})$-$L^4$-$R^9$ moiety is:

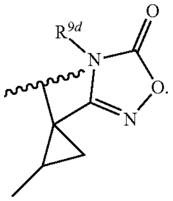.

In some embodiments of Formula (I), the $L^3$-$C(R^{8a}R^{8b})$-$L^4$-$R^9$ moiety is:

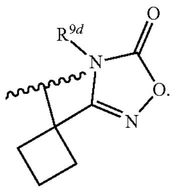.

In some embodiments of Formula (I), the $L^3$-$C(R^{8a}R^{8b})$-$L^4$-$R^9$ moiety is:

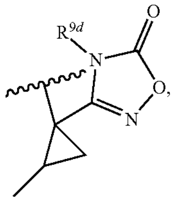, wherein each stereogenic center has (S)-configuration.

In some embodiments of Formula (I), $R^9$ is (IX-2), wherein the $L^3$-$C(R^{8a}R^{8b})$-$L^4$-$R^9$ moiety is:

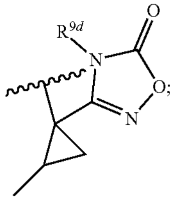;

wherein $R^{9d}$ is H or $C_{1-6}$ alkyl. For example, $R^{9d}$ can be H. In some embodiments, each stereogenic center of

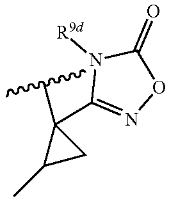

has (S)-configuration.

In some embodiments of Formula (I), $R^9$ is C(=O)OH.

In some embodiments of Formula (I), Ring C is 3-12 membered heterocyclyl which is optionally substituted with from 1-3 independently selected $R^{Ca}$. In some embodiments, Ring C is 4-8 membered heterocyclyl which is optionally substituted with from 1-3 independently selected $R^{Ca}$. In some embodiments, Ring C is 5-6 membered heterocyclyl which is optionally substituted with from 1-3 independently selected $R^{Ca}$. For example, Ring C can be tetrahydropyranyl which is optionally substituted with from 1-3 independently $R^{Ca}$.

In some embodiments of Formula (I), Ring C is selected from the group consisting of

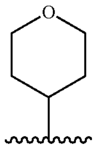

and

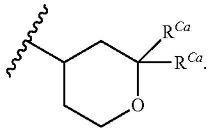

In some embodiments, Ring C is

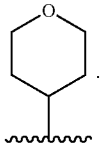

In some embodiments, Ring C is

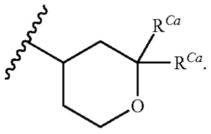

In some embodiments of Formula (I), $R^{Ca}$ is independently $C_{1-6}$ alkyl.

In some embodiments of Formula (I), a pair of $R^C$a on the same or different ring atoms, taken together with the ring atom(s) to which each is attached, forms a carbocyclic ring including from 3-6 ring atoms.

In some embodiments of Formula (I), a pair of $R^C$a on the same ring atom, taken together with the ring atom to which each is attached, forms a carbocyclic ring including from 3-5 ring atoms.

In some embodiments, the compound of Formula (I) is a compound of Formula (IA):

Formula (IA)

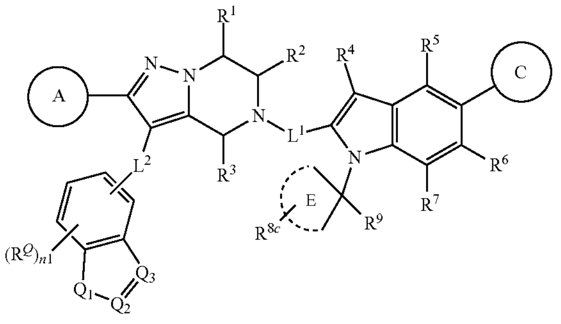

or a pharmaceutically acceptable salt or solvate thereof, wherein:

$Q^1$ is NH or NR;

$Q^2$ and $Q^3$ are each independently N, CH, or CR;

n1 is 0 or 1;

Ring E is a $C_{3-6}$ cycloalkyl; and $R^{8c}$ is selected from the group consisting of H and $C_{1-6}$ alkyl optionally substituted with from 1-3 independently selected $R^f$.

In some embodiments of Formula (IA), $Q^1$ is $NR^Q$.

In some embodiments of Formula (IA), the $R^Q$ attached to N is selected from the group consisting of:

(a) halo;

(b) cyano;

(c) OH;

(d) $-NR^cR^d$;

(e) $-C(=O)NR^cR^d$ or $-S(O)_2NR^cR^d$;

(f) $-S(=O)_{0-2}R^e$;

(g) $C_{1-6}$ alkyl optionally substituted with from 1-6 independently selected R; and (h) $C_{1-6}$ alkoxy optionally substituted with from 1-6 independently selected R.

As a non-limiting example, the $R^Q$ attached to N can be unsubstituted $C_{1-3}$ alkyl.

In some embodiments of Formula (IA), $Q^2$ and $Q^3$ are each independently N or CH. As a non-limiting example, $Q^2$ is N and $Q^3$ can be CH.

In some embodiments of Formula (IA), n1 is 0. In some embodiments of Formula (IA), n1 is 1.

In some embodiments of Formula (IA), the $R^Q$ attached to the 6-membered ring is selected from halo, cyano, OH, $C_{1-6}$ alkyl, and $C_{1-6}$ alkoxy. In some embodiments, the $R^Q$ attached to the 6-membered ring is halo.

In some embodiments of Formula (IA), $L^2$ attaches para to $Q^1$.

In some embodiments of Formula (IA), the $R^Q$ attached to the 6-membered ring is attached at the position ortho to $Q^3$.

In some embodiments, the compound of Formula (I) is a compound of Formula (IB):

Formula (IB)

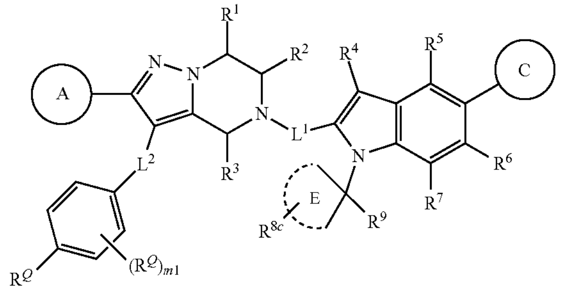

or a pharmaceutically acceptable salt or solvate thereof, wherein:

m1 is 0, 1, or 2;

the $R^Q$ para to $L^2$ is $-P(=O)R^aR^b$;

Ring E is a $C_{3-6}$ cycloalkyl; and $R^{8c}$ is selected from the group consisting of H and $C_{1-6}$ alkyl optionally substituted with from 1-3 independently selected $R^f$.

In some embodiments of Formula (IB), $R^a$ and $R^b$ are independently selected $C_{1-6}$ alkyl optionally substituted with from 1-2 substituents each independently selected from the group consisting of $C_{1-6}$ alkoxy, $C_{3-6}$ cycloalkyl, and halo. In some embodiments, $R^a$ and $R^b$ are independently selected unsubstituted $C_{1-3}$ alkyl.

In some embodiments of Formula (IB), m1 is 1 and the $R^Q$ that is not para to $L^2$ is meta to $L^2$. In some embodiments, the $R^Q$ that is meta to $L^2$ is $-NR^cR^d$.

In some embodiments of Formula (IB), each $R^c$ and $R^d$ are independently selected from the group consisting of: H, $C_{1-6}$ alkyl, $C(=O)(C_{1-6}$ alkyl), wherein the $C_{1-6}$ alkyl and $C(=O)(C_{1-6}$ alkyl) are each optionally substituted with from 1-6 substituents independently selected from the group consisting of: —OH, halo, and $C_{1-6}$ alkoxy. In some embodiments, one of R and $R^d$ is H, and the other of $R^c$ and $R^d$ is methyl.

In some embodiments of Formulae (IA) or (IB), Ring E is cyclopropyl.

In some embodiments of Formulae (IA) or (IB), Ring E is cyclobutyl.

In some embodiments of Formulae (IA) or (IB), $R^{8c}$ is H.

In some embodiments of Formulae (IA) or (IB), $R^{8c}$ is $C_{1-3}$ alkyl. For example, $R^{8c}$ can be methyl.

In some embodiments of Formulae (IA) or (IB), $R^9$ is:

(IX-2)

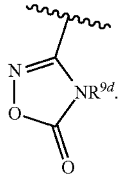

In some embodiments, $R^{9d}$ is H.

In some embodiments of Formulae (IA) or (IB), the

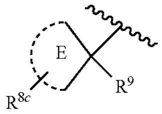

moiety is:

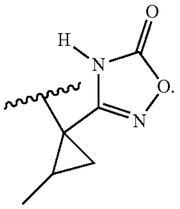 [SMILES: *C1(c2noc(=O)[nH]2)CC1C]

In some embodiments of Formulae (IA) or (IB), the

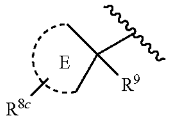

moiety is:

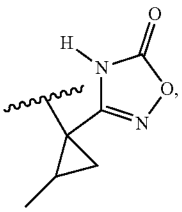 [SMILES: *C1(c2noc(=O)[nH]2)CC1C]

wherein each stereogenic center in has (S)-configuration.

In some embodiments of Formulae (IA) or (IB), the

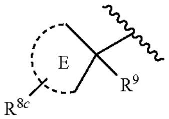

C moiety is:

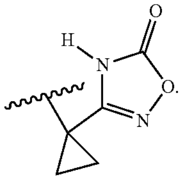 [SMILES: *C1(c2noc(=O)[nH]2)CC1]

In some embodiments of Formulae (IA) or (IB), the

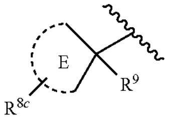

moiety is:

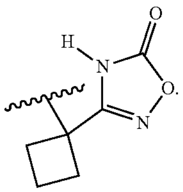 [SMILES: *C1(c2noc(=O)[nH]2)CCC1]

In some embodiments of Formulae (IA) or (IB), $R^9$ is C(=O)OH.

In some embodiments of Formulae (IA) or (IB), Ring C is 3-12 membered heterocyclyl which is optionally substituted with from 1-3 independently selected $R^{Ca}$.

In some embodiments of Formulae (IA) or (IB), Ring C is 5-6 membered heterocyclyl which is optionally substituted with from 1-3 independently selected $R^{Ca}$.

In some embodiments of Formulae (IA) or (IB), Ring C is tetrahydropyranyl which is optionally substituted with from 1-3 independently $R^{Ca}$.

In some embodiments of Formulae (IA) or (IB), Ring C is selected from the group consisting of

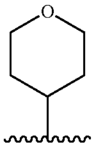

and

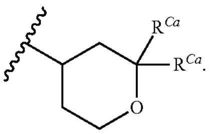

In some embodiments of Formulae (IA) or (IB), each $R^{Ca}$ is independently $C_{1-6}$ alkyl.

In some embodiments of Formulae (IA) or (IB), a pair of $R^{Ca}$ on the same or different ring atoms, taken together with the ring atom(s) to which each is attached, forms a carbocyclic ring including from 3-6 ring atoms.

In some embodiments of Formulae (IA) or (IB), $R^4$, $R^5$, $R^6$, and $R^7$ are each H.

In some embodiments of Formulae (IA) or (IB), $L^1$ is C(═O).

In some embodiments of Formulae (IA) or (IB), $R^1$ and $R^2$ are H.

In some embodiments of Formulae (IA) or (IB), $R^3$ is $C_{1-3}$ alkyl.

In some embodiments of Formulae (IA) or (IB), $R^3$ is methyl.

In some embodiments of Formulae (IA) or (IB), $R^1$ and $R^2$ are H; and $R^3$ is $C_{1-3}$ alkyl (e.g., methyl).

In some embodiments of Formulae (IA) or (IB), Ring A is phenyl or pyridyl, each of which is optionally substituted with from 2-4 substituents each independently selected from the group consisting of halo, $C_{1-6}$ alkyl, $C_{1-6}$ haloalkyl, and $C_{1-6}$ alkoxy.

In some embodiments of Formulae (IA) or (IB), Ring A is phenyl, which is optionally substituted with from 2-4 substituents each independently selected from the group consisting of halo and $C_{1-6}$ alkyl.

In some embodiments of Formulae (IA) or (IB), Ring A is:

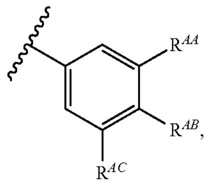

wherein $R^{AA}$, $R^{AB}$, and $R^{AC}$ are independently halo or $C_{1-6}$ alkyl. In some embodiments, $R^{AA}$ and $R^{AC}$ are independently $C_{1-6}$ alkyl. For example, $R^{AA}$ and $R^{AC}$ can be independently selected $C_{1-3}$ alkyl, such as methyl. In some embodiments, $R^{AB}$ is halo, such as —F.

In some embodiments of Formulae (IA) or (IB), $L^2$ is:

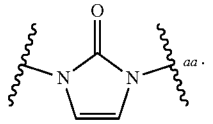 [SMILES: *n1ccn(*)c1=O]

In some embodiments, the compound of Formula I is selected from the group consisting of the compounds in Table C1 or a pharmaceutically acceptable salt or solvate thereof.

TABLE C1

| Compound No. | Structure |
|---|---|
| 101 | 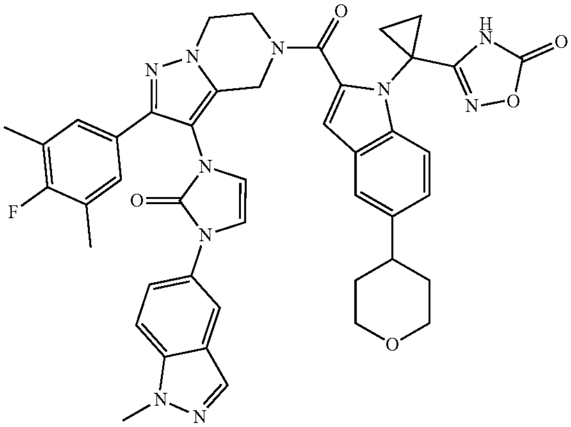 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CC2)CC3)cc(C)c1F] |
| 102 | 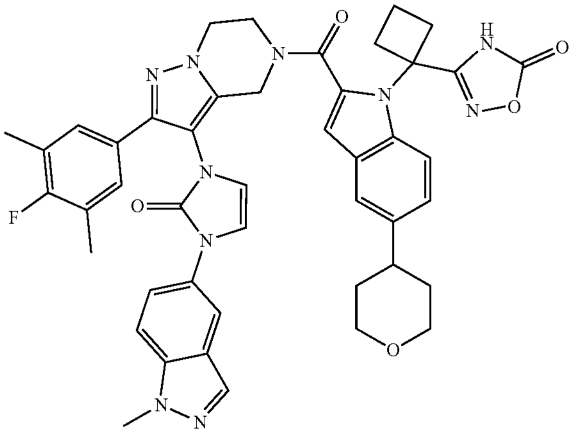 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CCC2)CC3)cc(C)c1F] |

TABLE C1-continued
| Compound No. | Structure |
|---|---|
| 103 | 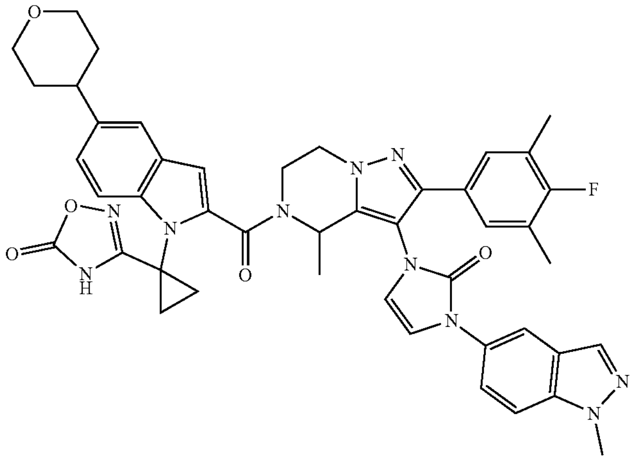 |
| 104 | 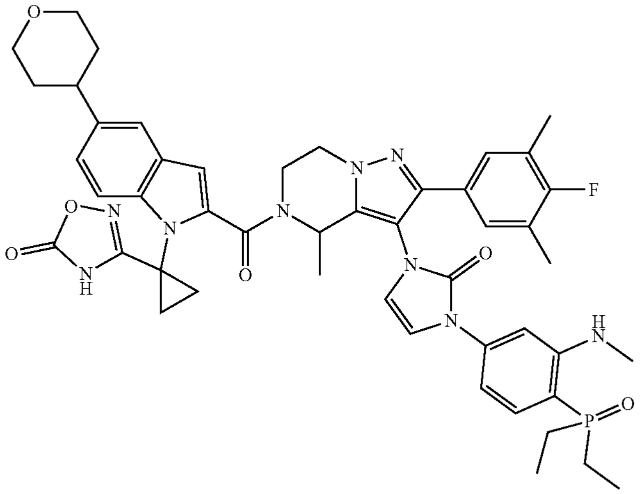 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3)CC4)c2=O)cc1NC] |
| 105 | 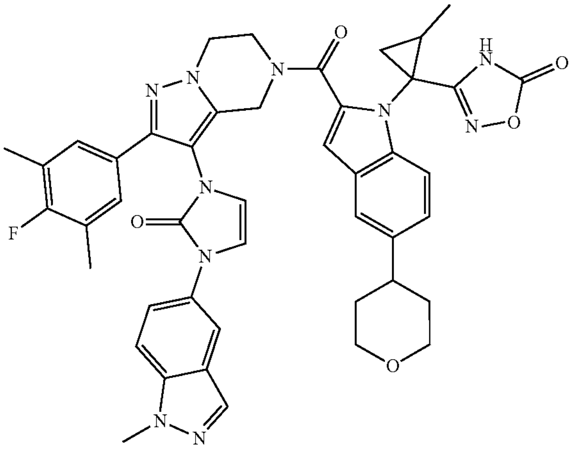 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CC2C)CC3)cc(C)c1F] |

TABLE C1-continued
| Compound No. | Structure |
| --- | --- |
| 106 | 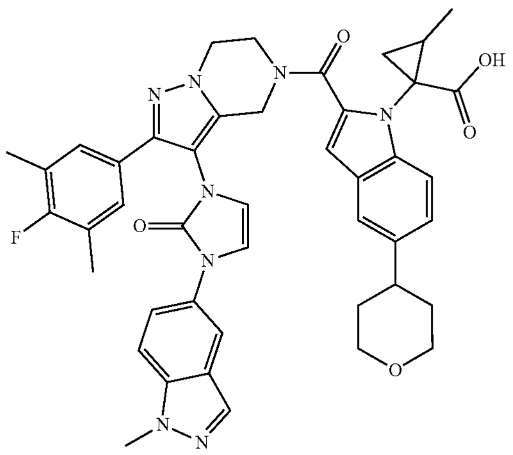 [SMILES: Cc1cc(-c2nn3c(c2-n2ccn(-c4ccc5c(cnn5C)c4)c2=O)CN(C(=O)c2cc4cc(C5CCOCC5)ccc4n2C2(C(=O)O)CC2C)CC3)cc(C)c1F] |
| 107 | 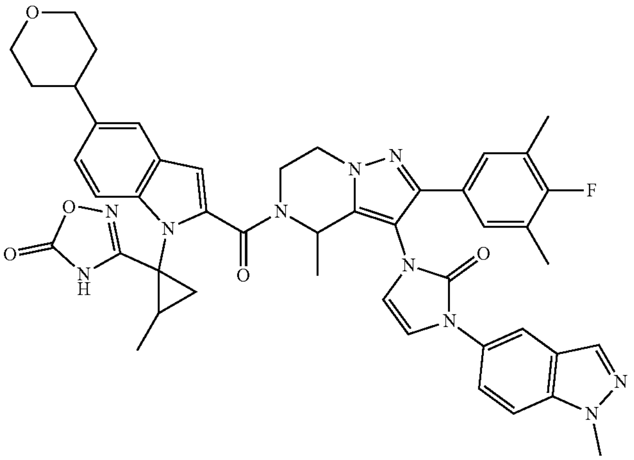 [SMILES: Cc1cc(-c2nn3c(c2-n2ccn(-c4ccc5c(cnn5C)c4)c2=O)C(C)N(C(=O)c2cc4cc(C5CCOCC5)ccc4n2C2(c4noc(=O)[nH]4)CC2C)CC3)cc(C)c1F] |
| 108 | 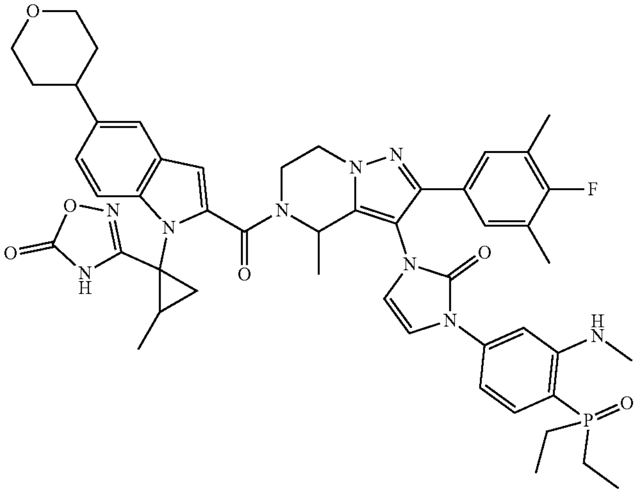 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)cc1NC] |

TABLE C1-continued
| Compound No. | Structure |
|---|---|
| 109/110 | 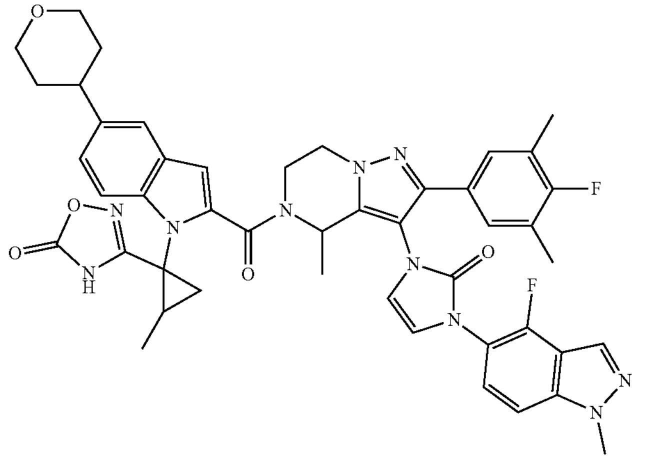 [SMILES: Cc1cc(-c2nn3c(c2-n2ccn(-c4ccc5c(cnn5C)c4F)c2=O)C(C)N(C(=O)c2cc4cc(C5CCOCC5)ccc4n2C2(c4noc(=O)[nH]4)CC2C)CC3)cc(C)c1F] |
| 111/112 | 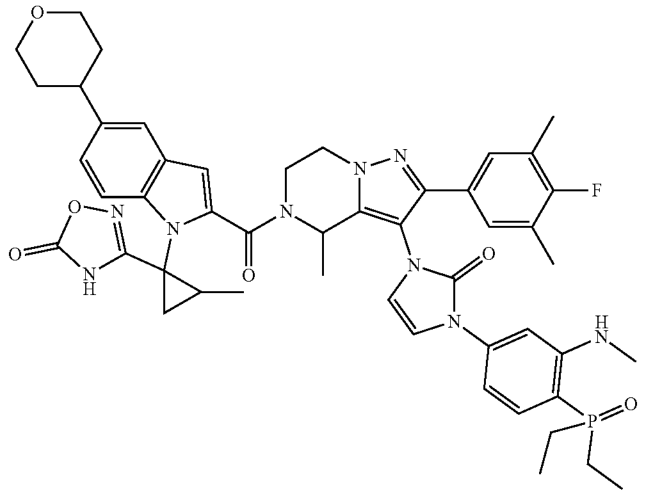 |
| 113 | 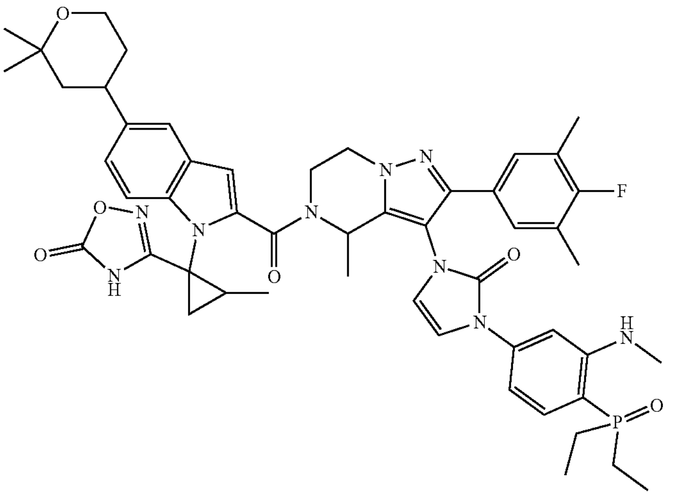 |

TABLE C1-continued
| Compound No. | Structure |
| --- | --- |
| 114 | 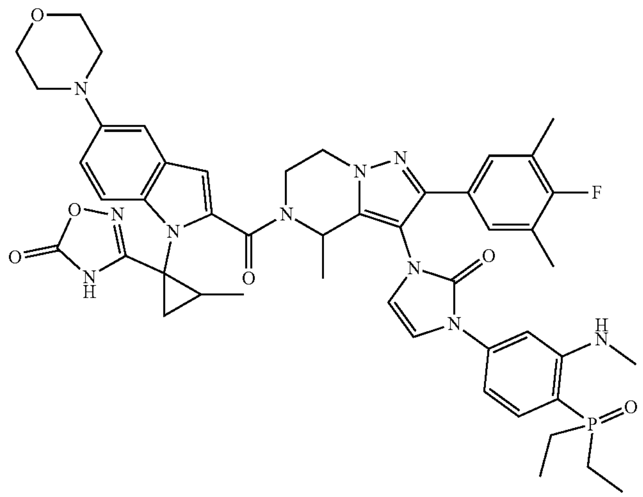 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)cc1NC] |
| 115 | 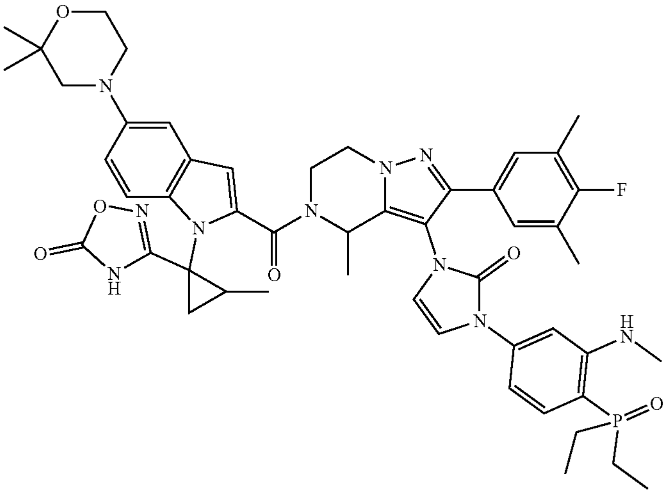 |
| 116 | 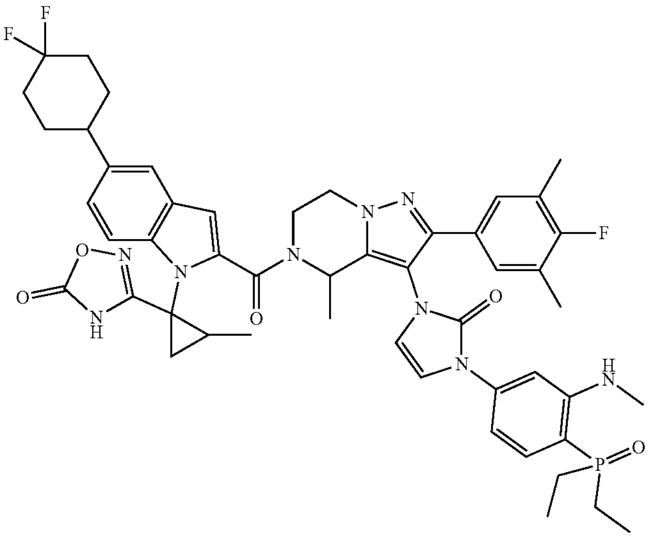 [SMILES: CCP(=O)(CC)c1ccc(-n2ccn(-c3c(-c4cc(C)c(F)c(C)c4)nn4c3C(C)N(C(=O)c3cc5cc(C6CCC(F)(F)CC6)ccc5n3C3(c5noc(=O)[nH]5)CC3C)CC4)c2=O)cc1NC] |

TABLE C1-continued
| Compound No. | Structure |
| --- | --- |
| 117 | 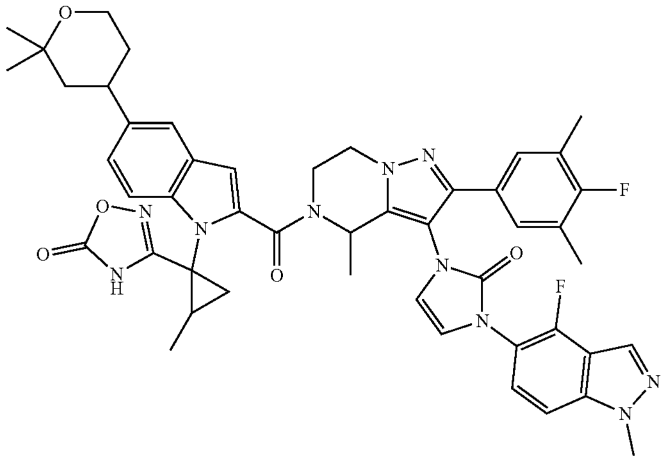 [SMILES: Cc1cc(-c2nn3c(c2-n2ccn(-c4ccc5c(cnn5C)c4F)c2=O)C(C)N(C(=O)c2cc4cc(C5CCOC(C)(C)C5)ccc4n2C2(c4noc(=O)[nH]4)CC2C)CC3)cc(C)c1F] |
| 118 | 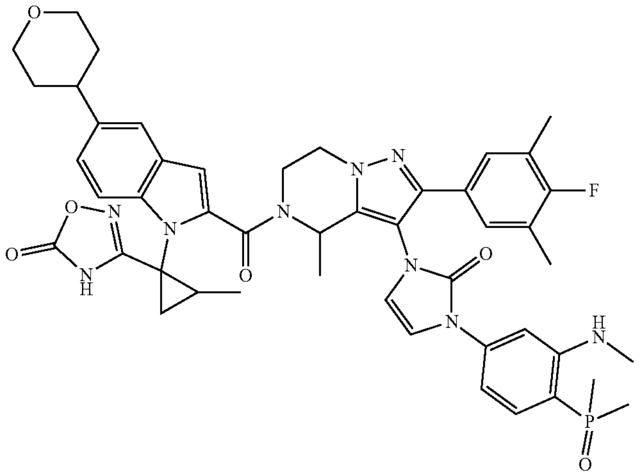 [SMILES: CNc1cc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)ccc1P(C)(C)=O] |
In some embodiments, the compound is selected from the group consisting of the compounds in Table C2 or a pharmaceutically acceptable salt or solvate thereof.
TABLE C2
| Compound No. | Structure |
| --- | --- |
| 105a | 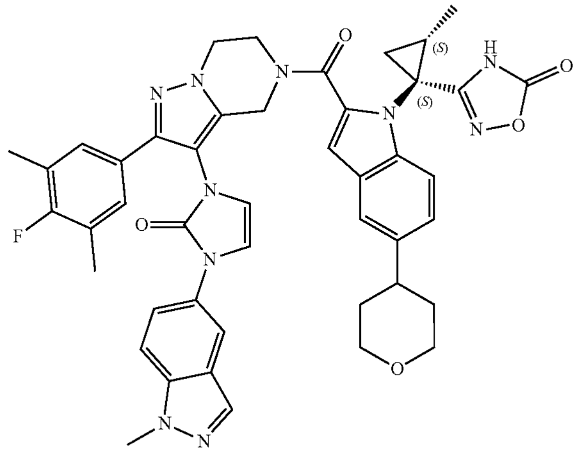 |

TABLE C2-continued
| Compound No. | Structure |
| --- | --- |
| 106a | 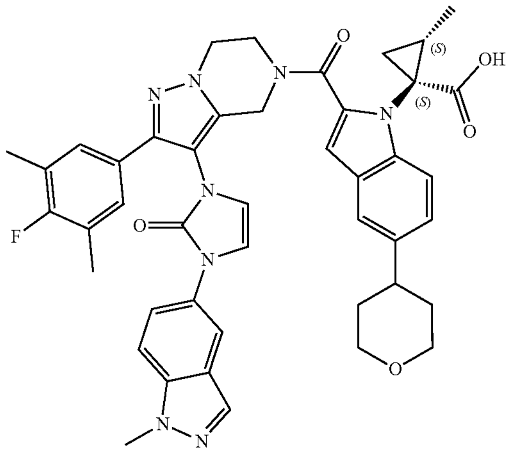 |
| 107a | 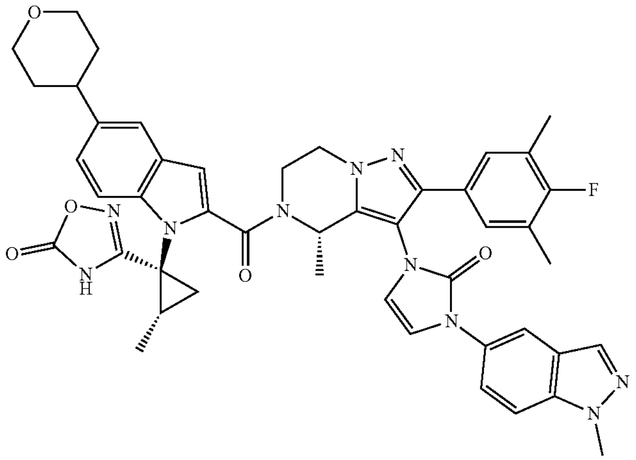 [SMILES: Cc1cc(-c2nn3c(c2-n2ccn(-c4ccc5c(cnn5C)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 108a | 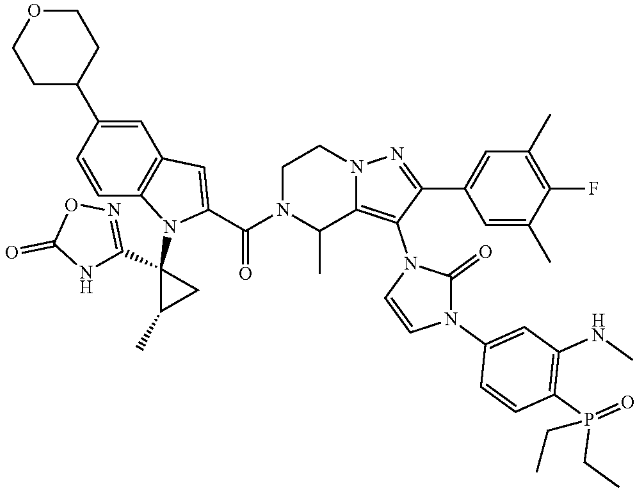 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3[C@@]3(c5noc(=O)[nH]5)C[C@@H]3C)CC4)c2=O)cc1NC] |

TABLE C2-continued
| Compound No. | Structure |
|---|---|
| 109a | 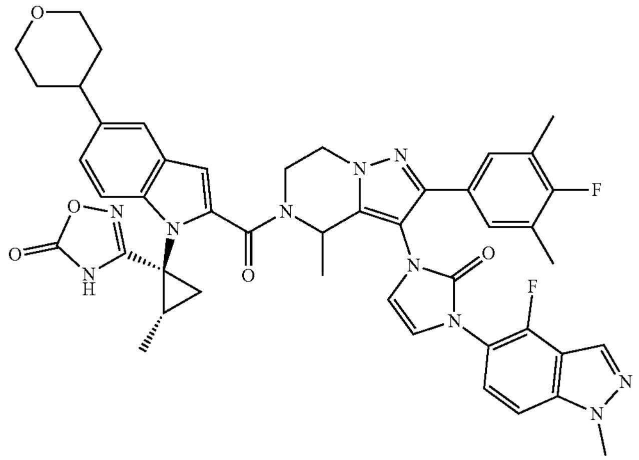 [SMILES: Cc1cc(-c2nn3c(c2-n2ccn(-c4ccc5c(cnn5C)c4F)c2=O)C(C)N(C(=O)c2cc4cc(C5CCOCC5)ccc4n2[C@@]2(c4noc(=O)[nH]4)C[C@@H]2C)CC3)cc(C)c1F] |
| 110a | 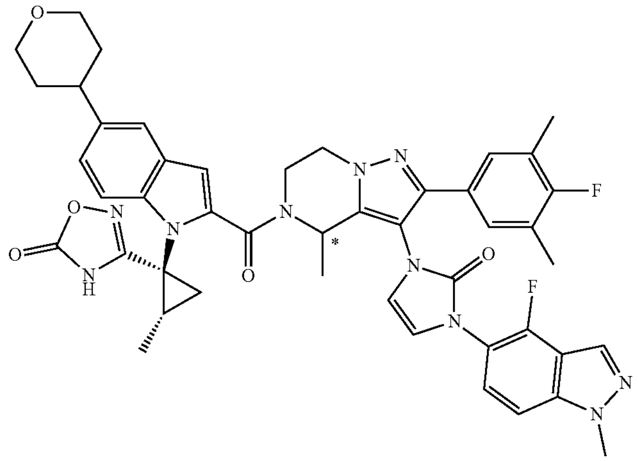 single diastereomer 2 |
| 111a | 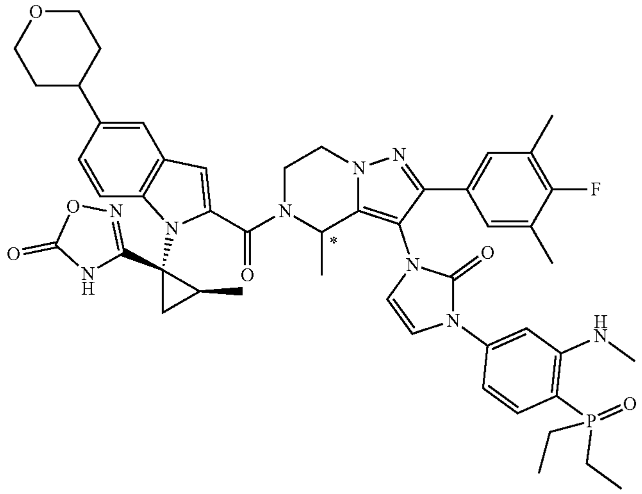 single diastereomer 2 |

TABLE C2-continued
| Compound No. | Structure |
|---|---|
| 112a | 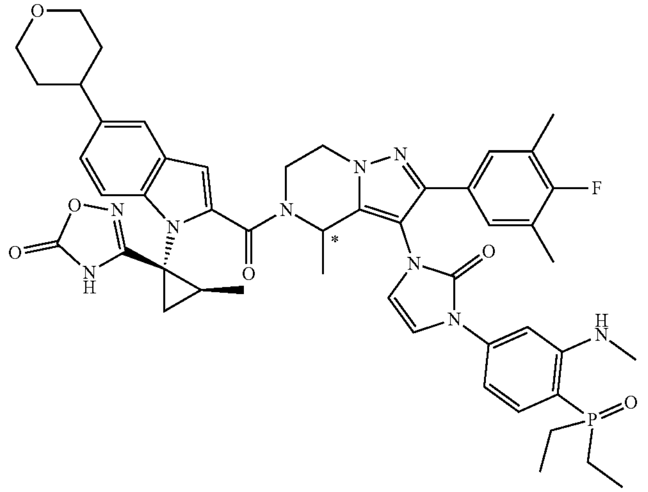 single diastereomer 1 |
| 113a | 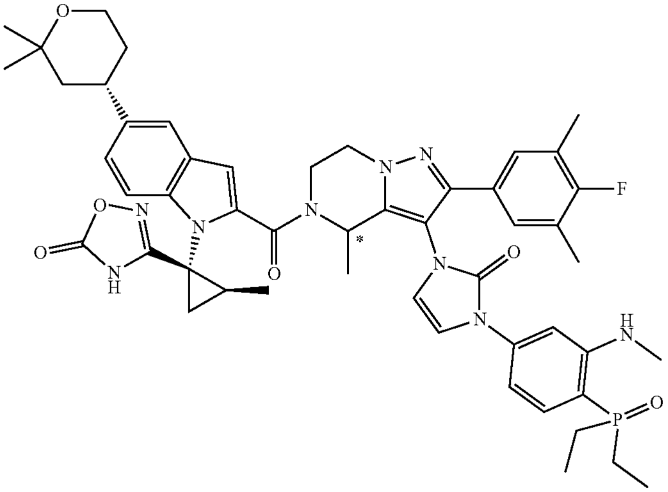 single diastereomer 2 |
| 114a | 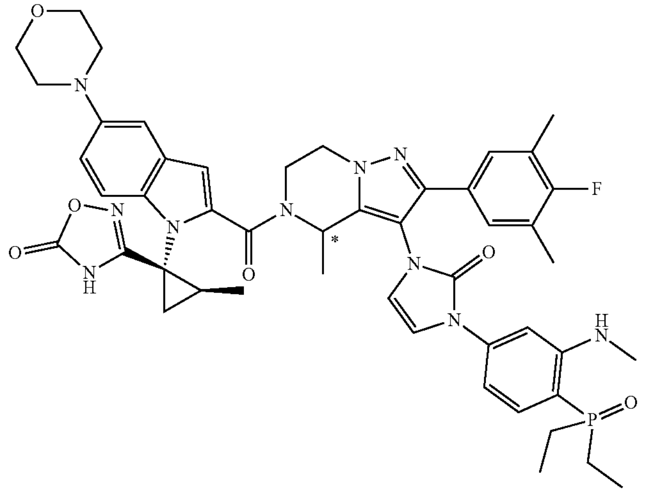 single diastereomer 2 |

TABLE C2-continued
| Compound No. | Structure |
| --- | --- |
| 115a | 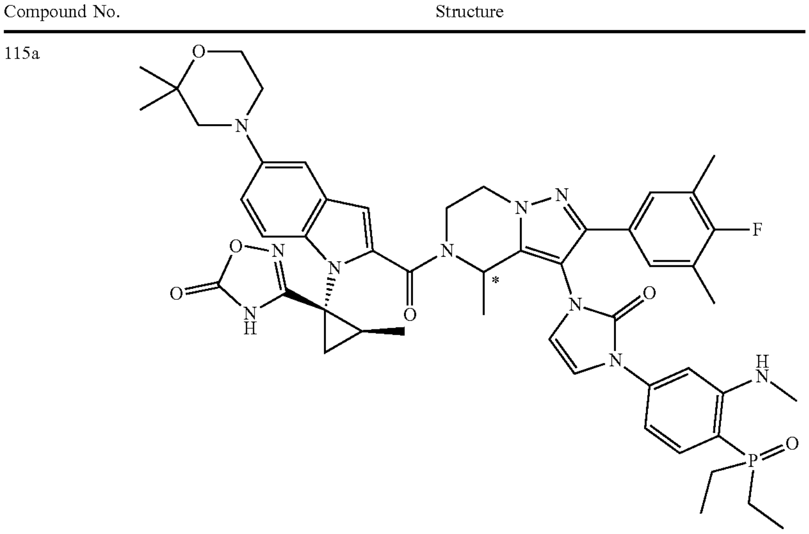 single diastereomer 2 |
| 116a | 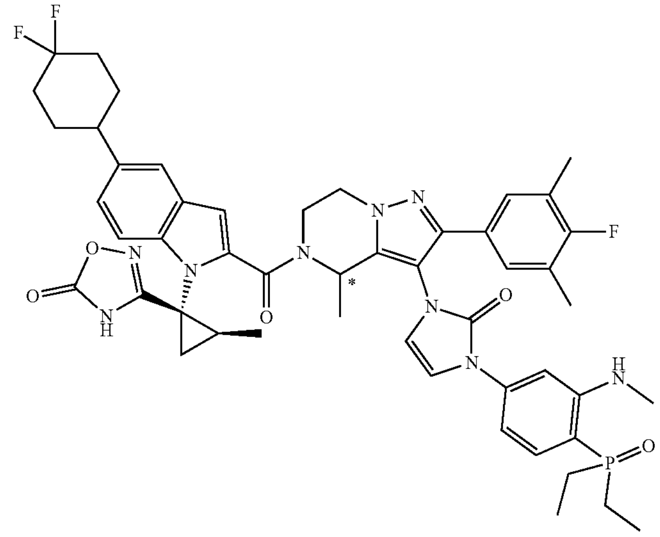 single diastereomer 2 |
| 117a | 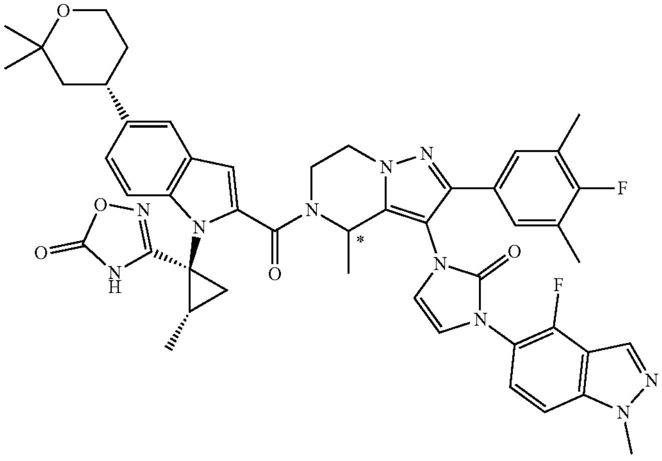 single diastereomer 2 |

TABLE C2-continued

| Compound No. | Structure |
| --- | --- |
| 118a | 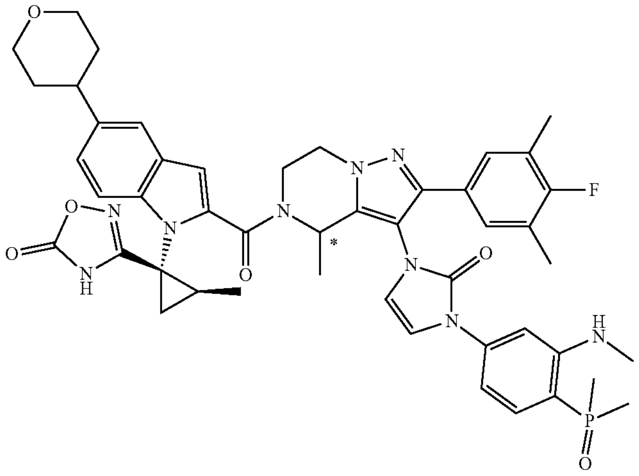 single diastereomer 2 |

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

Pharmaceutical Compositions and Administration

When employed as pharmaceuticals, the compounds of Formula I, including pharmaceutically acceptable salts or solvates thereof can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, or a pharmaceutically acceptable salt or solvate thereof, in combination with one or more pharmaceutically acceptable excipients (carriers). For example, a pharmaceutical composition prepared using a compound of Formula I, or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, or a pharmaceutically acceptable salt or solvate thereof with a pharmaceutically acceptable excipient. Pharmaceutical compositions containing a compound of Formula I, or a pharmaceutically acceptable salt or solvate thereof as the active ingredient can be prepared by intimately mixing the compound of Formula I, or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of*

*Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound of Formula I, or a pharmaceutically acceptable salt or solvate thereof (e.g., a compound of any one of Formulas IA and IB, or a pharmaceutically acceptable salt or solvate thereof) as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula I, or a pharmaceutically acceptable salt or solvate thereof (e.g., a compound of any one of Formulas IA and IB, or a pharmaceutically acceptable salt or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula I, or a pharmaceutically acceptable salt or solvate thereof (e.g., a compound of any one of Formulas IA and IB, or a pharmaceutically acceptable salt or solvate thereof) or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula I, or a pharmaceutically acceptable salt or solvate thereof (e.g., a compound of any one of Formulas IA and IB, or a pharmaceutically acceptable salt or solvate thereof) as described herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound of Formula I, or a pharmaceutically acceptable salt or solvate thereof (e.g., a compound of any one of Formulas IA and IB, or a pharmaceutically acceptable salt or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula I, or a pharmaceutically acceptable salt or solvate thereof (e.g., a compound of any one of Formulas IA and IB, or a pharmaceutically acceptable salt or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula I, or a pharmaceutically acceptable salt or solvate thereof (e.g., a compound of any one of Formulas IA and IB, or a pharmaceutically acceptable salt or solvate thereof) as described herein or a pharmaceutical composition thereof is formulated for ocular administration. In some embodiments, ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula I, or a pharmaceutically acceptable salt or solvate thereof (e.g., a compound of any one of Formulas IA and IB, or a pharmaceutically acceptable salt or solvate thereof) as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments, the dosage for a compound of Formula I, or a pharmaceutically acceptable salt or solvate thereof (e.g., a compound of any one of Formulas IA and IB, or a pharmaceutically acceptable salt or solvate thereof), is determined based on a multiple factors including, but not limited to, type, age, weight, sex, medical condition of the patient, severity of the medical condition of the patient, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula I, or a pharmaceutically acceptable salt or solvate thereof (e.g., a compound of any one of Formulas IA and IB, or a pharmaceutically acceptable salt or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula I, or a pharmaceutically acceptable salt or solvate thereof (e.g., a compound of any one of Formulas IA and IB, or a pharmaceutically acceptable salt or solvate thereof) as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula I, or a pharmaceutically acceptable salt or solvate thereof (e.g., a compound of any one of Formulas IA and IB, or a pharmaceutically acceptable salt or solvate thereof) as described herein is administered as a dosage of about 100 mg/Kg.

In some embodiments, the foregoing dosages of a compound of Formula I, or a pharmaceutically acceptable salt or solvate thereof (e.g., a compound of any one of Formulas IA and IB, or a pharmaceutically acceptable salt or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula I, or a pharmaceutically acceptable salt or solvate thereof (e.g., a compound of any one of Formulas IA and IB, or a pharmaceutically acceptable salt or solvate thereof) as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula I, or a pharmaceutically acceptable salt or solvate thereof (e.g., a compound of any one of Formulas IA and IB, or a pharmaceutically acceptable salt or solvate thereof) is administered to a patient for a period of time followed by a separate period of time where administration of the compound of Formula I, or a pharmaceutically acceptable salt or solvate thereof (e.g., a compound of any one of Formulas IA and IB, or a pharmaceutically acceptable salt or solvate thereof) is stopped. In some embodiments, a compound of Formula I, or a pharmaceutically acceptable salt or solvate thereof (e.g., a compound of any one of Formulas IA and IB, or a pharmaceutically acceptable salt or solvate thereof) is administered for a first period and a second period following the first period, with administration stopped during the second period, followed by a third period where administration of the compound of Formula I, or a pharmaceutically acceptable salt or solvate thereof (e.g., a compound of any one of Formulas IA and IB, or a pharmaceutically acceptable salt or solvate thereof) is started and then a fourth period following the third period where administration is stopped. For example, the period of administration of a compound of Formula I, or a pharmaceutically acceptable salt or solvate thereof (e.g., a compound of any one of Formulas IA and IB, or a pharmaceutically acceptable salt or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound of Formula I, or a pharmaceutically acceptable salt or solvate thereof (e.g., a compound of any one of Formulas IA and IB, or a pharmaceutically acceptable salt or solvate thereof), is orally administered to the patient one or more times per day (e.g., one time per day, two times per day, three times per day, four times per day per day or a single daily dose).

In some embodiments, a compound of Formula I, or a pharmaceutically acceptable salt or solvate thereof (e.g., a compound of any one of Formulas IA and IB, or a pharmaceutically acceptable salt or solvate thereof), is administered by parenteral administration to the patient one or more times per day (e.g., 1 to 4 times one time per day, two times per day, three times per day, four times per day or a single daily dose).

In some embodiments, a compound of Formula I, or a pharmaceutically acceptable salt or solvate thereof (e.g., a compound of any one of Formulas IA and IB, or a pharmaceutically acceptable salt or solvate thereof), is administered by parenteral administration to the patient weekly.

Methods of Treatment

In some embodiments, this disclosure features methods for treating a patient (e.g., a human) having a disease, disorder, or condition in which modulation of GLP-1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt or solvate thereof (e.g., a compound of any one of Formulas IA and IB, or a pharmaceutically acceptable salt or solvate thereof), or a pharmaceutical composition as disclosed herein.

In some embodiments, the disease, disorder, or condition includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of blood glucose reduction (e.g., reduce blood glucose levels), reduce blood hemoglobin A1c (HbA1c) levels, promote insulin synthesis, stimulate insulin secretion, increase the mass of β-cells, modulate gastric acid secretion, modulate gastric emptying, decrease the body mass index (BMI), and/or decrease glucagon production (e.g., level). In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt or solvate thereof (e.g., a compound of any one of Formulas IA and IB, or a pharmaceutically acceptable salt or solvate thereof), or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt or solvate thereof (e.g., a compound of any one of Formulas IA and IB, or a pharmaceutically acceptable salt or solvate thereof), or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or (3-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt or solvate thereof (e.g., a compound of any one of a compound of any one of Formulas IA and IB, or a pharmaceutically acceptable salt or solvate thereof, or a pharmaceutically acceptable salt or solvate thereof) or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt or solvate thereof (e.g., a compound of any one of a compound of any one of Formulas IA and IB, or a pharmaceutically acceptable salt or solvate thereof, or a pharmaceutically acceptable salt or solvate thereof), or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt or solvate thereof (e.g., a compound of any one of a compound of any one of Formulas IA and IB, or a pharmaceutically acceptable salt or solvate thereof, or a pharmaceutically acceptable salt or solvate thereof), or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are also useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., *J Hepatol* 2001; 35: 195-9; Chitturi et al., *Hepatology* 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., *J Gastroenterol Hepatol* 2002; 17 Suppl:S186-90). In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

Other non-limiting examples of disorders in metabolically important tissues include joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., US20060275288A1.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., US20120021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., US20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking.

In some embodiments, the condition, disease or disorder is an eating disorder, such as hyperphagia, binge eating, bulimia, or compulsive eating.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the condition, disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the condition, disease or disorder associated with diabetes is related to the hypothalamic-pituitary-gonadal axis.

Pulmonary Disease

In some embodiments, the condition, disease or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the condition, disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of X, or a pharmaceutically acceptable salt or solvate thereof as described herein can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, therapeutic agents for dysuria and anti-emetic agents.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin), NFK inhibitors (e.g., HE-3286), PPAR agonists (e.g., GFT-505, DRF-11605, gemfibrozil and fenofibrate), phosphotyrosine phosphatase inhibitors (e.g., sodium vanadate, trodusquemin), GPR119 agonists (e.g., PSN-821, MBX-2982, APD597), glucokinase activators (e.g., piragliatin, AZD-1656, AZD6370, TTP-355, compounds described in W0006/112549, W0007/028135, W0008/047821, W0008/050821, W0008/136428 and W0008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), farnesoid X receptor (FXR) agonist, phentermine, zonisamide, norepinephrine/dopamine reuptake inhibitor, GDF-15 analog, methionine aminopeptidase 2 (MetAP2) inhibitor, diethylpropion, phendimetrazine, benzphetamine, fibroblast growth factor receptor (FGFR) modulator, and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, gliclazide, glimepiride, tolbutamide, glibenclamide, gliclazide, acetohexamide, glyclopyramide, glybuzole, glyburide), thiazolidinedione agents (e.g. rosiglitazone or pioglitazone), α-glucosidase inhibitors (e.g., voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, for example, for treating NAFL and NASH. Non-limiting examples include FXR agonists, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21), a niacin analogue, a leukotriene D4 (LTD4) receptor antagonist, an afcetyl-CoA carboxylase (ACC) inhibitor, a ketohexokinase (KHK) inhibitor, an apoptosis signal-regulating kinase 1 (ASK1) inhibitor, an ileal bile acid transporter (IBAT) inhibitor, glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and_apoptosis signal regulating kinase-1 (ASK-1) inhibitors.

In some embodiments, the one or more additional therapeutic agents include those useful, for example, for treating hyperlipidemia. Non-limiting examples include_HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and ω-3 fatty acid preparations (e.g., ω-3-fatty acid ethyl esters 90).

In some embodiments, the one or more additional therapeutic agents include those useful, for example, as anti-hypertensive agents. Non-limiting examples include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and_β-blockers (e.g., metoprolol, atenolol, propranolol, carvedilol, pindolol).

In some embodiments, the one or more additional therapeutic agents include those useful, for example, as diuretics. Non-limiting examples include_xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as antithrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran) FXa inhibitors (e.g., rivaroxaban, apixaban, edoxaban, YM150, compounds described in WO02/06234, WO2004/048363, WO2005/030740, WO2005/058823, and WO2005/113504) thrombolytic agents (e.g., urokinase, tisokinase, alteplase, nateplase, monteplase, pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-CoA reductase inhibitors (statins, e.g. rosuvastatin), cholesterol-lowering agents, bile acid sequestrants (e.g., cholestyramine), cholesterol absorption inhibitors (e.g. plant sterols such as phytosterols), cholesteryl ester transfer protein (CETP) inhibitors, inhibitors of the ileal bile acid transport system (IBAT inhibitors), bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone), centrally acting adrenergic drugs, such as central alpha agonists (e.g. clonidine), diuretic agents (e.g. furosemide), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin)), adenosine diphosphate (ADP) receptor inhibitors (e.g. clopidogrel), phosphodiesterase inhibitors (e.g. cilostazol), glycoprotein IIB/IIA inhibitors (e.g. tirofiban), adenosine reuptake inhibitors (e.g. dipyridamole), noradrenergic agents (e.g. phentermine), serotonergic agents (e.g. sibutramine), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in W0007/013694, WO2007/018314, WO2008/093639 and WO2008/099794, GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor α (PPARα), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., mexiletine), acetylcholine receptor ligands (e.g., ABT-594), endothelin receptor antagonists (e.g., ABT-627), narcotic analgesics (e.g., morphine), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-β), immunomodulators (e.g., glatiramer), TNF-binding proteins (e.g., circulating receptors), immunosupressants (e.g., mycophenolate), and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide.

In some embodiments, the one or more additional therapeutic agents include those useful, for example, as anti-emetic agents. As used herein, an "anti-emetic" agent refers to any agent that counteracts (e.g., reduces or removes) nausea or emesis (vomiting). While not wishing to be bound by theory, it is believed that administering one or more anti-emetic agents in combination with the formula (I) compounds described herein may allow higher dosages of the formula (I) compounds to be administered, e.g., because the patient may be able to have a normal food intake and thereby respond faster to the treatment.

Non-limiting examples of anti-emetic agents include 5HT3-receptor antagonists (serotonin receptor antagonists), neuroleptics/anti-psychotics, antihistamines, anticholinergic agents, steroids (e.g., corticosteroids), NK1-receptor antagonists (e.g., Neurokinin 1 substance P receptor antagonists), antidopaminergic agents/dopamine receptor antagonists, benzodiazepines, cannabinoids.

For example, the antiemetic agent can be selected from the group consisting of, neuroleptics, antihistamines, anticholinergic agents, steroids, 5HT-3-receptor antagonists, NK1-receptor antagonists, anti-dopaminergic agents/dopamine receptor antagonists, benzodiazepines and non-psychoactive cannabinoids.

In some embodiments, the anti-emetic agent is a 5HT3-receptor antagonist (serotonin receptor antagonist). Non-limiting examples of 5HT3-receptor antagonists (serotonin receptor antagonists) include: Granisetron (Kytril), Dolasetron, Ondansetron (Zofran), Tropisetron, Ramosetron, Palonosetron, Alosetron, azasetron, Bemesetron, Zatisetron, Batanopirde, MDL-73147EF; Metoclopramide, N-3389 (endo-3,9-dimethyl-3,9-diazabicyclo[3,3,1]non-7-yl-1H-indazole-3-carboxamide dihydrochloride), Y-25130 hydrochloride, MDL 72222, Tropanyl-3,5-dimethylbenzoate, 3-(4-Allylpiperazin-1-yl)-2-quinoxalinecarbonitrile maleate, Zacopride hydrochloride, and Mirtazepine. Other non-limiting examples of 5HT3-receptor antagonists (serotonin receptor antagonists) include: cilansetron, clozapine, cyproheptadine, dazopride, hydroxyzine, lerisetron, metoclopramide, mianserin, olanzapine, palonosetron (+netupitant), quetiapine, qamosetron, ramosteron, ricasetron, risperidone, ziprasidone, and zatosetron.

In certain embodiments, the 5HT-3-receptor antagonist is Granisetron, Dolasetron, Ondansetron hydrochloride, Tropisetron, Ramosetron, Palonosetron, Alosetron, Bemesetron, Zatisetron, Batanopirde, MDL-73147EF, Metoclopramide, N-3389, Y-25130 hydrochloride, MDL 72222, Tropanyl-3, 5-dimethylbenzoate 3-(4-AIlyI-piperazin-1-yl)-2-quinoxalinecarbonitrile maleate, Zacopride hydrochloride and Mirtazepine.

In certain embodiments, the 5HT-3-receptor antagonist is Granisetron, Dolasetron, Ondansetron hydrochloride, Tropisetron, Ramosetron, Palonosetron, Alosetron, Bemesetron, and Zatisetron.

In certain embodiments, the 5HT-3-receptor antagonist is Granisetron, Dolasetron and Ondansetron.

In certain embodiments, the 5HT-3-receptor antagonist is Granisetron.

In certain embodiments, the 5HT-3-receptor antagonist is Ondansetron.

In some embodiments, the anti-emetic agent is an antihistamine. Non-limiting examples of antihistamines include: piperazine derivatives (e.g., cyclizine, meclizine, and cinnarizine); Promethazine; Dimenhydrinate (Dramamine, Gravol); Diphenhydramine; Hydroxyzine; Buclizine; and Meclizine hydrochloride (Bonine, Antivert), doxylamine, and mirtazapine.

In some embodiments, the anti-emetic agent is an anticholinergic agent (Inhibitors of the acetylcholine receptors). Non-limiting examples of anticholinergic agents include: atropine, Scopolamine, Glycopyrron, Hyoscine, Artane (Trihexy-5 trihexyphenidyl hydrochloride), Cogentin (benztropine mesylate), Akineton (biperiden hydrochloride), Disipal (Norflex orphenadrine citrate), diphenhydramine, hydroxyzine, hyoscyamine, and Kemadrin (procyclidine hydrochloride).

In some embodiments, the anti-emetic agent is a steroid (e.g., a corticosteroid). Non-limiting examples of steroids include: betamethasone, Dexamethasone, Methylprednisolone, Prednisone®, and Trimethobenzamide (Tigan).

In some embodiments, the anti-emetic agent is an NK1-receptor antagonists (e.g., Neurokinin 1 substance P receptor antagonists). Non-limiting examples of NK1-receptor antagonists include: aprepitant, casopitant, ezlopitant, fosaprepitant, maropitant, netupitant, rolapitant, and vestipitant.

Other non-limiting examples of NK1-receptor antagonists include: MPC-4505, GW597599, MPC-4505, GR205171, L-759274, SR 140333, CP-96,345, BIIF 1149, NKP 608C, NKP 608A, CGP 60829, SR 140333 (Nolpitantium besilate/chloride), LY 303870 (Lanepitant), MDL-105172A, MDL-103896, MEN-11149, MEN-11467, DNK 333A, YM-49244, YM-44778, ZM-274773, MEN-10930, S-19752, Neuronorm, YM-35375, DA-5018, MK-869, L-754030, CJ-11974, L-758298, DNK-33A, 6b-1, CJ-11974 j. Benserazide and carbidopa k. TAK-637 [(aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6,13-dione], PD 154075, ([(2-benzofuran)-CH2OCO]—(R)-alpha-MeTrp-(S)—NHCH(CH3) Ph), FK888, and (D-Pro4, D-Trp7,9,10, Phe11)SP4-11.

In some embodiments, the anti-emetic agent is an anti-dopaminergic agents/dopamine receptor antagonist (e.g., dopamine receptor antagonist, e.g., D2 or D3 antagonists). Non-limiting examples include phenothiazines (e.g., promethazine, chlorpromazine, prochlorperazine, perphenazine, hydroxyzine, thiethylperazine, metopimazine,); benzamides (e.g., Metoclopramide, domperidone), butyrophenones (e.g., haloperidol, droperidol); alizapride, bromopride, clebopride, domperidone, itopride, metoclopramide, trimethobenzamide, and amisulpride.

In some embodiments, the anti-emetic agent is a non-psychoactive cannabinoids (e.g., Cannabidiol (CBD), Cannabidiol dimethylheptyl (CBD-DMH), Tetra-hydro-cannabinol (THC), Cannabinoid agonists such as WIN 55-212 (a CB1 and CB2 receptor agonist), Dronabinol (Marinol®), and Nabilone (Cesamet)).

Other exemplary anti-emetic agents include: c-9280 (Merck); benzodiazepines (diazepam, midazolam, lorazepam); neuroleptics/anti-psychotics (e.g., dixyrazine, haloperidol, and Prochlorperazine (Compazine®)); cerium oxalate; propofol; sodium citrate; dextrose; fructose (Nauzene); orthophosphoric acid; fructose; glucose (Emetrol); bismuth subsalicylate (Pepto Bismol); ephedrine; vitamin B6; peppermint, lavender, and lemon essential oils; and ginger.

Still other exemplary anti-emetic agents include those disclosed in US 20120101089A1; U.S. Pat. No. 10,071,088 B2; U.S. Pat. No. 6,673,792 B1; U.S. Pat. No. 6,197,329 B1; U.S. Pat. No. 10,828,297 B2; U.S. Pat. No. 10,322,106 B2; U.S. Pat. No. 10,525,033 B2; WO 2009080351 A1; WO 2019203753 A2; WO 2002020001 A2; U.S. Pat. No. 8,119,697 B2; U.S. Pat. No. 5,039,528; US20090305964A1; and WO 2006/111169, each of which is incorporated by reference in its entirety.

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

Patient Selection

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin A1c (HbA1c), fasting plasma glucose, non-fasting plasma glucose, or any combination thereof. In some embodiments, the level of HbA1c is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 $kg/m^2$ to greater than or about 100 $kg/m^2$. In some embodiments, the BMI of the patient is greater than or about 30 $kg/m^2$ to greater than or about 90 $kg/m^2$. In some embodiments, the BMI of the patient is greater than or about 40 $kg/m^2$ to greater than or about 80 $kg/m^2$. In some embodiments, the BMI of the patient is greater than or about 50 $kg/m^2$ to greater than or about 70 $kg/m^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

EXAMPLES

The invention is further described in the following examples, which do not limit the scope of the invention described in the claims.

Example 1

3-((1S,2S)-1-(2-(2-(4-fluoro-3,5-dimethylphenyl)-3-(3-(1-methyl-1H-indazol-5-yl)-2-oxo-2,3-dihydro-1H-imidazol-1-yl)-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (Compound 105a)

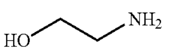
1

$(Boc)_2O$, NaOH
$H_2O$, THF
Step A

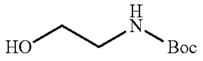
2

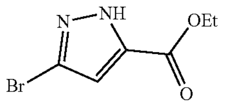
3

$PPh_3$, DEAD
THF
Step B

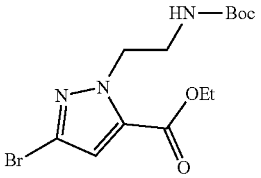
4

HCl/dioxane
dioxane
Step C

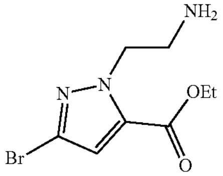
5

TEA
EtOH
Step D

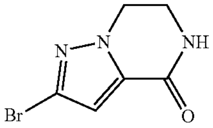
6

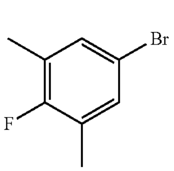
7

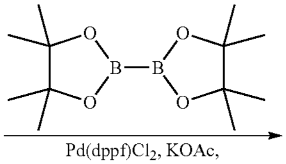

$Pd(dppf)Cl_2$, KOAc,
dioxane
Step E

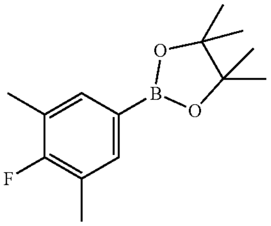
8

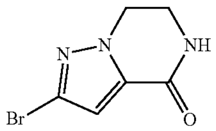
6

$K_2CO_3$, $Pd(dppf)Cl_2$
dioxane/$H_2O$
Step F

-continued

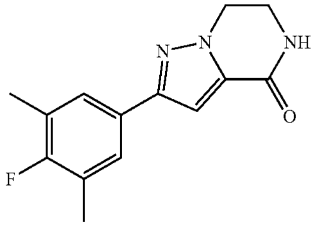
9

LAH
THF
Step G

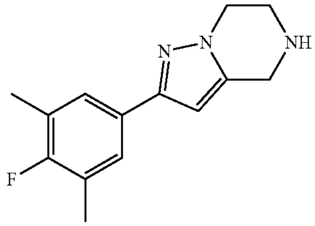
10

$Boc_2O$, TEA
DCM
Step H

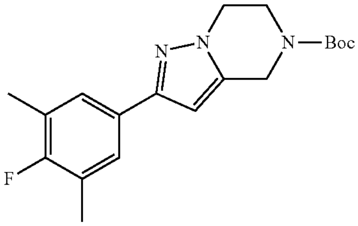
11

NBS
MeCN
Step I

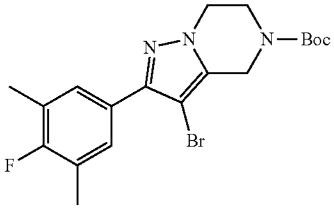
12

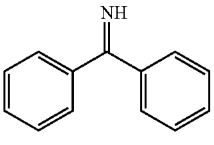
13

$Pd_2(dba)_3$, XantPhos,
t-BuONa, dioxane
Step J

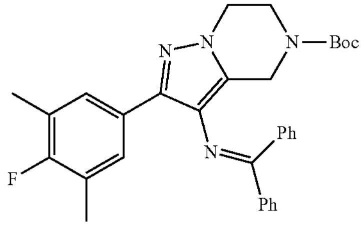
14

$NH_2OH$ HCl,
AcONa
MeOH
Step K

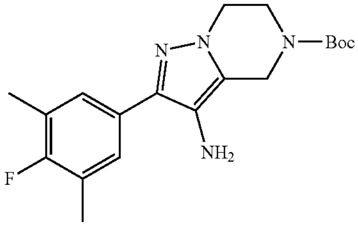
15

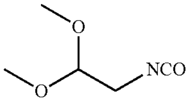
16 pyridine
Step M

-continued
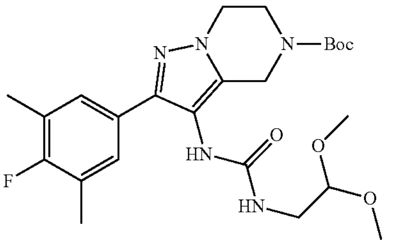
17
MeSO3H
THF
Step N
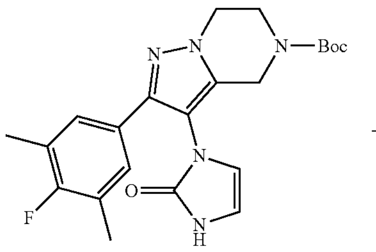
18
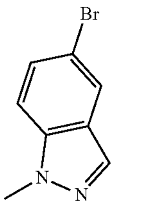
19
CuI, $K_2CO_3$,
NMP
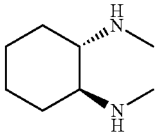
Step O
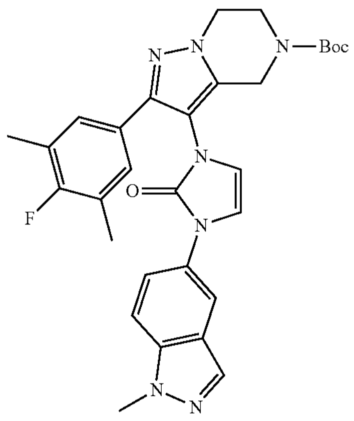
20
HCl/dioxane
EtOAc
Step P
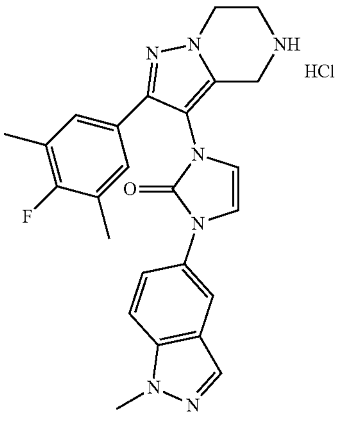
21
-continued
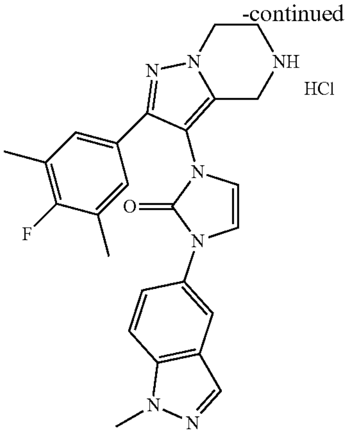
21
+
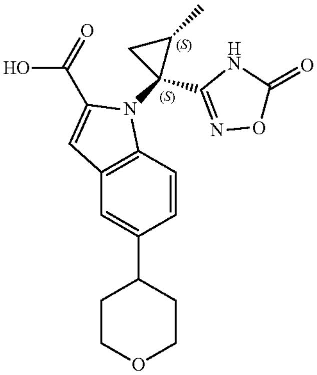
22
$T_3P$, TEA
THF
Step Q
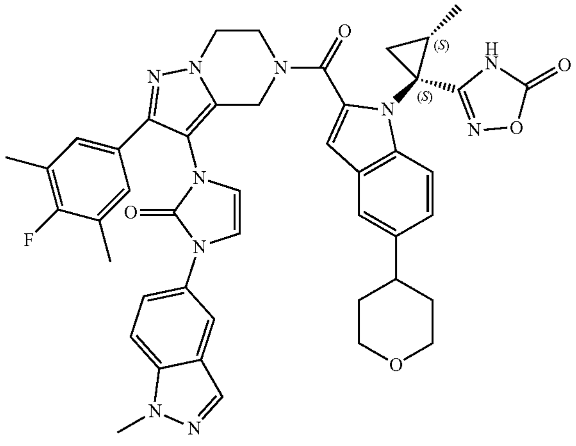
105a
Step A: tert-Butyl N-(2-hydroxyethyl)carbamate
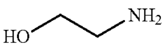
1
$(Boc)_2O$, NaOH
$H_2O$, THF
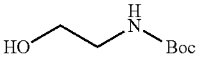
2
To a solution of 2-aminoethanol (5.00 g, 4.95 mL) in $H_2O$ (30 mL) was added NaOH (327.4 mg) and a solution of $(Boc)_2O$ (19.65 g, 20.69 mL) in THF (30 mL) dropwise. The yellow mixture was stirred at 25° C. for 17 hrs. The yellow mixture was extracted with ethyl acetate (30 mL) for three times. The organic layer was washed with brine (60 mL), dried by $Na_2SO_4$, and filtered. The filtrate was concentrated to give crude (18.60 g) as a yellow oil. The crude was purified by Combi-flash (silica gel, ethyl acetate in petrol ether from 20~80%) to give tert-butyl N-(2-hydroxyethyl) carbamate (12.10 g, 91.7% yield) as a colorless oil.

$^1H$ NMR (400 MHz, CDCl3) δ ppm 4.96 (br s, 1H) 3.67-3.75 (m, 2H) 3.27-3.32 (m, 2H) 2.43 (br s, 1H) 1.45 (s, 9H)

Step B: Ethyl 5-bromo-2-[2-(tert-butoxycarbonylamino)ethyl]pyrazole-3-carboxylate

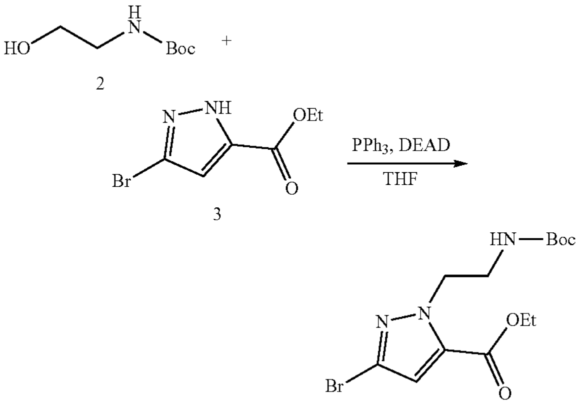

2
3
4

To a solution of ethyl 3-bromo-1H-pyrazole-5-carboxylate (4.00 g, 18.26 mmol) and tert-butyl N-(2-hydroxyethyl) carbamate (2.94 g, 18.26 mmol) $PPh_3$ (9.58 g, 36.52 mmol) in THF (50 mL) was added DEAD (4.77 g, 27.39 mmol) dropwise at 0~10° C. The yellow solution was stirred at 20° C. for 16 hrs. The yellow solution was diluted with water (80 mL), and then extracted with ethyl acetate (50 mL) twice. The organic layer was washed with brine (100 mL), dried by $Na_2SO_4$, and filtered. The filtrate was concentrated to give crude (22.60 g) as a yellow gum. The crude was purified by Combi-flash (silica gel, ethyl acetate in petrol ether from 10% to 25%) to give ethyl 5-bromo-2-[2-(tert-butoxycarbonylamino)ethyl]pyrazole-3-carboxylate (5.42 g, 81.9% yield) as a white solid.

$^1H$ NMR (400 MHz, CDCl3) δ ppm 6.84 (s, 1H) 4.84 (br s, 1H) 4.61-4.68 (t, J=5.60 Hz, 2H) 4.35 (q, J=7.20 Hz, 2H) 3.56-3.61 (m, 2H) 1.41 (s, 9H) 1.38 (t, J=7.15 Hz, 3H)

Step C: Ethyl 2-(2-aminoethyl)-5-bromo-pyrazole-3-carboxylate

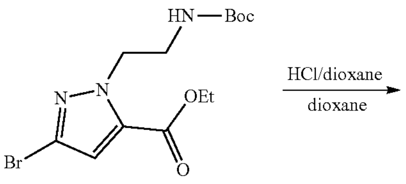

4

-continued

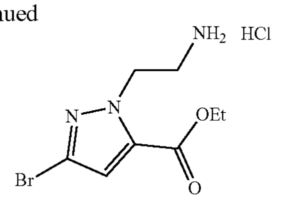
5

To a solution of ethyl 5-bromo-2-[2-(tert-butoxycarbonylamino)ethyl]pyrazole-3-carboxylate (5.42 g, 14.96 mmol) in dioxane (40 mL) was added HCl/dioxane (4 M, 56.11 mL). The solution was stirred at 20° C. for 7 hrs. The white suspension was concentrated to give ethyl 2-(2-aminoethyl)-5-bromo-pyrazole-3-carboxylate (4.10 g, crude, HCl salt) as a white solid.

1H NMR (400 MHz, METHANOL-d4) δ ppm 6.96 (s, 1H) 4.79-4.86 (m, 2H) 4.38 (q, J=7.15 Hz, 2H) 3.46 (m, 2H) 1.38 (t, J=7.15 Hz, 3H)

Step D: 2-Bromo-6,7-dihydro-5H-pyrazolo[1,5-a]pyrazin-4-one

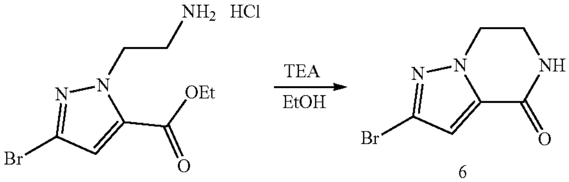

5
6

To a suspension of ethyl 2-(2-aminoethyl)-5-bromo-pyrazole-3-carboxylate (4.10 g, HCl salt) in EtOH (50 mL) was added TEA (6.95 g, 68.66 mmol, 9.56 mL). The solution was stirred at 80° C. for 1 hr. The solution was concentrated to remove the solvent, and then suspended in 25 mL of MeOH. The suspension was stirred at 20° C. for 0.5 hr. The mixture was filtered. The filter cake was dried by vacuum to give 2-bromo-6,7-dihydro-5H-pyrazolo[1,5-a]pyrazin-4-one (2.51 g, crude) as a white solid.

$^1H$ NMR (400 MHz, DMSO-d6) δ ppm 8.34 (br s, 1H) 6.84 (s, 1H) 4.28 (t, J=6.17 Hz, 2H) 3.54-3.65 (m, 2H)

Step E: 2-(4-Fluoro-3,5-dimethyl-phenyl)-4,4,5,5-tetramethyl-1,3,2-dioxaborolane

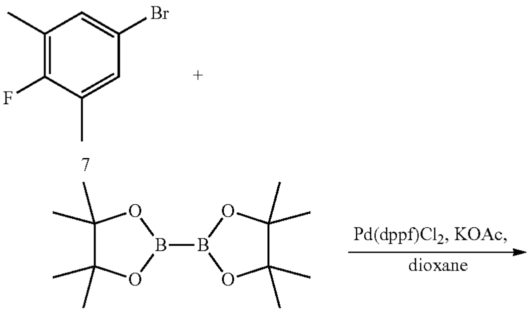

7

-continued

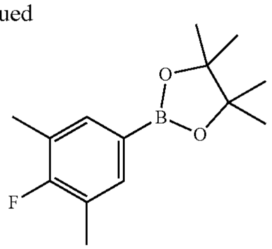

8

To a solution of 5-bromo-2-fluoro-1,3-dimethyl-benzene (253.0 mg, 1.25 mmol) in dioxane (3 mL) was added 4,4,5,5-tetramethyl-2-(4,4,5,5-tetramethyl-1,3,2-dioxaborolan-2-yl)-1,3,2-dioxaborolane (348.0 mg, 1.37 mmol), KOAc (366.8 mg, 3.74 mmol), Pd(dppf)$Cl_2$ (91.1 mg, 124.50 μmol). The yellow suspension was stirred at 80° C. for 2 hrs under $N_2$. The dark suspension was diluted with water (5 mL), and then extracted with ethyl acetate (5 mL) twice. The organic layer was dried by $Na_2SO_4$, and then filtered. The filtrate was concentrated to give crude (418.6 mg) as a yellow gum. The crude was purified by Combi-flash (silica gel, ethyl acetate in petrol ether 0~10%) to give 2-(4-fluoro-3,5-dimethyl-phenyl)-4,4,5,5-tetramethyl-1,3,2-dioxaborolane (258.3 mg, 82.9% yield) as a colorless oil.

$^1$H NMR (400 MHz, CDCl3) δ ppm 7.45-7.52 (m, 2H) 2.23-2.28 (m, 6H) 1.35 (s, 12H)

Step F: 2-(4-Fluoro-3,5-dimethyl-phenyl)-6,7-dihydro-5H-pyrazolo[1,5-a]pyrazin-4-one

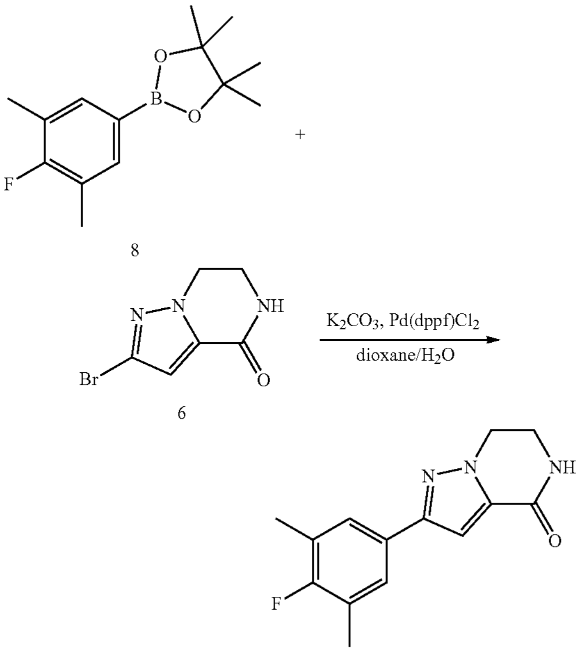

8 6 9

To a solution of 2-bromo-6,7-dihydro-5H-pyrazolo[1,5-a]pyrazin-4-one (2.51 g) and 2-(4-fluoro-3,5-dimethyl-phenyl)-4,4,5,5-tetramethyl-1,3,2-dioxaborolane (2.91 g, 11.62 mmol) in dioxane (30 mL) was added Pd(dppf)$Cl_2$ (850.1 mg, 1.16 mmol), $K_2CO_3$ (4.82 g, 34.86 mmol), $H_2O$ (10 mL). The suspension was stirred at 80° C. for 3 hrs under $N_2$. The yellow mixture was diluted with water (50 mL), and then extracted with ethyl acetate (50 mL) for three times. The organic layer was washed with brine (100 mL), dried by $Na_2SO_4$, and filtered. The filtrate was concentrated to give crude (4.10 g) as a yellow solid. The crude was purified by Combi-flash (silica gel, ethyl acetate in petrol ether 70~100%) to give 2-(4-fluoro-3,5-dimethyl-phenyl)-6,7-dihydro-5H-pyrazolo[1,5-a]pyrazin-4-one (2.54 g, 84.3% yield) as a yellow solid.

$^1$H NMR (400 MHz, METHANOL-d4) δ ppm 7.46-7.53 (m, 2H) 7.08 (s, 1H) 4.35-4.43 (m, 2H) 3.73-3.79 (m, 2H) 2.24-2.31 (m, 6H)

Step G: 2-(4-Fluoro-3,5-dimethyl-phenyl)-4,5,6,7-tetrahydropyrazolo[1,5-a]pyrazine

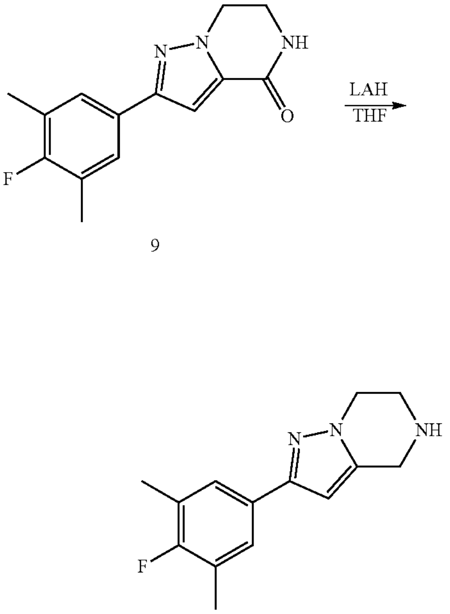

9 10

To a solution of 2-(4-fluoro-3,5-dimethyl-phenyl)-6,7-dihydro-5H-pyrazolo[1,5-a]pyrazin-4-one (2.53 g, 9.76 mmol) in THF (35 mL) was added LAH (370.4 mg, 9.76 mmol) in portions under $N_2$. The yellow solution was stirred at 65° C. for 16 hrs. To the deep yellow solution was added water (40 mL) dropwise at 0° C. to quench the reaction. The mixture was diluted with ethyl acetate (30 mL). The mixture was filtered with celite. The filtrate was separated. The organic layer was washed with brine (30 mL), dried by $Na_2SO_4$, and filtered. The filtrate was concentrated to give 2-(4-fluoro-3,5-dimethyl-phenyl)-4,5,6,7-tetrahydropyrazolo[1,5-a]pyrazine (2.00 g, crude) as a yellow solid.

$^1$H NMR (400 MHz, CDCl3) δ ppm 7.39-7.43 (m, 2H) 6.22 (s, 1H) 4.12-4.20 (m, 2H) 4.09 (br s, 2H) 3.34 (br t, J=5.38 Hz, 2H) 2.26-2.35 (m, 6H)

Step H: tert-Butyl 2-(4-fluoro-3,5-dimethyl-phenyl)-6,7-dihydro-4H-pyrazolo[1,5-a]pyrazine-5-carboxylate

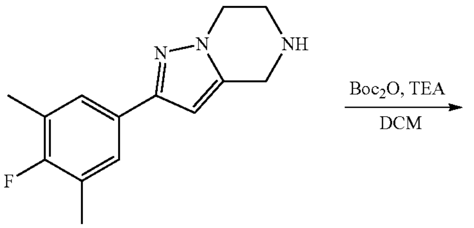

10

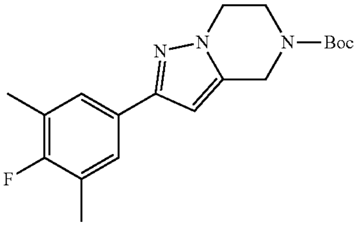

11

To a solution of 2-(4-fluoro-3,5-dimethyl-phenyl)-4,5,6,7-tetrahydropyrazolo[1,5-a]pyrazine (2.00 g) in DCM (30 mL) was added TEA (2.48 g, 24.46 mmol) and $(Boc)_2O$ (1.96 g, 8.97 mmol, 2.06 mL) at 0° C. The deep yellow solution was stirred at 20° C. for 1.5 hrs. The yellow solution was concentrated to give crude (4.32 g) as a deep yellow gum. The crude was purified by Combi-flash (silica gel, ethyl acetate in petrol ether 15~35%) to give tert-butyl 2-(4-fluoro-3,5-dimethyl-phenyl)-6,7-dihydro-4H-pyrazolo[1,5-a]pyrazine-5-carboxylate (1.56 g, 55.4% yield) as a yellow solid.

$^1$H NMR (400 MHz, CDCl3) δ ppm 7.35-7.45 (m, 2H) 6.29 (s, 1H) 4.68 (s, 2H) 4.22 (t, J=5.27 Hz, 2H) 3.92 (t, J=5.27 Hz, 2H) 2.26-2.33 (m, 6H) 1.43-1.60 (m, 9H)

Step I: tert-Butyl 3-bromo-2-(4-fluoro-3,5-dimethyl-phenyl)-6,7-dihydro-4H-pyrazolo[1,5-a]pyrazine-5-carboxylate

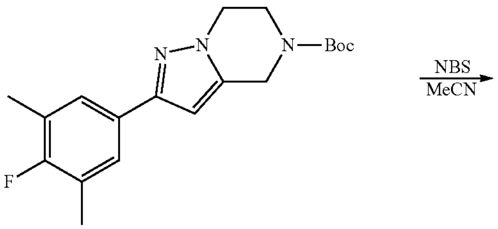

11

-continued

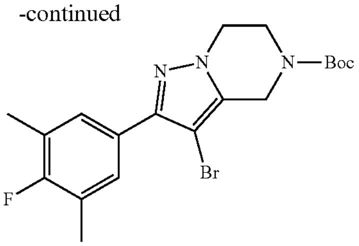

12

To a yellow solution of tert-butyl 2-(4-fluoro-3,5-dimethyl-phenyl)-6,7-dihydro-4H-pyrazolo[1,5-a]pyrazine-5-carboxylate (1.56 g, 4.52 mmol) in MeCN (20 mL) was added NBS (803.8 mg, 4.52 mmol). The solution was stirred at 20° C. for 2 hrs under $N_2$. The yellow solution was concentrated to give crude (2.72 g) as a yellow solid. The crude was purified by Combi-flash (silica gel, ethyl acetate in petrol ether 15~35%) to give tert-butyl 3-bromo-2-(4-fluoro-3,5-dimethyl-phenyl)-6,7-dihydro-4H-pyrazolo[1,5-a]pyrazine-5-carboxylate (1.63 g, 85.1% yield) as a white solid.

$^1$H NMR (400 MHz, CDCl3) δ ppm 7.47-7.54 (m, 2H) 4.59 (br s, 2H) 4.19 (t, J=5.25 Hz, 2H) 3.93 (br t, J=5.13 Hz, 2H) 2.27-2.35 (m, 6H) 1.53 (s, 9H)

Step J: tert-Butyl 3-(benzhydrylideneamino)-2-(4-fluoro-3,5-dimethyl-phenyl)-6,7-dihydro-4H-pyrazolo[1,5-a]pyrazine-5-carboxylate

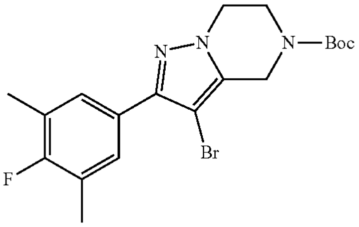

+

12

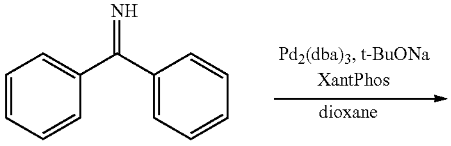

13

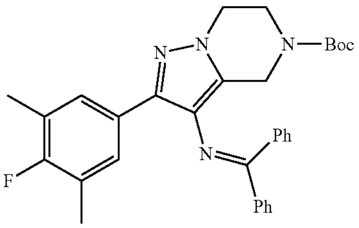

14

To a solution of tert-butyl 3-bromo-2-(4-fluoro-3,5-dimethyl-phenyl)-6,7-dihydro-4H-pyrazolo[1,5-a]pyrazine-5-carboxylate (1.63 g, 3.84 mmol) and diphenylmethanimine (1.04 g, 5.76 mmol) in dioxane (25 mL) was added t-BuONa (1.48 g, 15.37 mmol), $Pd_2(dba)_3$ (351.8 mg, 384.18 μmol), Xantphos (355.6 mg, 614.57 μmol). The suspension was stirred at 90° C. for 16 hrs under $N_2$. The dark suspension was diluted with water (50 mL), and then extracted with ethyl acetate (40 mL) twice. The organic layer was washed with brine (60 mL), dried by $Na_2SO_4$, and filtered. The filtrate was concentrated to give crude (4.10 g) as a yellow gum. The crude was purified by Combi-flash (silica gel, ethyl acetate in petrol ether from 15% to 35%) to give tert-butyl 3-(benzhydrylideneamino)-2-(4-fluoro-3,5-dimethyl-phenyl)-6,7-dihydro-4H-pyrazolo[1,5a]pyrazine-5-carboxylate (2.02 g, 100.00% yield) as a yellow gum.

$^1H$ NMR (400 MHz, CDCl3) δ ppm 7.74-7.80 (m, 2H) 7.38-7.62 (m, 8H) 7.06 (m, 2H) 4.04-4.11 (m, 2H) 3.82 (br s, 2H) 3.61-3.72 (m, 2H) 2.17-2.24 (m, 6H) 1.46 (s, 9H)

Step K: tert-Butyl 3-amino-2-(4-fluoro-3,5-dimethyl-phenyl)-6,7-dihydro-4H-pyrazolo[1,5-a]pyrazine-5-carboxylate

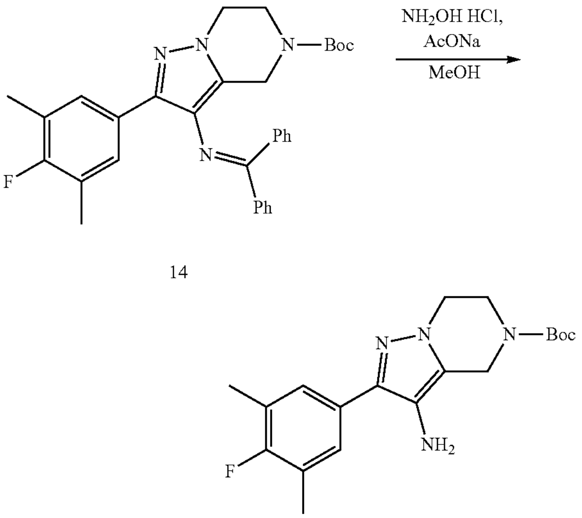

14

15

To a yellow solution of tert-butyl 3-(benzhydrylideneamino)-2-(4-fluoro-3,5-dimethyl-phenyl)-6,7-dihydro-4H-pyrazolo[1,5-a]pyrazine-5-carboxylate (2.02 g, 3.85 mmol) in MeOH (35 mL) was added NaOAc (947.6 mg, 11.55 mmol) and $NH_2OH{\cdot}HCl$ (535.2 mg, 7.70 mmol) under $N_2$. The yellow cloudy solution was stirred at 20° C. for 17 hrs. The yellow solution was concentrated to remove the most of MeOH, and then diluted with water (30 mL). The mixture was extracted with ethyl acetate (25 mL) twice. The organic layer was washed with brine (50 mL), dried by $Na_2SO_4$, and filtered. The filtrate was concentrated to give crude (2.01 g) as a yellow gum. The crude was purified by Combi-flash (silica gel, ethyl acetate in petrol ether from 20% to 70%) to give tert-butyl 3-amino-2-(4-fluoro-3,5-dimethyl-phenyl)-6,7-dihydro-4H-pyrazolo[1,5-a]pyrazine-5-carboxylate (960.5 mg, 69.2% yield) as a yellow gum.

$^1H$ NMR (400 MHz, CDCl3) δ ppm 7.32-7.38 (m, 2H) 4.57 (s, 2H) 4.08-4.20 (m, 2H) 3.90 (br d, J=5.00 Hz, 2H) 2.99 (br s, 2H) 2.26-2.34 (m, 6H) 1.52 (s, 9H)

Step L: 2-isocyanato-1,1-dimethoxy-ethane

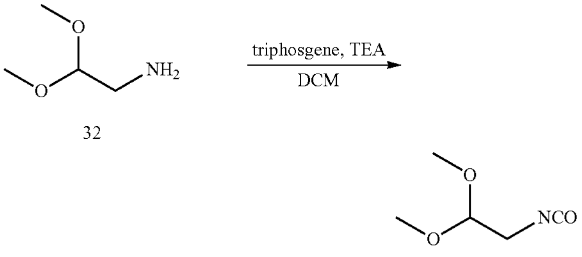

32

16

To a solution of triphosgene (3.95 g, 13.32 mmol) in DCM (100 mL) was added a solution of 2,2-dimethoxy-ethanamine (4.12 g, 39.19 mmol, 4.27 mL) and TEA (7.93 g, 78.37 mmol, 10.91 mL, 2 eq) in DCM (100 mL) dropwise over 0.2 hr under $N_2$ at 0° C. The white suspension was stirred at 20° C. for 0.3 hr. Then the suspension was stirred at 45° C. for 0.3 hr, and then stirred at 20° C. for 3.5 hrs. The cloudy solution was washed with water (150 mL), dried by $Na_2SO_4$, and filtered. The filtrate was concentrated to give crude (4.12 g). The crude was suspended in 20 mL of petrol ether, and then filtered. The filtrate was concentrated to give 2-isocyanato-1,1-dimethoxy-ethane (3.85 g, crude) as a colorless oil.

$^1H$ NMR (400 MHz, CDCl3) δ ppm 4.48 (t, J=5.32 Hz, 1H) 3.42 (s, 6H) 3.32 (d, J=5.38 Hz, 2H)

Step M: tert-butyl 3-(2,2-dimethoxyethylcarbamoylamino)-2-(4-fluoro-3,5-dimethyl-phenyl)-6,7-dihydro-4H-pyrazolo[1,5-a]pyrazine-5-carboxylate

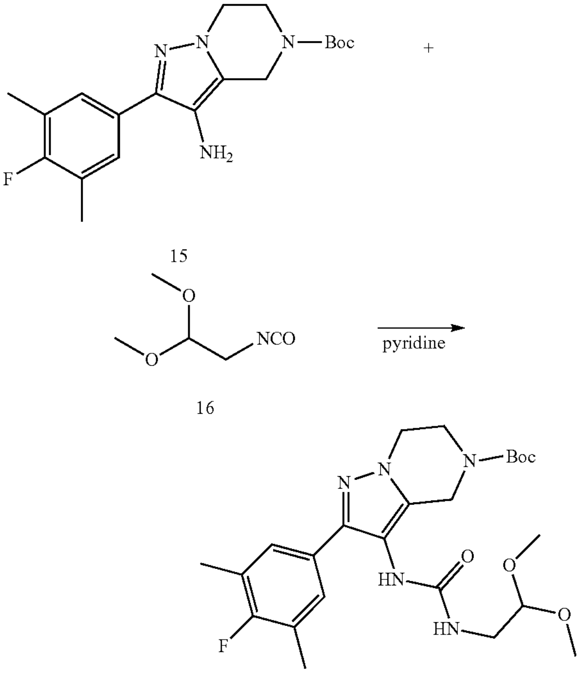

15

16

17

To a solution of tert-butyl 3-amino-2-(4-fluoro-3,5-dimethyl-phenyl)-6,7-dihydro-4H-pyrazolo[1,5-a]pyrazine-5-carboxylate (910.5 mg, 2.53 mmol) in pyridine (12 mL) was added 2-isocyanato-1,1-dimethoxy-ethane (397.5 mg). The yellow solution was stirred at 20° C. for 2 hrs under $N_2$. To the solution was added MeOH (5 mL) to quench the reaction. The solution was concentrated to give crude (1.26 g) as a yellow solid. The crude was purified by Combi-flash (silica gel, ethyl acetate in petrol ether from 50 to 100%) to give tert-butyl 3-(2,2-dimethoxyethylcarbamoylamino)-2-(4-fluoro-3,5-dimethyl-phenyl)-6,7-dihydro-4H-pyrazolo[1,5-a]pyrazine-5-carboxylate (961.2 mg, 77.4% yield) as a yellow solid.

$^1$H NMR (400 MHz, CDCl3) δ ppm 7.38-7.43 (m, 2H) 5.61 (br s, 1H) 4.81 (t, J=6.02 Hz, 1H) 4.59 (s, 2H) 4.24 (t, J=5.27 Hz, 1H) 4.20 (br t, J=5.14 Hz, 2H) 3.93 (br t, J=5.27 Hz, 2H) 3.26-3.34 (m, 8H) 2.25-2.31 (d, J=2.01 Hz, 6H) 1.51 (s, 9H)

Step N: tert-butyl 2-(4-fluoro-3,5-dimethyl-phenyl)-3-(2-oxo-1H-imidazol-3-yl)-6,7-dihydro-4H-pyrazolo[1,5-a]pyrazine-5-carboxylate

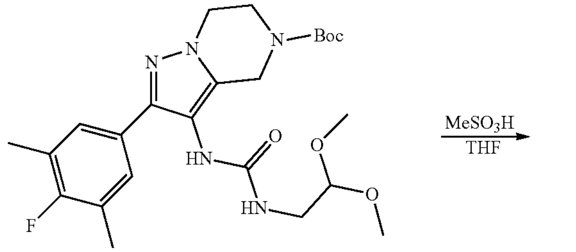

17

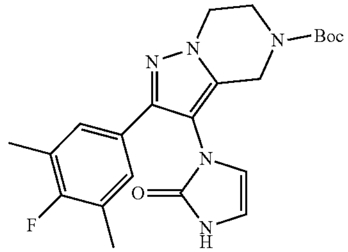

18

To a yellow suspension of tert-butyl 3-(2,2-dimethoxyethylcarbamoylamino)-2-(4-fluoro-3,5-dimethyl-phenyl)-6,7-dihydro-4H-pyrazolo[1,5-a]pyrazine-5-carboxylate (950.0 mg, 1.93 mmol) in THF (14 mL) was added methanesulfonic acid (185.7 mg, 1.93 mmol, 137.56 uL) at 60° C. under $N_2$. The yellow solution was stirred at 60° C. for 1.5 hrs. The yellow suspension was diluted with 1N $NaHCO_3$ (15 mL), and then extracted with ethyl acetate (12 mL) twice. The organic layer was dried by $Na_2SO_4$, and then filtered. The filtrate was concentrated to give tert-butyl 2-(4-fluoro-3,5-dimethyl-phenyl)-3-(2-oxo-1H-imidazol-3-yl)-6,7-dihydro-4H-pyrazolo[1,5-a]pyrazine-5-carboxylate (851.2 mg, crude) as a yellow solid.

$^1$H NMR (400 MHz, CDCl3) δ ppm 10.39 (br s, 1H) 7.14-7.20 (m, 2H) 6.33-6.40 (m, 1H) 6.11 (t, J=4.00 Hz, 1H) 4.68 (s, 2H) 4.10-4.27 (m, 2H) 3.97 (t, J=4.89 Hz, 2H) 2.20-2.27 (m, 6H) 1.44-1.52 (m, 9H)

Step O: tert-butyl 2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carboxylate

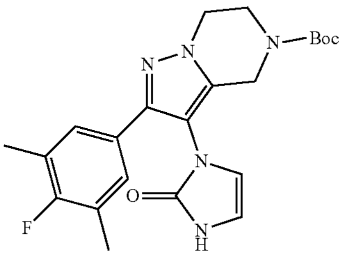

+

18

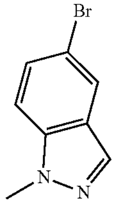

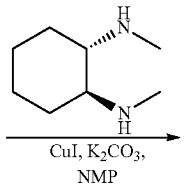

19

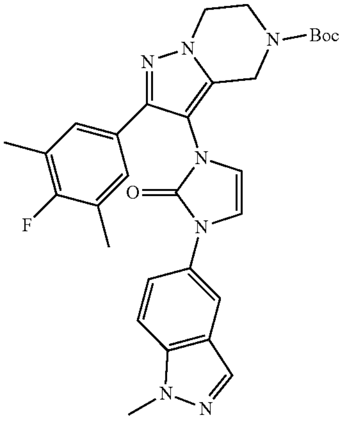

20

To a solution of tert-butyl 2-(4-fluoro-3,5-dimethyl-phenyl)-3-(2-oxo-1H-imidazol-3-yl)-6,7-dihydro-4H-pyrazolo[1,5-a]pyrazine-5-carboxylate (120.0 mg) and 5-bromo-1-methyl-indazole (118.5 mg, 561.46 μmol) in NMP (5 mL) was added $K_2CO_3$ (116.4 mg, 842.22 μmol), (1S,2S)—N1,N2-dimethylcyclohexane-1,2-diamine (17.6 mg, 123.73 μmol), CuI (10.7 mg, 56.18 μmol) under $N_2$. The suspension was stirred at 130° C. for 3 hrs under $N_2$. The brown suspension was diluted with water (3 mL), and then extracted with ethyl acetate (2 mL) for three times. The organic layer was dried by $Na_2SO_4$, and then filtered. The filtrate was concentrated to give crude (226.5 mg) as a yellow gum. The crude was purified by Combi-flash (silica gel, MeOH in DCM from 0% to 15%) to give tert-butyl 2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carboxylate (132.6 mg, 84.7% yield) as a yellow solid. (ESI) m/z $(M+H)^+$=558.1

Step P: 1-[2-(4-fluoro-3,5-dimethyl-phenyl)-4,5,6,7-tetrahydro-pyrazolo[1,5-a]pyrazin-3-yl]-3-(1-methylindazol-5-yl)imidazol-2-one

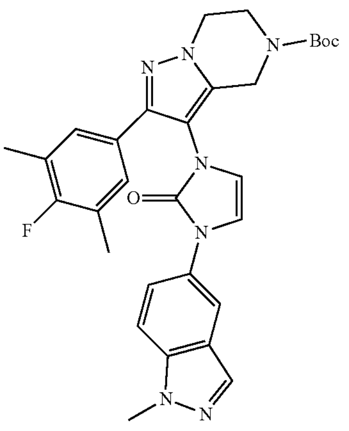

20

HCl/dioxane

EtOAc

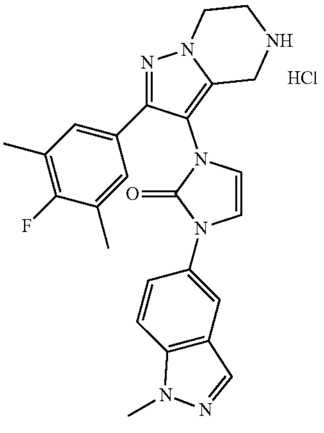

21

To a solution of tert-butyl 2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carboxylate (132.6 mg, 237.80 μmol) in EtOAc (2.00 mL) was added HCl/dioxane (4 M, 5.30 mL, 89.22 eq). The solution was stirred at 15° C. for 2 hrs. The yellow suspension was filtered. The filter cake was dried by vacuum to give 1-[2-(4-fluoro-3,5-dimethyl-phenyl)-4,5,6,7-tetrahydropyrazolo[1,5-a]pyrazin-3-yl]-3-(1-methylindazol-5-yl)imidazol-2-one (122.4 mg, crude, HCl salt) as a yellow solid. (ESI) m/z $(M+H)^+$=458.1

Step Q: 3-[(1S,2S)-1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]-2-methyl-cyclopropyl]-4H-1,2,4-oxadiazol-5-one

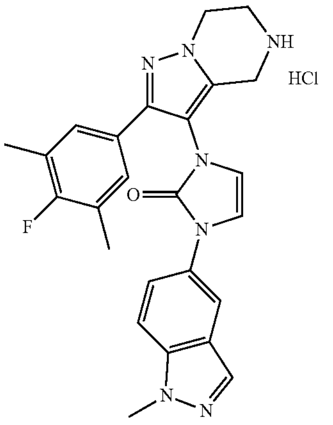

21

+

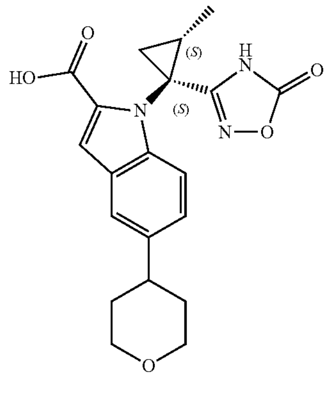

22

$T_3P$, TEA

THF

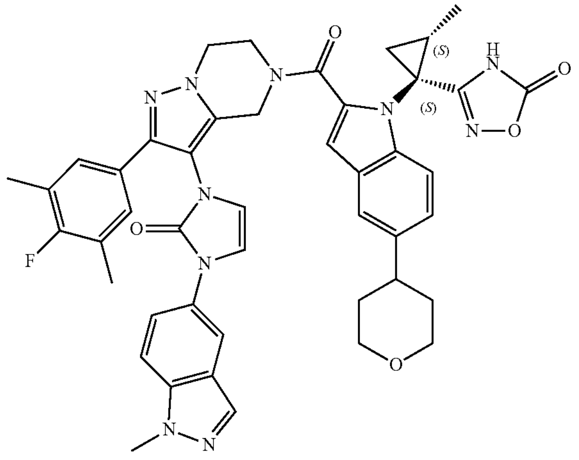

105a

To a suspension of 1-[(1S,2S)-2-methyl-1-(5-oxo-4H-1,2,4-oxadiazol-3-yl)cyclopropyl]-5-tetrahydropyran-4-yl-indole-2-carboxylic acid (67.5 mg, 176.06 μmol; may be prepared in analogous fashion to compound 28 in Example 3) and 1-[2-(4-fluoro-3,5-dimethyl-phenyl)-4,5,6,7-tetrahydropyrazolo[1,5-a]pyrazin-3-yl]-3-(1-methylindazol-5-yl)imidazol-2-one (86.9 mg HCl salt) in THF (1.5 mL) was added $T_3P$ (145.60 mg, 228.80 mol, 50% purity) and TEA (71.26 mg, 704.23 μmol). The suspension was stirred at 25° C. for 1 hr under $N_2$. The yellow solution was diluted with water (2 mL), and then extracted with ethyl acetate (2 mL) for three times. The organic layer was dried by $Na_2SO_4$, and then filtered. The filtrate was concentrated to give crude (155.2 mg) as a yellow solid. The crude was purified by prep-HPLC. Column: Phenomenex Gemini C18 250*50 mm*10 um; mobile phase: [water (0.225% FA)-ACN]; B %: 50%-70%, 10 min. The fraction was dried by lyophilization to give 3-[(1S,2S)-1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]-2-methyl-cyclopropyl]-4H-1,2,4-oxadiazol-5-one (40.18 mg, 27.2% yield) as a white solid.

$^1H$ NMR (400 MHz, DMSO-$d_6$) δ ppm 11.57 (br s, 1H) 8.02-8.09 (m, 1H) 7.98 (s, 1H) 7.66 (s, 2H) 7.50 (s, 1H) 7.42 (d, J=8.56 Hz, 1H) 7.21-7.32 (m, 3H) 7.15 (d, J=3.18 Hz, 1H) 6.93 (s, 1H) 6.67 (d, J=3.18 Hz, 1H) 4.88-5.06 (m, 2H) 4.22-4.38 (m, 4H) 4.08 (s, 3H) 3.88-4.01 (m, 2H) 3.38-3.55 (m, 2H) 2.85 (m, 1H) 2.22 (m, 6H) 1.86-1.97 (m, 1H) 1.58-1.78 (m, 6H) 1.18-1.32 (m, 3H). $^{19}F$ NMR (377 MHz, DMSO-d6) δ ppm −122.19. (ESI) m/z $(M+H)^+$=823.1

Example 2

3-(1-(2-(2-(4-fluoro-3,5-dimethylphenyl)-3-(3-(1-methyl-1H-indazol-5-yl)-2-oxo-2,3-dihydro-1H-imidazol-1-yl)-4,5,6,7-tetrahydropyrazolo[1,5-a]pyrazine-5-carbonyl)-5-(tetrahydro-2H-pyran-4-yl)-1H-indol-1-yl)cyclopropyl)-1,2,4-oxadiazol-5(4H)-one (Compound 101)

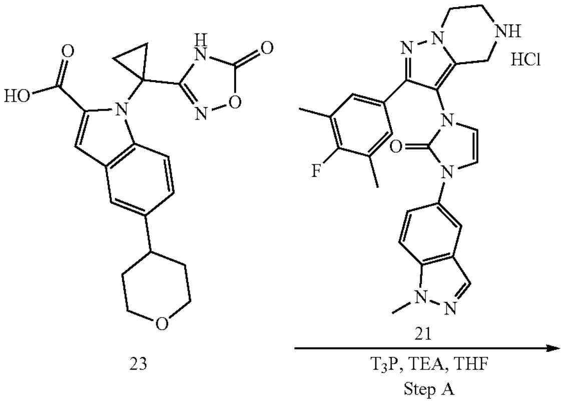

-continued

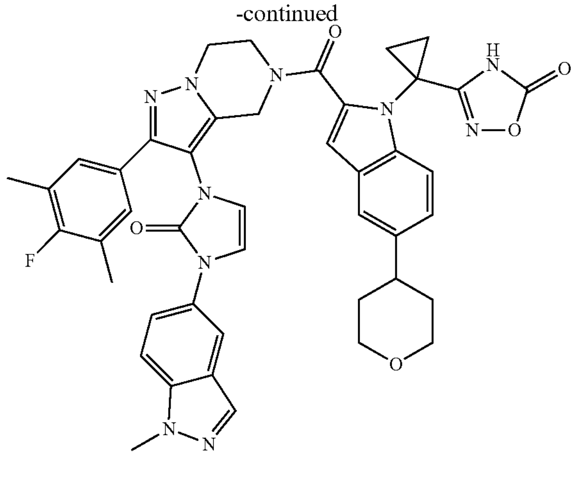

101

Step A: 3-[1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]cyclopropyl]-4H-1,2,4-oxadiazol-5-one

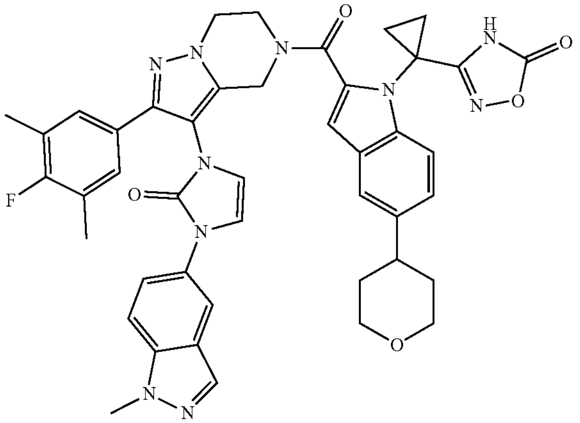 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CC2)CC3)cc(C)c1F]

To a suspension of 1-[1-(5-oxo-2H-1,2,4-oxadiazol-3-yl)cyclopropyl]-5-tetrahydropyran-4-yl-indole-2-carboxylic acid (66.0 mg, 0.179 mmol) and 1-[2-(4-fluoro-3,5-dimethyl-phenyl)-4,5,6,7-tetrahydropyrazolo[1,5-a]pyrazin-3-yl]-3-(1-methylindazol-5-yl)imidazol-2-one (81.8 mg, 0.179 mmol) in THF (1.5 mL) was added TEA (90.4 mg, 0.893 mmol) and $T_3P$ (148 mg, 0.232 mmol, 50% in ethyl acetate). The yellow suspension was stirred at 15° C. for 16 h under $N_2$. The suspension was diluted with water (3 mL) and extracted with ethyl acetate (3 mL) twice. The organic layer was dried by $Na_2SO_4$ and filtered. The filtrate was concentrated to give crude (111 mg) as a yellow gum. The crude was purified by prep-HPLC. Column: Phenomenex Gemini C18 250*50 mm*10 um; mobile phase: [water (0.225% FA)-ACN]; B %: 50%-70%, 10 min. The fraction was dried by lyophilization to give 3-[1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]cyclopropyl]-4H-1,2,4-oxadiazol-5-one (20.64 mg, 14.0% yield) as a white solid.

$^1$H NMR (400 MHz, DMSO-d6) δ ppm 12.12 (brs, 1H), 8.06 (s, 1H), 8.00 (br.s, 1H), 7.71 (brs, 2H), 7.58-7.39 (m, 2H), 7.35-7.10 (m, 4H), 6.87 (s, 1H), 6.67 (brs, 1H), 5.12-4.68 (m, 2H), 4.41-4.28 (m, 2H), 4.26-4.02 (m, 4H), 4.00-3.85 (m, 2H), 3.52-3.30 (m, 3H, overlap with $H_2O$), 2.89-2.77 (m, 1H), 2.21 (s, 6H), 1.81-1.54 (m, 8H).
Example 3
3-(1-(2-(2-(4-fluoro-3,5-dimethylphenyl)-3-(3-(1-methyl-1H-indazol-5-yl)-2-oxo-2,3-dihydro-1H-imidazol-1-yl)-4,5,6,7-tetrahydropyrazolo[1,5-a]pyrazine-5-carbonyl)-5-(tetrahydro-2H-pyran-4-yl)-1H-indol-1-yl)cyclobutyl)-1,2,4-oxadiazol-5(4H)-one (Compound 102)
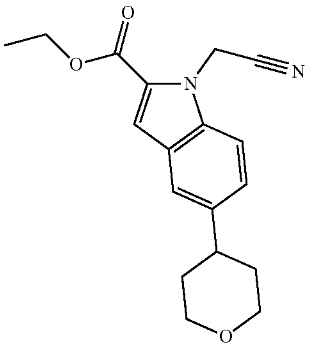
24
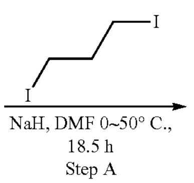
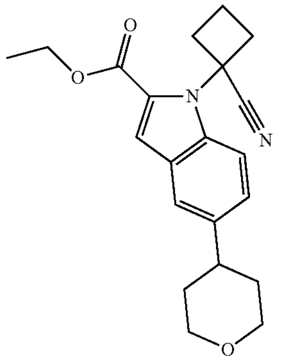
25
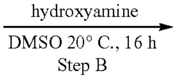
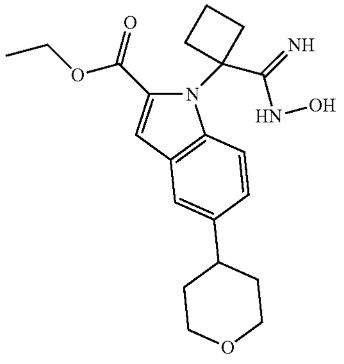
26
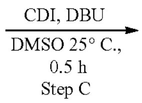
-continued
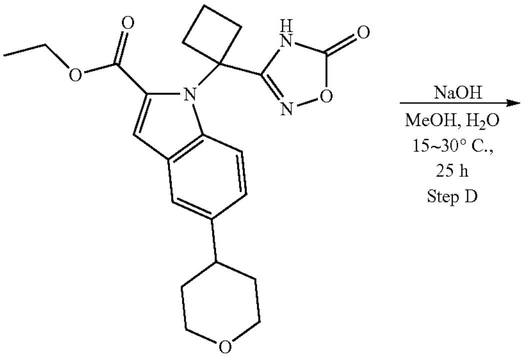
27
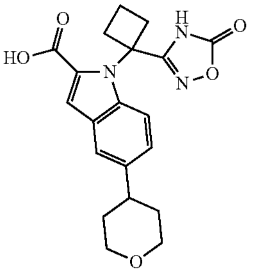
28
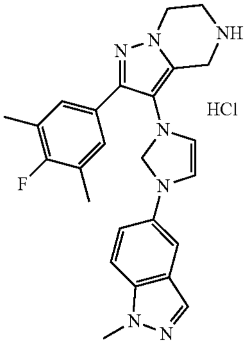
21
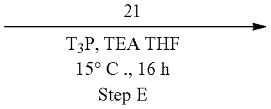
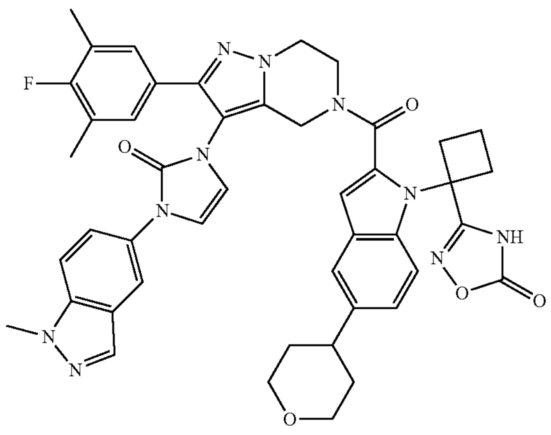

Step A: ethyl 1-(1-cyanocyclobutyl)-5-tetrahydropyran-4-yl-indole-2-carboxylate

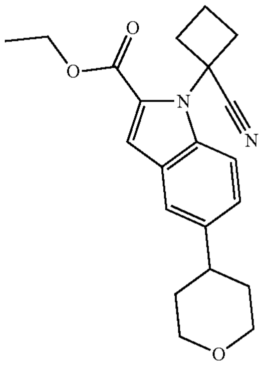 [SMILES: CCOC(=O)c1cc2cc(C3CCOCC3)ccc2n1C1(C#N)CCC1]

To a suspension of NaH (117 mg, 2.92 mmol, 60% purity in mineral oil) in DMF (4.5 mL) was added ethyl 1-(cyanomethyl)-5-tetrahydropyran-4-yl-indole-2-carboxylate (365 mg, 1.17 mmol) at 0° C. The suspension was stirred at 0° C. for 0.5 h. To the suspension was added 1,3-diiodopropane (484 mg, 1.64 mmol). The suspension was stirred at 50° C. for 18 hrs under $N_2$. To the yellow solution was added water (12 mL) to quench the reaction. The mixture was extracted with ethyl acetate (10 mL) twice. The organic layer was washed with water (15 mL), dried by $Na_2SO_4$, and filtered. The filtrate was concentrated to give crude (328 mg) as a yellow gum. The crude was purified by Combi-flash (silica gel, ethyl acetate in petrol ether from 7~35%) to give ethyl 1-(1-cyanocyclobutyl)-5-tetrahydropyran-4-yl-indole-2-carboxylate (51.2 mg, 12.4% yield) as a yellow gum.

$^1$H NMR (400 MHz, CDCl3) δ ppm 7.52 (s, 1H), 7.36-7.30 (m, 1H), 7.30-7.24 (m, 2H), 4.40 (q, J=6.8 Hz, 2H), 4.17-4.08 (m, 2H), 3.62-3.51 (m, 2H), 3.33-3.25 (m, 1H), 2.96-2.77 (m, 3H), 2.46-2.33 (m, 1H), 2.05-1.79 (m, 6H), 1.44 (t, J=6.8 Hz, 3H).

Step B: ethyl 1-[1-(N-hydroxycarbamimidoyl)cyclobutyl]-5-tetrahydropyran-4-yl-indole-2-carboxylate

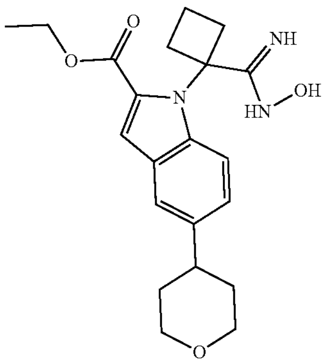 [SMILES: CCOC(=O)c1cc2cc(C3CCOCC3)ccc2n1C1(C(=N)NO)CCC1]

To a solution of ethyl 1-(1-cyanocyclobutyl)-5-tetrahydropyran-4-yl-indole-2-carboxylate (59 mg, 0.167 mmol) in DMSO (0.7 mL) was added hydroxylamine (111 mg, 1.67 mmol, 50% purity). The solution was stirred at 20° C. for 16 hrs under $N_2$. The white suspension was diluted with water (2 mL), and extracted with ethyl acetate (2 mL) for three times. The organic layer was washed with water (5 mL), brine (5 mL), dried by $Na_2SO_4$, and filtered. The filtrate was concentrated to give ethyl 1-[1-(N-hydroxycarbamimidoyl)cyclobutyl]-5-tetrahydropyran-4-yl-indole-2-carboxylate (59 mg, crude) as a white solid.

Step C: ethyl 1-[1-(5-oxo-4H-1,2,4-oxadiazol-3-yl)cyclobutyl]-5-tetrahydropyran-4-yl-indole-2-carboxylate

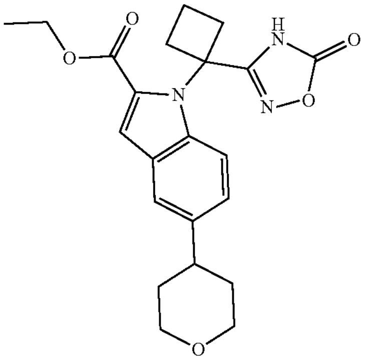 [SMILES: CCOC(=O)c1cc2cc(C3CCOCC3)ccc2n1C1(c2noc(=O)[nH]2)CCC1]

To a solution of ethyl 1-[1-(N-hydroxycarbamimidoyl)cyclobutyl]-5-tetrahydropyran-4-yl-indole-2-carboxylate (59 mg, crude) in DMSO (0.7 mL) was added CDI (49.6 mg, 0.306 mmol) and DBU (58 mg, 0.383 mmol). The solution was stirred at 25° C. for 0.5 h under $N_2$. To the yellow solution was added 0.06 mL of FA to quench the reaction. The mixture was diluted with water (2 mL), and extracted with ethyl acetate (2 mL) twice. The organic layer was washed with water (3 mL), and concentrated to give ethyl 1-[1-(5-oxo-4H-1,2,4-oxadiazol-3-yl)cyclobutyl]-5-tetrahydropyran-4-yl-indole-2-carboxylate (50 mg, crude) as a light yellow solid.

Step D: 1-[1-(5-oxo-4H-1,2,4-oxadiazol-3-yl)cyclobutyl]-5-tetrahydropyran-4-yl-indole-2-carboxylic acid

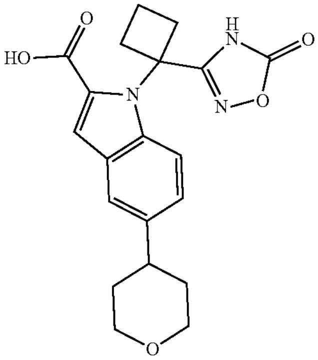 [SMILES: O=C(O)c1cc2cc(C3CCOCC3)ccc2n1C1(c2noc(=O)[nH]2)CCC1]

To a suspension of ethyl 1-[1-(5-oxo-4H-1,2,4-oxadiazol-3-yl)cyclobutyl]-5-tetrahydropyran-4-yl-indole-2-carboxylate (50 mg, crude) in MeOH (0.9 mL) was added NaOH (29 mg, 0.73 mmol) and $H_2O$ (0.3 mL). The solution was stirred at 15° C. for 18 hrs. The solution was diluted with water (2 mL), and extracted with DCM/MeOH (1.5 mL, 10:1). The water layer was treated with 1N HCl to adjust pH to 5~6. The mixture was extracted with DCM/MeOH (2 mL, 10:1) twice. The organic layer was dried by $Na_2SO_4$ and filtered. The filtrate was concentrated to give 1-[1-(5-oxo-4H-1,2,4-oxadiazol-3-yl)cyclobutyl]-5-tetrahydropyran-4-yl-indole-2-carboxylic acid (41 mg, crude) as a yellow gum.

Step E: 3-[1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]cyclobutyl]-4H-1,2,4-oxadiazol-5-one

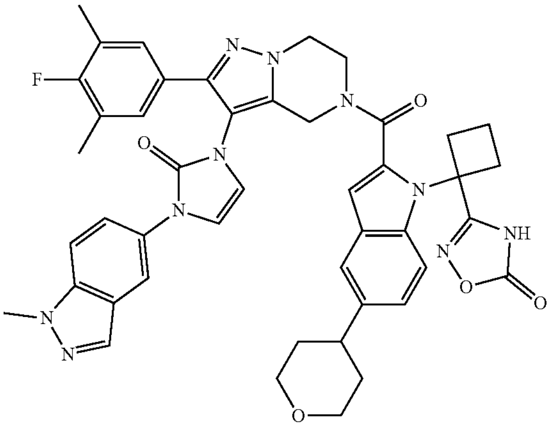 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CCC2)CC3)cc(C)c1F]

To a solution of 1-[2-(4-fluoro-3,5-dimethyl-phenyl)-4,5,6,7-tetrahydropyrazolo[1,5-a]pyrazin-3-yl]-3-(1-methylindazol-5-yl)imidazol-2-one (40 mg, crude) and 1-[1-(5-oxo-4H-1,2,4-oxadiazol-3-yl)cyclobutyl]-5-tetrahydropyran-4-yl-indole-2-carboxylic acid (0.108 mmol) in THF (0.6 mL) was added TEA (41 mg, 0.405 mmol) and $T_3P$ (67 mg, 0.105 mmol, 50% purity). The solution was stirred at 15° C. for 16 h under $N_2$. The yellow suspension was diluted with water (2 mL), and extracted with ethyl acetate (2 mL) for three times. The organic layer was concentrated to give crude (68.0 mg) as a yellow solid. The crude was purified by prep-HPLC. Column: Phenomenex Gemini C18 250*50 mm*10 um; mobile phase: [water (0.05% ammonia hydroxide v/v)-ACN]; B %: 55%-75%, 10 min. The fraction was dried by lyophilization to give 3-[1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]cyclobutyl]-4H-1,2,4-oxadiazol-5-one (4.96 mg, 3.5% yield for 4 steps) as a white solid.

$^1$H NMR (400 MHz, DMSO-$d_6$) δ ppm 8.11 (s, 1H), 8.05 (d, J=1.2 Hz, 1H), 7.97 (d, J=8.8 Hz, 1H), 7.78-7.70 (m, 2H), 7.64 (s, 1H), 7.38 (dd, J=8.8, 1.6 Hz, 1H), 7.32 (s, 1H), 7.28 (d, J=3.2 Hz, 1H), 7.22 (d, J=6.8 Hz, 2H), 6.78 (d, J=2.8 Hz, 1H), 4.99-4.58 (m, 2H), 4.37-4.14 (m, 2H), 4.07 (s, 3H), 4.00-3.93 (m, 2H), 3.51-3.42 (m, 2H), 3.32-3.30 (m, 2H), 3.29-3.19 (m, 2H), 2.95-2.83 (m, 3H), 2.35-2.22 (m, 2H), 2.19 (d, J=1.2 Hz, 6H), 1.81-1.67 (m, 4H).

Example 4

(1S,2S)-1-(2-(2-(4-fluoro-3,5-dimethylphenyl)-3-(3-(1-methyl-1H-indazol-5-yl)-2-oxo-2,3-dihydro-1H-imidazol-1-yl)-4,5,6,7-tetrahydropyrazolo[1,5-a]pyrazine-5-carbonyl)-5-(tetrahydro-2H-pyran-4-yl)-1H-indol-1-yl)-2-methylcyclopropanecarboxylic acid (Compound 106a)

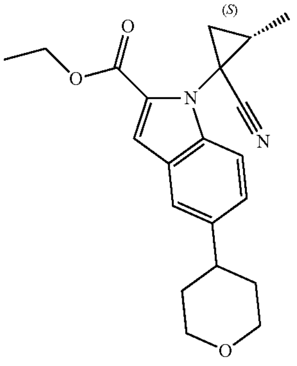

24

TBD
MeCN, $H_2O$
25° C., 4 h
Step A

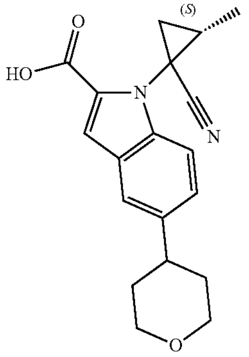

30

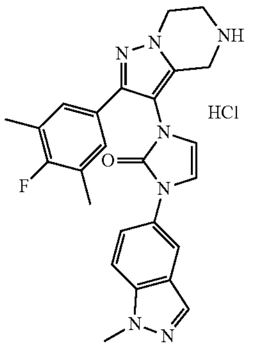

21

$T_3P$, TEA, THF
15° C., 18 h
Step B

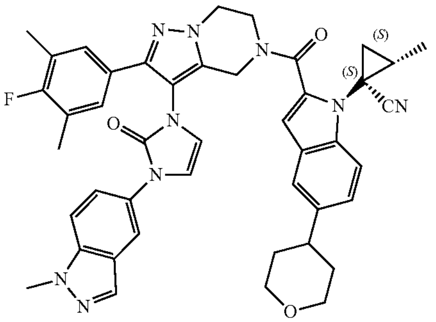

31

Conc. HCl
AcOH
65° C., 18 h
Step C

-continued

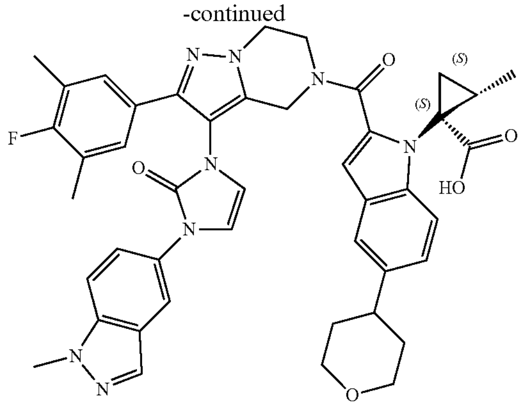

106a

Step A: 1-[(2S)-1-cyano-2-methyl-cyclopropyl]-5-tetrahydropyran-4-yl-indole-2-carboxylic acid

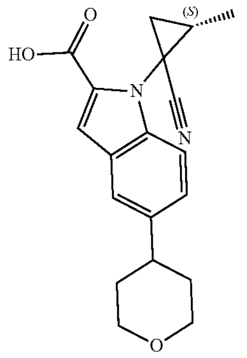

To a suspension of ethyl 1-[(2S)-1-cyano-2-methyl-cyclopropyl]-5-tetrahydropyran-4-yl-indole-2-carboxylate (188 mg, 0.533 mmol) in MeCN (2.0 mL) and $H_2O$ (0.4 mL) was added 1,3,4,6,7,8-Hexahydro-2H-pyrimido[1,2-a]pyrimidine (223 mg, 1.60 mmol). The solution was stirred at 25° C. for 4 hrs. The solution was concentrated to give a residue. The residue was treated with 1N HCl to adjust pH to 5. The mixture was extracted with ethyl acetate (1.5 mL) for four times. The organic layer was washed with water (4 mL), dried by $Na_2SO_4$, and filtered. The filtrate was concentrated to give 1-[(2S)-1-cyano-2-methyl-cyclopropyl]-5-tetrahydropyran-4-yl-indole-2-carboxylic acid (196 mg, crude) as a yellow solid.

Step B: (2S)-1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]-2-methyl-cyclopropanecarbonitrile

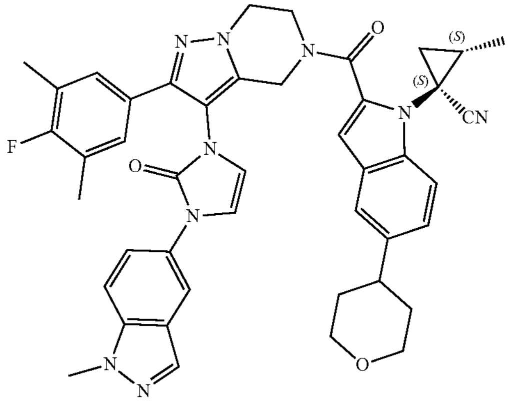

To a suspension of 1-[(2S)-1-cyano-2-methyl-cyclopropyl]-5-tetrahydropyran-4-yl-indole-2-carboxylic acid (50 mg) and 1-[2-(4-fluoro-3,5-dimethyl-phenyl)-4,5,6,7-tetrahydropyrazolo[1,5-a]pyrazin-3-yl]-3-(1-methylindazol-5-yl)imidazol-2-one (71 mg HCl salt) in THF (0.7 mL) was added TEA (78 mg, 0.771 mmol) and $T_3P$ (128 mg, 0.200 mmol, 50% purity). The cloudy solution was stirred at 15° C. for 18 hrs under $N_2$. The cloudy yellow solution was diluted with water (2 mL), and extracted with ethyl acetate (1.5 mL) twice. The organic layer was concentrated to give crude (111 mg) as a yellow gum. The crude was purified by Combi-flash (silica gel, methanol in methyl acetate from 0 to 12%) to give (2S)-1-[2-[2-(4-fluoro-3,5-dimethyl-phenyl)-3-[3-(1-methylindazol-5-yl)-2-oxo-imidazol-1-yl]-6,7-dihydro-4H-pyrazolo[1,5-a]pyrazine-5-carbonyl]-5-tetrahydropyran-4-yl-indol-1-yl]-2-methyl-cyclopropanecarbonitrile (45.0 mg, 43.2% yield for 2 steps) as a white foam.

MS (ESI) m/z 764.1 $(M+H)^+$

Step C: (1S,2S)-1-[2-[2-(4-fluoro-3,5-dimethyl-phenyl)-3-[3-(1-methylindazol-5-yl)-2-oxo-imidazol-1-yl]-6,7-dihydro-4Hpyrazolo[1,5-a]pyrazine-5-carbonyl]-5-tetrahydropyran-4-yl-indol-1-yl]-2-methyl-cyclopropanecarboxylic acid

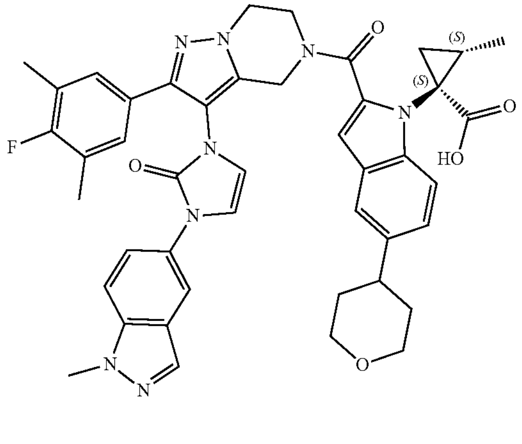

A solution of (2S)-1-[2-[2-(4-fluoro-3,5-dimethyl-phenyl)-3-[3-(1-methylindazol-5-yl)-2-oxo-imidazol-1-yl]-6,7-dihydro-4Hpyrazolo[1,5-a]pyrazine-5-carbonyl]-5-tetrahydropyran-4-yl-indol-1-yl]-2-methyl-cyclopropanecarbonitrile (36 mg, 0.047 mmol) in conc. HCl (0.4 mL) and AcOH (0.2 mL). The solution was stirred at 65° C. for 18 hrs. The solution was concentrated to give crude (82 mg) as a red gum. The crude was purified by prep-HPLC. Column: Phenomenex Gemini C18 250*50 mm*10 um; mobile phase: [water (0.225% FA)-ACN]; B %: 45%-65%, 10 min. The fraction was dried by lyophilization to give (1S,2S)-1-[2-[2-(4-fluoro-3,5-dimethyl-phenyl)-3-[3-(1-methylindazol-5-yl)-2-oxo-imidazol-1-yl]-6,7-dihydro-4Hpyrazolo[1,5-a]pyrazine-5-carbonyl]-5-tetrahydropyran-4-yl-indol-1-yl]-2-methyl-cyclopropanecarboxylic acid (8.95 mg, 24.4% yield) as a white solid.

$^1$H NMR (400 MHz, DMSO-$d_6$, 80° C.) δ ppm 8.09-8.03 (m, 1H), 8.02-7.92 (m, 1H), 7.72-7.62 (m, 2H), 7.52-7.41 (m, 1H), 7.37 (d, J=8.6 Hz, 1H), 7.30-7.21 (m, 3H), 7.14 (d, J=3.2 Hz, 1H), 6.95-6.76 (m, 1H), 6.70-6.62 (m, 1H), 5.05-4.80 (m, 2H), 4.49-4.14 (m, 4H), 4.03 (s, 3H), 4.01-3.93 (m, 2H), 3.55-3.41 (m, 2H), 2.90-2.77 (m, 1H), 2.22 (s, 6H), 2.18-1.56 (m, 7H), 1.19-1.04 (m, 2H), 0.92-0.81 (m, 1H).

Synthesis of key intermediates: tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate Chiral separation: tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate enantiomer 1 and tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate enantiomer 2

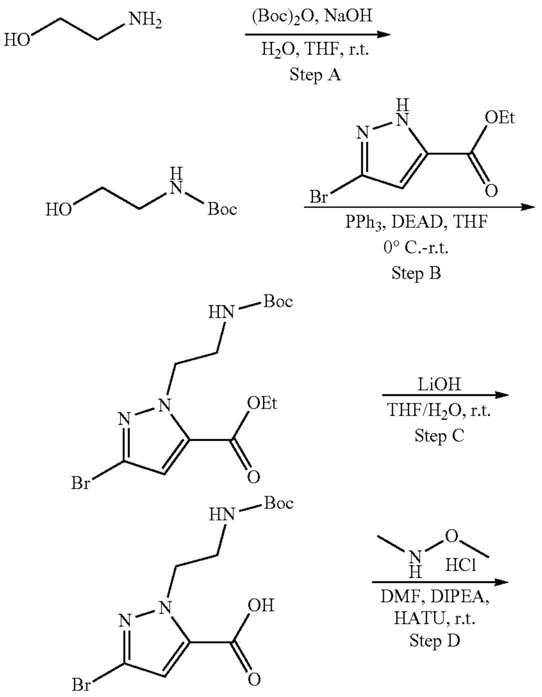

-continued

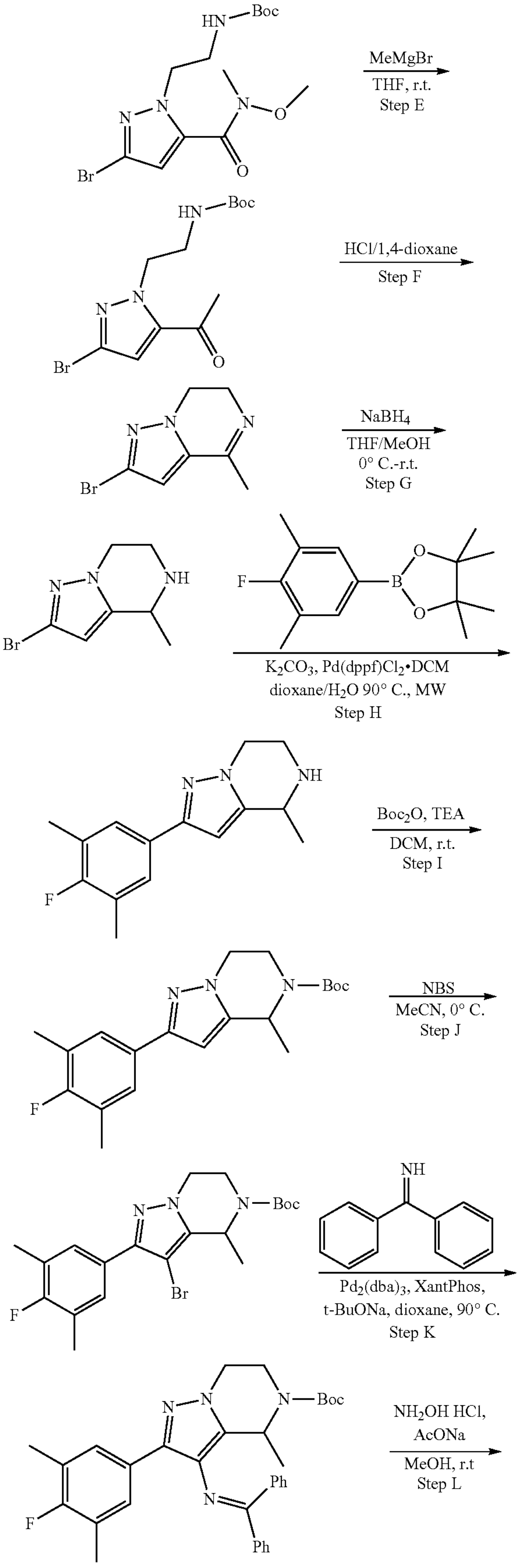

-continued

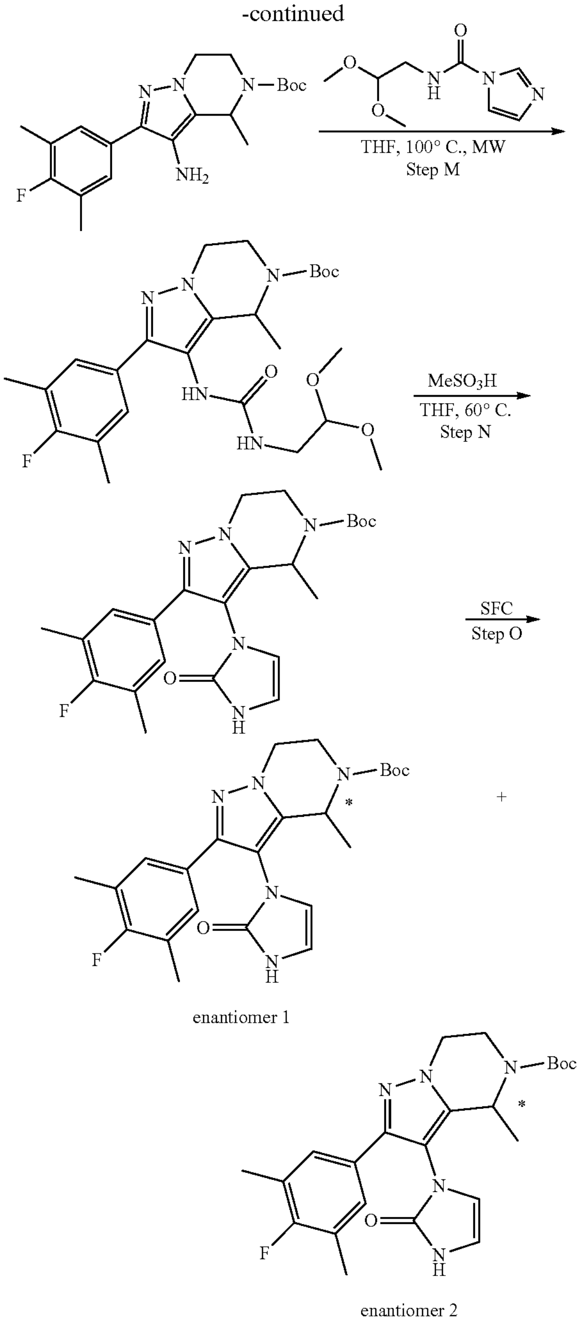

Step A: tert-butyl (2-hydroxyethyl)carbamate

To a solution of 2-aminoethanol (5.00 g, 81.8 mmol) in $H_2O$ (30 mL) were added NaOH (327 mg, 8.19 mmol) and a solution of $(Boc)_2O$ (19.6 g, 90.0 mmol) in THF (30 mL) dropwise. The yellow mixture was stirred at room temperature for 17 hrs. The mixture was extracted with ethyl acetate (30 mL) for three times. The organic layer was washed with brine (60 mL), dried by $Na_2SO_4$, and filtered. The filtrate was concentrated and purified with silica gel column (PE/EtOAc=10:1) to give tert-butyl N-(2-hydroxyethyl)carbamate (12.0 g, 91% yield) as a colorless oil.

$^1H$ NMR (400 MHz, $CDCl_3$) δ ppm 4.96 (br s, 1H) 3.67-3.75 (m, 2H) 3.27-3.32 (m, 2H) 2.43 (br s, 1H), 1.45 (s, 9H).

Step B: ethyl 3-bromo-1-(2-((tert-butoxycarbonyl)amino)ethyl)-1H-pyrazole-5-carboxylate To a solution of ethyl 3-bromo-1H-pyrazole-5-carboxylate (2.00 g, 9.13 mmol) and tert-butyl N-(2-hydroxyethyl) carbamate (1.47 g, 9.13 mmol), and $PPh_3$ (4.78 g, 18.3 mmol) in THF (35 mL) was added DEAD (2.38 g, 13.7 mmol) dropwise at 0~10° C. The yellow solution was stirred at room temperature overnight. The mixture was diluted with water (50 mL) and extracted with ethyl acetate (50 mL) twice. The organic layer was washed with brine (100 mL), dried by $Na_2SO_4$, and filtered. The filtrate was concentrated and purified with silica gel column (PE/EtOAc=10:1) to afford ethyl 3-bromo-1-(2-((tert-butoxycarbonyl)amino)ethyl)-1H-pyrazole-5-carboxylate (2.60 g, 78% yield) as a white solid. LC-MS: m/z 306.1, 308.1 $(M-56+H)^+$.

Step C: 3-bromo-1-(2-((tert-butoxycarbonyl)amino)ethyl)-1H-pyrazole-5-carboxylic acid To a mixture of ethyl 3-bromo-1-(2-((tert-butoxycarbonyl)amino)ethyl)-1H-pyrazole-5-carboxylate (2.60 g, 7.18 mmol) in THF/$H_2O$ (40 mL/10 mL) was added LiOH (344 mg, 14.4 mmol) at 0° C. slowly. The mixture was stirred at room temperature overnight. The mixture was concentrated to remove THF. Then the mixture was adjusted to pH=4 with 1 M HCl aqueous solution. The mixture was filtered, and the filter cake was dried to give 3-bromo-1-(2-((tert-butoxycarbonyl)amino)ethyl)-1H-pyrazole-5-carboxylic acid as a white solid (2.35 g, 98% yield). LC-MS: m/z 278.1, 280.1 $(M-56+H)^+$.

Step D: tert-butyl (2-(3-bromo-5-(methoxy(methyl)carbamoyl)-1H-pyrazol-1-yl)ethyl)carbamate To a solution of 3-bromo-1-(2-((tert-butoxycarbonyl)amino)ethyl)-1H-pyrazole-5-carboxylic acid (3.40 g, 10.2 mmol), N,O-dimethylhydroxylamine hydrochloride (1.48 g, 15.3 mmol), and HATU (5.80 g, 15.3 mmol) in DMF (35 mL) was added DIPEA (3.90 g, 30.5 mmol) dropwise at 0° C. The solution was stirred at room temperature overnight. The mixture was diluted with water (50 mL) and extracted with ethyl acetate (50 mL) twice. The organic layer was washed with brine (80 mL*6), dried by $Na_2SO_4$, and filtered. The filtrate was concentrated to give tert-butyl (2-(3-bromo-5-(methoxy(methyl)carbamoyl)-1H-pyrazol-1-yl)ethyl)carbamate (3.00 g, 78% yield, crude) as a yellow solid. LC-MS: m/z 276.8, 278.8 $(M-100+H)^+$.

Step E: tert-butyl (2-(5-acetyl-3-bromo-1H-pyrazol-1-yl)ethyl)carbamate

To a mixture of tert-butyl (2-(3-bromo-5-(methoxy(methyl)carbamoyl)-1H-pyrazol-1-yl)ethyl)carbamate (3.00 g, 7.95 mmol) in THF (30 mL) was added MeMgBr (3 M in THF, 10.6 mL, 31.8 mmol) at 0° C. under $N_2$ atmosphere slowly. The mixture was stirred at room temperature overnight. The mixture was quenched with $NH_4Cl$ (80 mL) and extracted with ethyl acetate (80 mL) twice. The organic layer was dried by $Na_2SO_4$ and filtered. The filtrate was concentrated, the residue was purified with silica gel column (PE/EtOAc=7:1) to give tert-butyl (2-(5-acetyl-3-bromo-1H-pyrazol-1-yl)ethyl) carbamate (2.12 g, 80% yield, crude) as a white solid. LC-MS: m/z 276.1, 278.1 $(M-56+H)^+$.

Step F: 2-bromo-4-methyl-6,7-dihydropyrazolo[1,5-a]pyrazine

To a mixture of tert-butyl (2-(5-acetyl-3-bromo-1H-pyrazol-1-yl)ethyl)carbamate (2.80 g, 8.43 mmol) in dioxane (30 mL) was added HCl-dioxane (4 M, 18 mL). The mixture was stirred at room temperature overnight. The mixture was concentrated, diluted with $NaHCO_3$ (aq) (30 mL), and extracted with ethyl acetate (50 mL) twice. The organic layer was washed with brine (80 mL*2), dried by $Na_2SO_4$, and filtered. The filtrate was concentrated to give 2-bromo-4-methyl-6,7-dihydropyrazolo[1,5-a]pyrazine (1.90 g, 80% yield, crude) as a yellow solid. LC-MS: m/z 214.0, 216.0 $(M+H)^+$.

Step G: 2-bromo-4-methyl-4,5,6,7-tetrahydropyrazolo[1,5-a]pyrazine

To a mixture of 2-bromo-4-methyl-6,7-dihydropyrazolo[1,5-a]pyrazine (900 mg, 4.20 mmol) in MeOH (8 mL) was added $NaBH_4$ (636 mg, 16.8 mmol) at 0° C. under $N_2$ atmosphere slowly. The mixture was stirred at room temperature for 1 hr. The mixture was diluted with water (15 mL) and extracted with DCM (20 mL) twice. The organic layer was dried by $Na_2SO_4$ and filtered. The filtrate was concentrated and purified with silica gel column (PE/EtOAc=40:1) to give 2-bromo-4-methyl-4,5,6,7-tetrahydropyrazolo[1,5-a]pyrazine as a yellow solid (782 mg, 86% yield).

$^1H$ NMR (400 MHz, $CDCl_3$) δ ppm 6.02 (s, 1H), 3.94-4.18 (m, 3H), 3.34-3.45 (m, 1H), 3.18-3.25 (m, 1H), 1.42 (d, J=6.4 Hz, 3H).

Step H: 2-(4-fluoro-3,5-dimethylphenyl)-4-methyl-4,5,6,7-tetrahydropyrazolo[1,5-a]pyrazine To a mixture of 2-(4-fluoro-3,5-dimethylphenyl)-4,4,5,5-tetramethyl-1,3,2-dioxaborolane (800 mg, 3.19 mmol) in dioxane/$H_2O$ (10 mL/2 mL) were added 2-bromo-4-methyl-4,5,6,7-tetrahydropyrazolo[1,5-a]pyrazine (760 mg, 3.52 mmol), $K_2CO_3$ (1.30 g, 9.59 mmol), and Pd(dppf)$Cl_2$·DCM (160 mg, 0.196 mmol) at room temperature. The mixture was stirred at 90° C. for 2 hrs under microwave irradiation under $N_2$. The mixture was filtered, and the filter cake was washed with ethyl acetate (20 mL). The filtrate was dried over $Na_2SO_4$, and concentrated. The residue was purified with silica gel column (PE/EtOAc=40:1 to 20:1) to give 2-(4-fluoro-3,5-dimethylphenyl)-4-methyl-4,5,6,7-tetrahydropyrazolo[1,5-a]pyrazine as a black oil (700 mg, 84% yield). LC-MS: m/z 260.2 $(M+H)^+$.

Step I: tert-butyl 2-(4-fluoro-3,5-dimethylphenyl)-4-methyl-6,7-dihydropyrazolo[1,5-a]pyrazine-5(4H)-carboxylate To a solution of 2-(4-fluoro-3,5-dimethylphenyl)-4-methyl-4,5,6,7-tetrahydropyrazolo[1,5-a]pyrazine (700 mg, 2.70 mmol) in DCM (7 mL) were added TEA (822 mg, 8.10 mmol) and $(Boc)_2O$ (1.17 g, 5.40 mmol) at 0° C. The mixture was stirred at room temperature overnight. The mixture was concentrated to give crude as a deep yellow gum. The crude was purified with silica gel column (PE/EtOAc=40:1) to give tert-butyl 2-(4-fluoro-3,5-dimethylphenyl)-4-methyl-6,7-dihydropyrazolo[1,5-a]pyrazine-5(4H)-carboxylate as a colorless oil (940 mg, 97% yield). LC-MS: m/z 360.4 $(M+H)^+$.

Step J: tert-butyl 3-bromo-2-(4-fluoro-3,5-dimethylphenyl)-4-methyl-6,7-dihydropyrazolo[1,5-a]pyrazine-5(4H)-carboxylate To a solution of tert-butyl 2-(4-fluoro-3,5-dimethylphenyl)-4-methyl-6,7-dihydropyrazolo[1,5-a]pyrazine-5(4H)-carboxylate (940 mg, 2.61 mmol) in MeCN (20 mL) was added NBS (465 mg, 2.61 mmol) in MeCN (5 mL) at 0° C. under $N_2$. The solution was stirred at 0° C. for 1 hr under $N_2$. The mixture was concentrated and purified with silica gel column (PE/EtOAc=10:1) to give tert-butyl 3-bromo-2-(4-fluoro-3,5-dimethylphenyl)-4-methyl-6,7-dihydropyrazolo[1,5-a]pyrazine-5(4H)-carboxylate as a white solid (470 mg, 42% yield). LC-MS: m/z 438.3, 440.3 $(M+H)^+$.

Step K: tert-butyl 3-((diphenylmethylene)amino)-2-(4-fluoro-3,5-dimethylphenyl)-4-methyl-6,7-dihydropyrazolo[1,5-a]pyrazine-5(4H)-carboxylate To a solution of tert-butyl 3-bromo-2-(4-fluoro-3,5-dimethylphenyl)-4-methyl-6,7-dihydropyrazolo[1,5-a]pyrazine-5(4H)-carboxylate (280 mg, 0.638 mmol) and diphenylmethanimine (173 mg, 0.958 mmol) in dioxane (25 mL) were added t-BuONa (245 mg, 2.55 mmol), $Pd_2(dba)_3$ (59.0 mg, 0.0640 mmol), and Xantphos (60.0 mg, 0.102 mmol). The suspension was stirred at 90° C. for 16 hrs under $N_2$. The mixture was filtered, and the filter cake was washed with ethyl acetate (20 mL). The organic layer was concentrated and purified with silica gel column (PE/EtOAc=20:1) to give tert-butyl 3-((diphenylmethylene)amino)-2-(4-fluoro-3,5-dimethylphenyl)-4-methyl-6,7-dihydropyrazolo[1,5-a]pyrazine-5(4H)-carboxylate as a yellow solid (212 mg, 61% yield).

LC-MS: m/z 539.4 $(M+H)^+$.

Step L: tert-butyl 3-amino-2-(4-fluoro-3,5-dimethylphenyl)-4-methyl-6,7-dihydropyrazolo[1,5-a]pyrazine-5(4H)-carboxylate To a solution of tert-butyl 3-((diphenylmethylene)amino)-2-(4-fluoro-3,5-dimethylphenyl)-4-methyl-6,7-dihydropyrazolo[1,5-a]pyrazine-5(4H)-carboxylate (380 mg, 0.706 mmol) in MeOH (7 mL) was added NaOAc (174 mg, 2.12 mmol). The mixture was stirred at room temperature for 10 mins, and then $NH_2OH$·HCl (98.0 mg, 1.41 mmol) was added under $N_2$. The yellow cloudy solution was stirred at room temperature for 48 hrs. The mixture was concentrated to remove MeOH, and then diluted with water (10 mL). The mixture was extracted with ethyl acetate (15 mL) twice. The organic layer was washed with brine (15 mL), dried by $Na_2SO_4$, and filtered. The filtrate was concentrated and purified with silica gel column (PE/EtOAc=20:1) to give tert-butyl 3-amino-2-(4-fluoro-3,5-dimethylphenyl)-4-methyl-6,7-dihydropyrazolo[1,5-a]pyrazine-5(4H)-carboxylate as a yellow solid (210 mg, 79% yield). LC-MS: m/z 375.3 (M+H).

Step M: tert-butyl 3-(3-(2,2-dimethoxyethyl)ureido)-2-(4-fluoro-3,5-dimethylphenyl)-4-methyl-6,7-dihydropyrazolo[1,5-a]pyrazine-5(4H)-carboxylate A solution of tert-butyl 3-amino-2-(4-fluoro-3,5-dimethylphenyl)-4-methyl-6,7-dihydropyrazolo[1,5-a]pyrazine-5(4H)-carboxylate (140 mg, 0.374 mmol) and N-(2,2-dimethoxyethyl)-1H-imidazole-1-carboxamide (149 mg, 0.748 mmol) in THF (2 mL) was stirred at 100° C. for 2 hrs under microwave irradiation. The solution was concentrated and purified by prep-TLC (PE:EtOAc=1:1) to give tert-butyl 3-(3-(2,2-dimethoxyethyl)ureido)-2-(4-fluoro-3,5-dimethylphenyl)-4-methyl-6,7-dihydropyrazolo[1,5-a]pyrazine-5(4H)-carboxylate (170 mg, 90% yield) as a yellow solid. LC-MS: m/z 506.4 $(M+H)^+$.

Step N: tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate To a solution of tert-butyl 3-(3-(2,2-dimethoxyethyl) ureido)-2-(4-fluoro-3,5-dimethylphenyl)-4-methyl-6,7-dihydropyrazolo[1,5-a]pyrazine-5(4H)-carboxylate (170 mg, 0.336 mmol) in THF (5 mL) was added methanesulfonic acid (32.0 mg, 0.336 mmol) at room temperature. The solution was stirred at 60° C. for 1.5 hrs. The mixture was diluted with 1N $NaHCO_3$ aqueous solution (5 mL) and extracted with ethyl acetate (5 mL*3). The organic layer was dried by $Na_2SO_4$ and filtered. The filtrate was concentrated and purified by silica gel column (PE/EtOAc=1/1) to give tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate (130 mg, 88% yield) as a yellow solid. LC-MS: m/z 442.3 $(M+H)^+$.

Step O: Chiral separation of tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate Chiral separation of tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate (110 mg) using SFC (column: AD-H, elution: $CO_2$:EtOH (0.1% DEA)=80:20; Flow rate: 2.5 mL/min; Temperature: 25° C.) giving two enantiomers.

enantiomer 1: tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate (40 mg, 36% yield) Retention time: 2.77 mins. LC-MS: m/z 442.3 $(M+H)^+$.

enantiomer 2: tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate (35 mg, 32% yield) Retention time: 3.84 mins. LC-MS: m/z 442.3 $(M+H)^+$.

Example 5: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (Compound 108a)

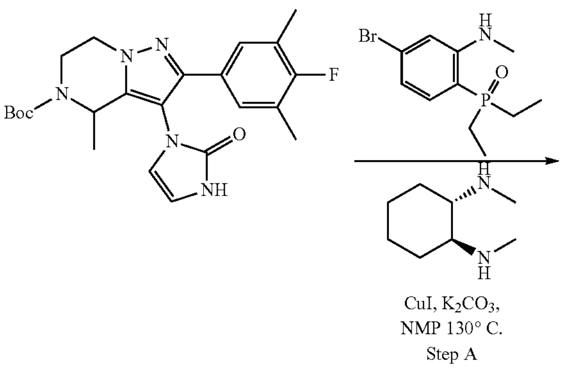

-continued

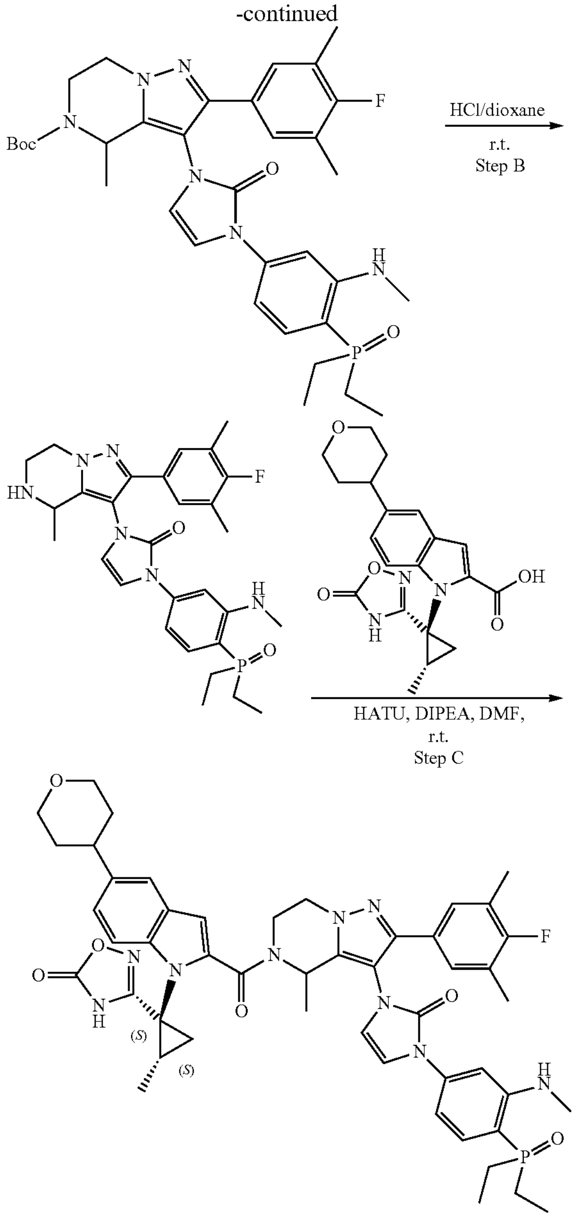

108a

Step A: tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate A mixture of (tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate (50.0 mg, 0.110 mmol), (4-bromo-2-(methylamino)phenyl)diethylphosphine oxide (36.0 mg, 0.120 mmol), (1S,2S)—$N^1$,$N^2$-dimethylcyclohexane-1,2-diamine (25.0 mg, 0.170 mmol), CuI (32.0 mg, 0.170 mmol) and $K_2CO_3$ (31.0 mg, 0.220 mmol) in NMP (3 mL) was stirred at 130° C. for 3 hrs. The mixture was diluted with water (10 mL), and extracted with ethyl acetate (10 mL*3). The organic layer was washed with brine (10 mL), dried and concentrated. The residue was purified by column to give tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate (53.0 mg, 72% yield). LC-MS: m/z 651.2 (M+H)$^+$.

Step B: 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one A mixture of tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate (57.0 mg, 0.0880 mmol) in 4 mol/L hydrogen chloride-1,4-dioxane solution (2 mL) was stirred at room temperature overnight. LCMS showed the reaction was completed. The mixture was quenched with $Na_2CO_3$ (aq.) (10 mL) and extracted with DCM (10 mL*3). The organic layer was washed with bine (10 mL), dried and concentrated to give 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one as an off-white solid (39.0 mg, crude), which was used in next step without purification. LC-MS: m/z 551.2 (M+H)$^+$.

Step C: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one A mixture of 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one (39 mg, crude), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (30.0 mg, 0.0800 mmol), HATU (81.0 mg, 0.210 mmol), and DIPEA (55 mg, 0.42 mmol) in DMF (4 mL) was stirred at room temperature overnight. The mixture was diluted with water (10 mL) and extracted with ethyl acetate (10 mL*3). The organic layer was washed with brine (10 mL), dried and concentrated. The residue was purified by prep-HPLC (0.1% HCl in water and acetonitrile) to give 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one as a white solid (18.0 mg, 28% yield). $^1$H NMR (400 MHz, DMSO-$d_6$, 80° C.) δ ppm 11.73 (br.s, 1H), 7.49 (d, J=7.6 Hz, 1H), 7.40 (d, J=8.0 Hz, 1H), 7.10-7.30 (m, 5H), 6.90-7.02 (m, 2H), 6.86 (s, 1H), 6.72 (s, 1H), 5.70 (br.s, 1H), 4.52-4.75 (m, 1H), 4.20-4.45 (m, 2H), 3.97 (d, J=10.8 Hz, 2H), 3.80-3.97 (m, 1H), 3.43-3.53 (m, 2H), 2.81-2.97 (m, 2H), 2.72 (s, 3H), 2.18 (s, 6H), 1.85-1.97 (m, 4H), 1.67-1.80 (m, 5H), 1.55-1.66 (m, 1H), 1.40-1.53 (m, 3H), 1.20-1.35 (m, 3H), 1.10-1.22 (br.s, 1H), 0.97-1.09 (m, 6H). $^{31}$P NMR (162 MHz, DMSO-d6) δ ppm 53.08. $^{19}$F NMR (377 MHz, DMSO-d6) δ ppm −122.01, −122.08. LC-MS: m/z 458.8 (M/2+H)$^+$.

Example 6: 3-((1S,2S)-1-(2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (Compound 109a)

109a

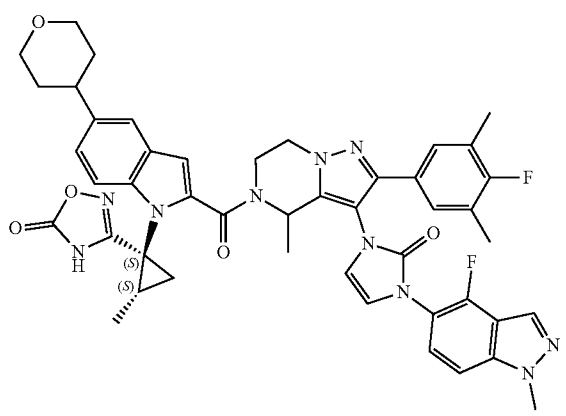

Compound 109a was synthesized following the route of Example 5, using 5-bromo-4-fluoro-1-methyl-1H-indazole in step A.

$^1$H NMR (400 MHz, DMSO-$d_6$, 80° C.) δ ppm 11.52-11.90 (m, 1H), 8.20 (s, 1H), 7.49-7.55 (m, 2H), 7.38-7.48 (m, 2H), 7.23-7.30 (m, 3H), 6.86-6.96 (m, 2H), 6.69 (t, J=2.4 Hz, 1H), 5.72 (br.s, 1H), 4.57-4.65 (m, 1H), 4.30-4.40 (m, 2H), 4.09 (s, 3H), 3.82-4.00 (m, 3H), 3.42-3.60 (m, 2H), 2.80-2.93 (m, 1H), 2.23 (s, 6H), 1.92-2.04 (m, 1H), 1.60-1.85 (m, 5H), 1.44-1.58 (m, 3H), 1.05-1.32 (m, 4H). $^{19}$F NMR (377 MHz, DMSO-d6) δ ppm −122.10, −126.78. LC-MS: m/z 855.7 (M+H)$^+$.

Example 7: 3-(1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)cyclopropyl)-1,2,4-oxadiazol-5(4H)-one (Compound 104)

104

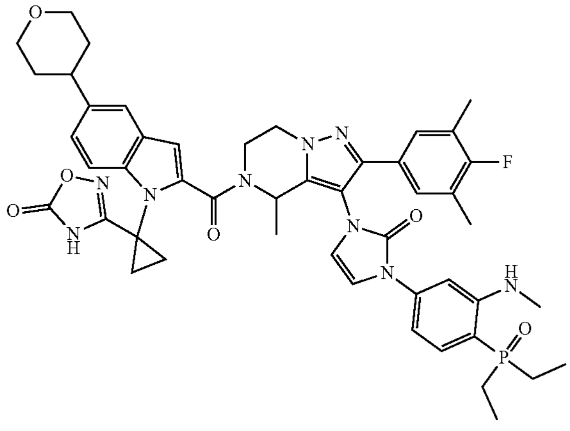

Compound 104 was synthesized following the route of Example 5, using 1-(1-(5-oxo-4,5-dihydro-1,2,4-oxadiazol-3-yl)cyclopropyl)-5-(tetrahydro-2H-pyran-4-yl)-1H-indole-2-carboxylic acid in step C.

$^{1}$H NMR (400 MHz, DMSO-$d_6$, 80° C.) δ ppm 11.80 (br.s, 1H), 7.45-7.51 (m, 2H), 7.15-7.26 (m, 5H), 6.89-6.98 (m, 2H), 6.86 (s, 1H), 6.72 (d, J=2.8 Hz, 1H), 5.70 (s, 1H), 4.60 (d, J=14.4 Hz, 1H), 4.24-4.35 (m, 2H), 3.97 (d, J=10.8 Hz, 2H), 3.78-3.90 (m, 1H), 3.43-3.52 (m, 2H), 2.80-2.91 (m, 1H), 2.72 (s, 3H), 2.18 (s, 6H), 1.85-1.97 (m, 4H), 1.62-1.82 (m, 8H), 1.47-1.60 (m 1H), 1.43 (d, J=6.4 Hz, 3H), 0.95-1.07 (m, 6H). $^{31}$P NMR (162 MHz, DMSO-d6) δ ppm 52.96. $^{19}$F NMR (377 MHz, DMSO-d6) δ ppm −122.09. LC-MS: m/z 902.4 $(M+H)^+$.

Example 8: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (single diastereomer 1, Compound 108a)

108a

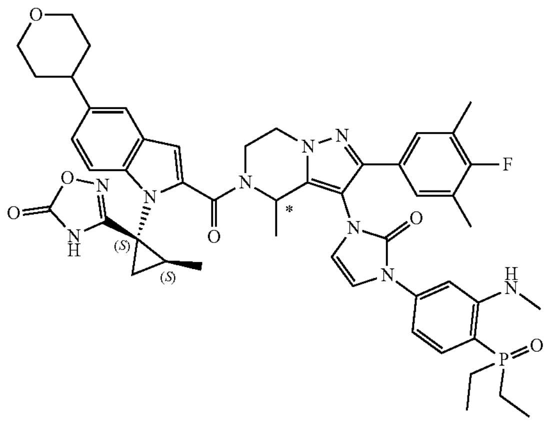

single diastereomer 1

Compound 108a was synthesized following the route of Example 5, using tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate enantiomer 1 in step A.

$^{1}$H NMR (400 MHz, DMSO-$d_6$, 80° C.) δ ppm 11.76 (s, 1H), 7.48 (s, 1H), 7.40 (d, J=8.4 Hz, 1H), 7.14-7.29 (m, 5H), 6.89-6.99 (m, 2H), 6.86 (s, 1H), 6.72 (d, J=2.8 Hz, 1H), 5.71 (br.s, 1H), 4.50-4.70 (m, 1H), 4.25-4.40 (m, 2H), 3.97 (d, J=10.8 Hz, 2H), 3.80-3.92 (m, 1H), 3.42-3.53 (m, 2H), 2.79-2.97 (m, 2H), 2.72 (s, 3H), 2.18 (d, J=1.2 Hz, 6H), 1.85-2.04 (m, 5H), 1.69-1.79 (m, 4H), 1.59-1.69 (m, 1H), 1.49-1.59 (m, 1H), 1.45 (d, J=6.8 Hz, 3H), 1.20-1.35 (m, 3H), 0.96-1.09 (m, 6H). $^{31}$P NMR (162 MHz, DMSO-d6) δ ppm 52.93. $^{19}$F NMR (377 MHz, DMSO-d6) δ ppm −122.08. LC-MS: m/z 916.4 $(M+H)^+$.

Example 9: 3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(4,4-difluorocyclohexyl)-1H-indol-1-yl)-2-methylcyclopropyl)-1,2,4-oxadiazol-5(4H)-one (single diastereomer 2, Compound 116a)

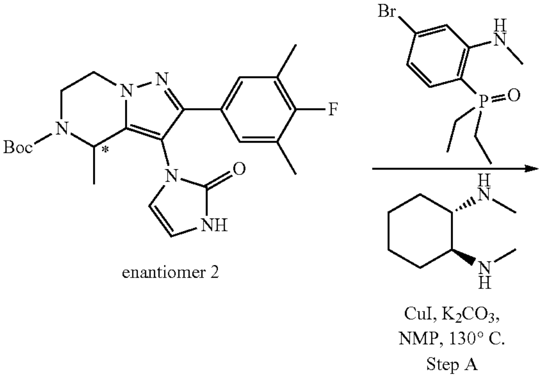

enantiomer 2

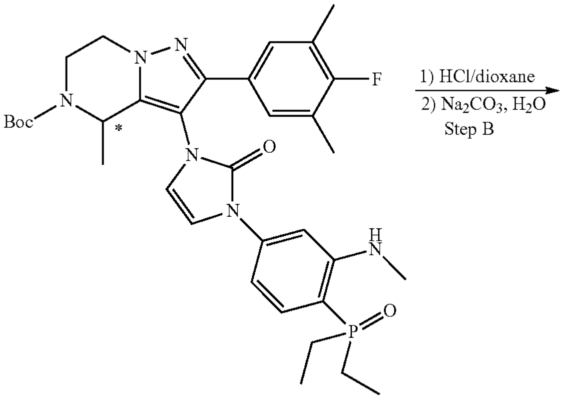

enantiomer 2-A

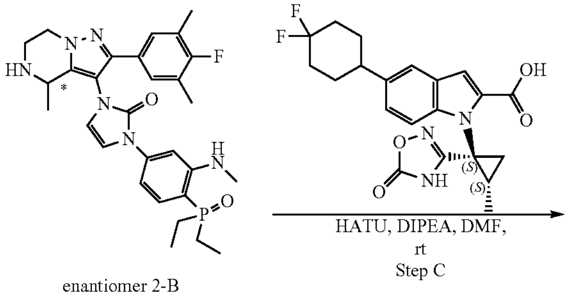

enantiomer 2-B

-continued

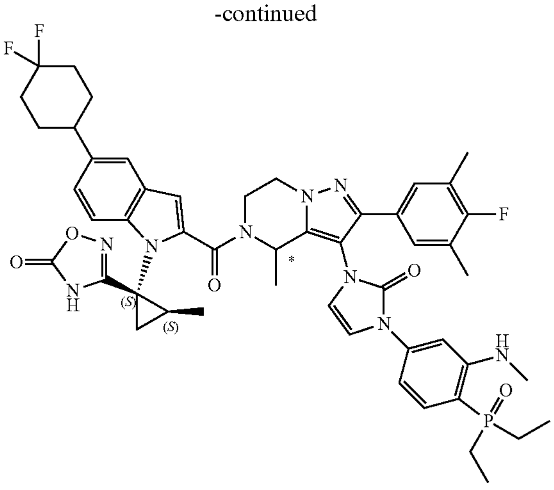

116a
single diastereomer 2

Step A: tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate (enantiomer 2-A)

A mixture of tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate enantiomer 2 (100 mg, 0.230 mmol), (4-bromo-2-(methylamino)phenyl)diethylphosphine oxide (73.0 mg, 0.253 mmol), (1S,2S)—$N^1$,$N^2$-dimethylcyclohexane-1,2-diamine (51.0 mg, 0.345 mmol), CuI (66.0 mg, 0.345 mmol) and $K_2CO_3$ (22.0 mg, 0.460 mmol) in NMP (3 mL) was stirred at 130° C. for 3 h. The mixture was added water and extracted with ethyl acetate. The organic layer was washed with brine, dried and concentrated. The residue was purified with Prep-TLC (DCM/MeOH=20/1) to give tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate as a yellow solid (enantiomer 2-A) (100 mg, 68% yield). LC-MS: m/z 651.4 $(M+H)^+$.

Step B: 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one (enantiomer 2-B)

A mixture of tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-6,7-dihydropyrazolo[1,5-a]pyrazine-5(4H)-carboxylate (enantiomer 2-A)(100 mg, 0.150 mmol) in 4 mol/L hydrogen chloride/1,4-dioxane solution was stirred at room temperature for 4 h. LCMS showed the reaction was completed. The mixture was quenched with $Na_2CO_3$ (2 M aq.) and extracted with DCM. The organic layers were washed with brine, dried, and concentrated to give 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one (enantiomer 2-B) as a yellow oil, which was used in next step without purification (80.0 mg crude). LC-MS: m/z 551.3 $(M+H)^+$.

Step C: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(4,4-difluorocyclohexyl)-1H-indol-1-yl)-2-methylcyclopropyl)-1,2,4-oxadiazol-5(4H)-one (Compound 116a, single diastereomer 2)

A mixture of 1-(4-(diethylphosphoryl)-3-(methylamino)phenyl)-3-(2-(4-fluoro-3,5-dimethylphenyl)-4-methyl-4,5,6,7-tetrahydropyrazolo[1,5-a]pyrazin-3-yl)-1H-imidazol-2(3H)-one (enantiomer 2-B) (80.0 mg, crude), 5-(4,4-difluorocyclohexyl)-1-((1S,2S)-2-methyl-1-(5-oxo-4,5-dihydro-1,2,4-oxadiazol-3-yl)cyclopropyl)-1H-indole-2-carboxylic acid (69.0 mg, 0.165 mmol), HATU (171 mg, 0.450 mmol), and DIPEA (116 mg, 0.900 mmol) in DMF (5 mL) was stirred at room temperature overnight. The mixture was added water and extracted with ethyl acetate. The organic layer was washed with brine, dried and concentrated. The residue was purified with Prep-HPLC to give 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(4,4-difluorocyclohexyl)-1H-indol-1-yl)-2-methylcyclopropyl)-1,2,4-oxadiazol-5(4H)-one (Compound 116a, single diastereomer 2) as a white solid (63.0 mg, 46% yield). $^1H$ NMR (400 MHz, DMSO-$d_6$, 80° C.) δ ppm 11.46 (br.s, 1H), 7.51 (s, 1H), 7.40 (d, J=8.8 Hz, 1H), 7.13-7.30 (m, 5H), 6.92-7.00 (m, 3H), 6.72 (d, J=2.4 Hz, 1H), 5.70 (br.s, 1H), 4.61 (d, J=14.0 Hz, 1H), 4.28-4.50 (m, 2H), 3.85-3.96 (m, 1H), 2.80 (t, J=11.6 Hz, 1H), 2.71 (s, 3H), 2.18 (d, J=1.6 Hz, 6H), 2.06-2.16 (m, 2H), 1.85-2.06 (m, 9H), 1.66-1.85 (m, 4H), 1.56-1.65 (m, 1H), 1.48 (s, 3H), 1.17 (s, 3H), 0.95-1.08 (m, 6H). $^{31}P$ NMR (162 MHz, DMSO-d6) δ ppm 52.92. $^{19}F$ NMR (377 MHz, DMSO-d6) S ppm −88.94, −88.97, −89.57, −89.59, −99.73, −100.35, −122.04. LC-MS: m/z 476.0 $(M/2+H)^+$.

Example 10: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-((S)-2,2-dimethyltetrahydro-2H-pyran-4-yl)-1H-indol-1-yl)-2-methylcyclopropyl)-1,2,4-oxadiazol-5(4H)-one (single diastereomer 2, Compound 113a)

113a

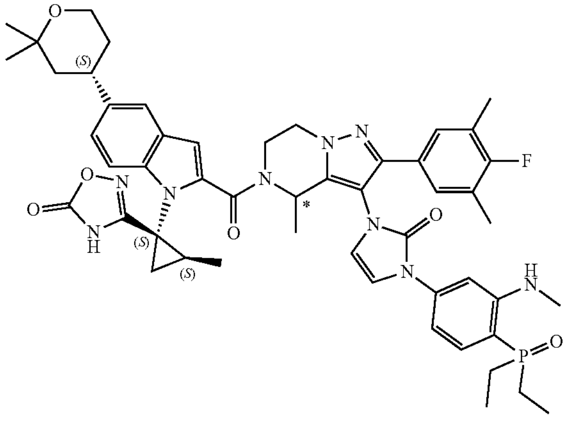

single diastereomer 2

(Compound 113a) was synthesized following the route in Example 9, using 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid in step C.

$^1$H NMR (400 MHz, DMSO-$d_6$, 80° C.) δ ppm 11.51 (br.s, 1H), 7.50 (s, 1H), 7.40 (d, J=8.4 Hz, 1H), 7.13-7.28 (m, 5H), 6.90-7.00 (m, 3H), 6.72 (d, J=2.4 Hz, 1H), 5.70 (br.s, 1H), 4.56-4.65 (m, 1H), 4.27-4.46 (m, 2H), 3.82-3.97 (m, 1H), 3.72 (d, J=7.6 Hz, 2H), 2.97-3.08 (m, 2H), 2.72 (s, 3H), 2.19 (s, 6H), 1.85-1.97 (m, 4H), 1.75-1.88 (m, 1H), 1.66-1.75 (m, 3H), 1.42-1.68 (m, 6H), 1.28 (s, 3H), 1.10-1.23 (m, 6H), 0.97-1.09 (m, 6H). $^{31}$P NMR (162 MHz, DMSO-d6) δ ppm 52.93. $^{19}$F NMR (377 MHz, DMSO-d6) δ ppm −122.03. LC-MS: m/z 472.7 $(M/2+H)^+$.

Example 11: 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-1H-indol-1-yl)-2-methylcyclopropyl)-1,2,4-oxadiazol-5(4H)-one (single diastereomer 2, Compound 117a)

117a

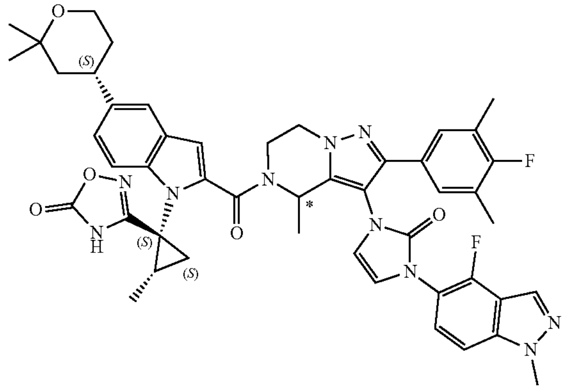

single diastereomer 2

(Compound 117a) was synthesized following the route in Example 9, using 5-bromo-4-fluoro-1-methyl-1H-indazole in step A and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid in step C.

$^1$H NMR (400 MHz, DMSO-$d_6$, 80° C.) δ ppm 11.50 (br.s, 1H), 8.20 (s, 1H), 7.48-7.57 (m, 2H), 7.36-7.49 (m, 2H), 7.25-7.27 (m, 3H), 6.93 (s, 2H), 6.69 (d, J=2.8 Hz, 1H), 5.72 (br.s, 1H), 4.61 (d, J=12.8 Hz, 1H), 4.27-4.54 (m, 2H), 4.09 (s, 3H), 3.85-3.98 (m, 1H), 3.71-3.76 (m, 2H), 2.96-3.10 (m, 1H), 2.23 (s, 6H), 1.82 (br.s, 1H), 1.66-1.75 (m, 3H), 1.42-1.66 (m, 6H), 1.28 (s, 3H), 1.14-1.23 (m, 6H). $^{19}$F NMR (377 MHz, DMSO-d6) δ ppm −122.08, −126.79.

Example 12: 3-((1S,2S)-1-(2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (single diastereomer 2, Compound 110a)

110a

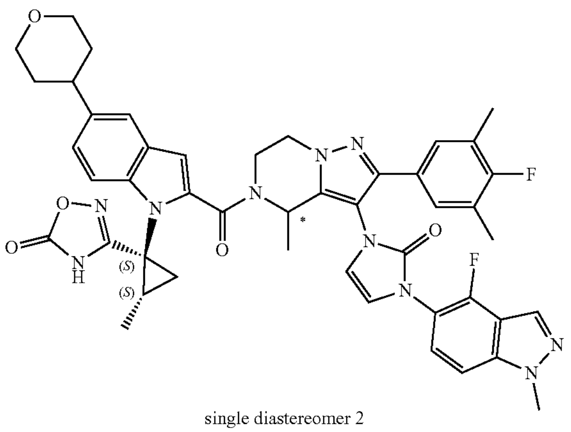

single diastereomer 2

(Compound 110a) was synthesized following the route in Example 9, using 5-bromo-4-fluoro-1-methyl-1H-indazole in step A and 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid in step C.

$^1$H NMR (400 MHz, DMSO-$d_6$, 80° C.) δ ppm 8.22 (s, 1H), 7.50-7.61 (m, 2H), 7.40-7.50 (m, 2H), 7.25-7.32 (m, 3H), 6.94 (s, 2H), 6.72 (d, J=2.4 Hz, 1H), 5.75 (br.s, 1H), 4.63 (d, J=12.8 Hz, 1H), 4.27-4.50 (m, 2H), 4.11 (s, 3H), 3.85-4.03 (m, 3H), 3.45-3.55 (m, 2H), 2.82-2.96 (m, 1H), 2.25 (s, 6H), 1.80-1.93 (m, 1H), 1.70-1.80 (m, 5H), 1.60-1.70 (m, 1H), 1.50-1.60 (m, 3H), 1.15-1.30 (m, 3H). $^{19}$F NMR (377 MHz, DMSO-d6) δ ppm −122.09, −126.79. LC-MS: m/z 855.4 $(M+H)^+$.

Example 13: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (single diastereomer 2, Compound 111a)

111a

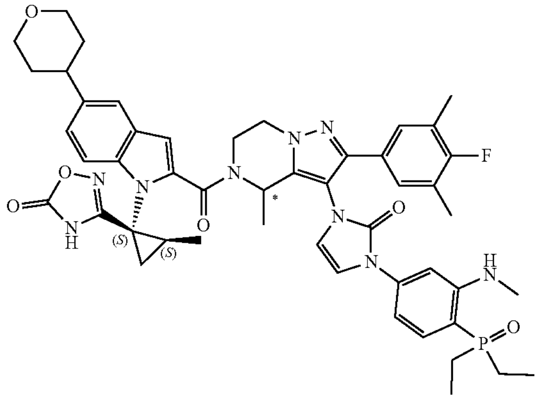

single diastereomer 2

(Compound 111a) was synthesized following the route in Example 9, using 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid in step C.

$^{1}$H NMR (400 MHz, DMSO-$d_6$, 80° C.) δ ppm 11.48 (br.s, 1H), 7.50 (s, 1H), 7.40 (d, J=8.8 Hz, 1H), 7.15-7.29 (m, 5H), 6.80-7.10 (m, 3H), 6.74 (d, J=2.4 Hz, 1H), 5.60-5.80 (m, 1H), 4.62 (d, J=15.2 Hz, 1H), 4.28-4.50 (m, 2H), 3.85-4.05 (m, 3H), 3.45-3.55 (m, 2H), 2.80-2.95 (m, 1H), 2.72 (s, 3H), 2.18 (s, 6H), 1.89-2.00 (m, 5H), 1.66-1.80 (m, 6H), 1.58-1.68 (m, 1H), 1.41-1.55 (m, 3H), 1.10-1.30 (m, 3H), 0.96-1.10 (m, 6H). $^{31}$P NMR (162 MHz, DMSO-d6) δ ppm 52.92. $^{19}$F NMR (377 MHz, DMSO-d6) δ ppm −122.02. LC-MS: m/z 458.8 $(M/2+H)^{+}$.

Example 14: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-morpholino-1H-indol-1-yl)-2-methylcyclopropyl)-1,2,4-oxadiazol-5(4H)-one (single diastereomer 2, Compound 114a)

114a

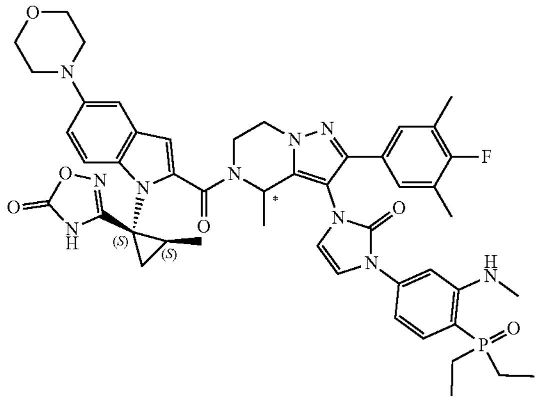

single diastereomer 2

(Compound 114a) was synthesized following the route in Example 9, using 1-((1S,2S)-2-methyl-1-(5-oxo-4,5-dihydro-1,2,4-oxadiazol-3-yl)cyclopropyl)-5-morpholino-1H-indole-2-carboxylic acid in step C.

$^{1}$H NMR (400 MHz, DMSO-$d_6$, 80° C.) δ ppm 11.49 (br.s, 1H), 7.39-7.52 (m, 2H), 7.20-7.39 (m, 5H), 6.80-7.10 (m, 3H), 6.74 (s, 1H), 5.71 (br.s, 1H), 4.55-4.75 (m, 1H), 4.37-4.51 (m, 2H), 3.80-4.05 (m, 5H), 3.15-3.55 (m, 5H), 2.70-2.85 (m, 3H), 2.20 (s, 6H), 1.89-2.03 (m, 4H), 1.75-1.90 (m, 1H), 1.70-1.75 (m, 1H), 1.60-1.70 (m, 1H), 1.48-1.59 (m, 3H), 1.15-1.28 (m, 3H), 0.95-1.13 (m, 6H). $^{31}$P NMR (162 MHz, DMSO-d6) δ ppm 53.11. $^{19}$F NMR (377 MHz, DMSO-d6) δ ppm −122.00. LC-MS: m/z 917.3 $(M+H)^{+}$.

Example 15: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(2,2-dimethylmorpholino)-1H-indol-1-yl)-2-methylcyclopropyl)-1,2,4-oxadiazol-5(4H)-one (single diastereomer 2, Compound 115a)

115a

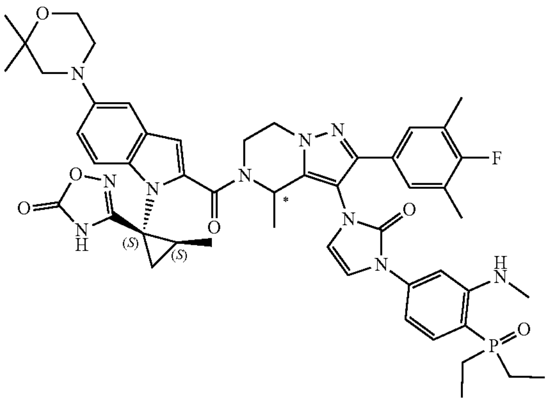

single diastereomer 2

(Compound 115a) was synthesized following the route in Example 9, using 5-(2,2-dimethylmorpholino)-1-((1S,2S)-2-methyl-1-(5-oxo-4,5-dihydro-1,2,4-oxadiazol-3-yl)cyclopropyl)-1H-indole-2-carboxylic acid in step C.

$^{1}$H NMR (400 MHz, DMSO-$d_6$, 80° C.) δ ppm 11.50 (br.s, 1H), 7.35 (d, J=9.6 Hz, 1H), 7.20-7.25 (m, 4H), 7.05-7.15 (m, 2H), 6.94 (s, 2H), 6.85 (s, 1H), 6.72 (d, J=3.2 Hz, 1H), 5.68 (br.s, 1H), 4.60 (d, J=14.8 Hz, 1H), 4.28-4.42 (m, 3H), 3.85-4.00 (m, 1H), 3.75-3.82 (m, 2H), 2.98-3.05 (m, 2H), 2.87 (s, 2H), 2.68-2.76 (m, 3H), 2.18 (s, 6H), 1.85-1.98 (m, 4H), 1.75-1.85 (m, 1H), 1.69 (t, J=6.4 Hz, 1H), 1.55-1.65 (m, 1H), 1.42-1.52 (m, 3H), 1.25-1.30 (m, 6H), 1.10-1.20 (m, 3H), 0.96-1.08 (m, 6H). $^{31}$P NMR (162 MHz, DMSO-d6) δ ppm 52.92. $^{19}$F NMR (377 MHz, DMSO-d6) δ ppm −122.03. LC-MS: m/z 473.2 $(M/2+H)^{+}$.

Example 16: 3-((1S,2S)-1-(2-(3-(3-(4-(dimethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-5-(tetrahydro-2H-pyran-4-yl)-1H-indol-1-yl)-2-methylcyclopropyl)-1,2,4-oxadiazol-5(4H)-one (single diastereomer 2, Compound 118a)

118a

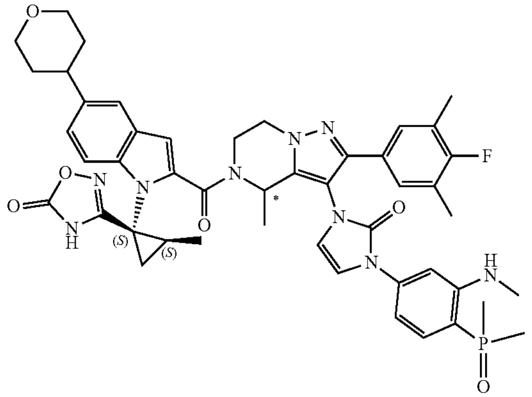

single diastereomer 2

(Compound 118a) was synthesized following the route in Example 9, using (4-bromo-2-(methylamino)phenyl)dimethylphosphine oxide in step A and 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid in step C.

$^1$H NMR (400 MHz, DMSO-$d_6$, 80° C.) δ ppm 11.52 (br.s, 1H), 7.50 (s, 1H), 7.40 (d, J=8.4 Hz, 1H), 7.19-7.31 (m, 5H), 6.85-7.00 (m, 3H), 6.70-6.75 (m, 1H), 5.70 (br.s, 1H), 4.62 (d, J=15.6 Hz, 1H), 4.30-4.40 (m, 2H), 3.80-4.00 (m, 3H), 3.40-3.52 (m, 2H), 2.80-2.92 (m, 1H), 2.74 (br.s, 3H), 2.18 (s, 6H), 1.56-1.78 (m, 14H), 1.43-1.55 (m, 3H), 1.05-1.25 (m, 3H). $^{31}$P NMR (162 MHz, DMSO-d6) δ ppm 42.49. $^{19}$F NMR (377 MHz, DMSO-d6) δ ppm −122.04. LC-MS: m/z 444.8 (M/2+H)$^+$.

Example 17: 3-(1-(2-(2-(4-fluoro-3,5-dimethylphenyl)-4-methyl-3-(3-(1-methyl-1H-indazol-5-yl)-2-oxo-2,3-dihydro-1H-imidazol-1-yl)-4,5,6,7-tetrahydropyrazolo[1,5-a]pyrazine-5-carbonyl)-5-(tetrahydro-2H-pyran-4-yl)-1H-indol-1-yl)cyclopropyl)-1,2,4-oxadiazol-5(4H)-one (Compound 103)

103

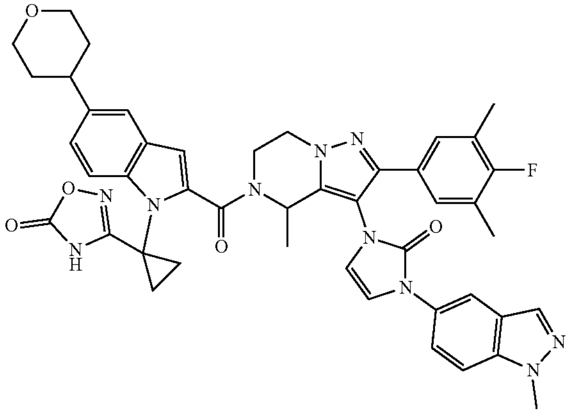

Compound 103 was synthesized following the route of Example 2, using tert-butyl 2-(4-fluoro-3,5-dimethylphenyl)-4-methyl-3-(2-oxo-2,3-dihydro-1H-imidazol-1-yl)-6,7-dihydropyrazolo[1,5-a]pyrazine-5(4H)-carboxylate in step A.

$^1$H NMR (400 MHz, DMSO-$d_6$, 80° C.) δ ppm 11.81 (br.s, 1H), 8.04 (s, 1H), 7.96 (s, 1H), 7.58-7.70 (m, 2H), 7.48-7.50 (m, 2H), 7.20-7.26 (m, 3H), 7.15 (d, J=3.2 Hz, 1H), 6.87 (s, 1H), 6.69 (d, J=2.8 Hz, 1H), 5.73 (br.s, 1H), 4.62 (d, J=12.8 Hz, 1H), 4.26-4.40 (m, 2H), 4.05 (s, 3H), 3.96 (d, J=11.2 Hz, 2H), 3.80-3.92 (m, 1H), 3.42-3.50 (m, 2H), 2.83-2.90 (m, 1H), 2.19 (s, 6H), 1.64-1.82 (m, 7H), 1.50-2.01 (m, 1H), 1.45 (d, J=6.8 Hz, 3H). $^{19}$F NMR (377 MHz, DMSO-d6) δ ppm −122.14. LC-MS: m/z 823.5 (M+H)$^+$.

Example A: cAMP Assays

Activation of GLP-1 receptor is known to stimulate cyclic AMP (cAMP) production in cells which indicates primary coupling to the $G_{\alpha s}$ subunit of the G protein heterotrimeric complex. Evidence suggests signaling through $G_{\alpha s}$ induced cAMP stimulation elicits the desired pharmacological response regarding insulin release from pancreatic β-cells.

To optimize functional activity directed toward $G_{\alpha s}$ coupling, a HEK293/CRE-Luc cell line developed by HDB stably expressing the GLP-1 Receptor was used. 200× concentration of compound working solutions were prepared (Agilent Technologies Bravo) with ½ log serial dilution in 384-well Echo LDV plate (Labcyte, Cat #LP-0200). 50 nL/well 200×concentration of compound working solutions were moved to 384-well white low volume plate (Greiner, Cat #784075) using Labcyte ECHO550. 1×10$^5$ cells/mL HEK293/GLP1R/CRE-LUC(HD Biosciences) cell suspensions prepared with assay buffer[DPBS containing 0.5 mM IBMX (Sigma, Cat #15879) and 0.1% BSA (GENVIEW, Cat #FA016-100g)], 10 uL cell suspensions were added to each well of previous generated assay plate which already contains 50nl compound at 200× concentration using ThermoFisher Multidrop Combi (1000 cells/well). Seal the plate and incubate at 37° C. with 5% CO2 for 30 min.

After incubation the cAMP assay signal was generated using cAMP dynamic 2 Kit (Cisbio). 5 μL cAMP-d2 working solution was added to each well, followed with 5 μL Anti-cAMP antibody-cryptate working solution added to each well using ThermoFisher Multidrop Combi. Incubate at room temperature for 1 hour protected from light. Read the fluorescence at 665 and 615 nm with Reader PerkinElmer EnVision.

% Activity=100%×(mean RLU of test sample−mean RLU of vehicle control)/(mean RLU of MAX control−mean RLU of vehicle control))

Table 1 shows the biological activity of compounds in GLP-1R agonist cAMP stimulation assay ($EC_{50}$) [nM]

TABLE 1 shows the biological activity of compounds in GLP-1R cAMP stimulation assay ($EC_{50}$) [nM]

| Compound No. | GLP1R cAMP Stimulation DR: $EC_{50}$ (nM) [Species: Human, Assay Cell Line: HDB] | GLP1R cAMP Stimulation DR: $pEC_{50}$ (M) [Species: Human, Assay Cell Line: HDB] |
|---|---|---|
| 101 | 3.41 | 8.48 |
| 102 | 3300 | 5.66 |
| 105a | 1.86 | 8.73 |
| 106a | 113 | 6.95 |
| 103 | 0.29 | 9.5 |
| 104 | 0.18 | 9.7 |
| 108a | 0.10 | 10.0 |
| 109a | 0.18 | 9.7 |
| 110a | 0.13 | 9.9 |
| 111a | 0.042 | 10.4 |
| 112a | 42 | 7.4 |
| 113a | 0.17 | 9.8 |
| 114a | 0.068 | 10.2 |
| 115a | 0.15 | 9.8 |
| 116a | 0.42 | 9.4 |
| 117a | 0.07 | 10.2 |
| 118a | 0.03 | 10.5 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I):

Formula (I)

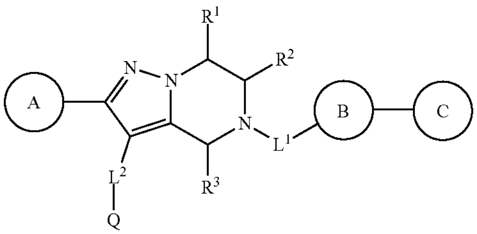

or a pharmaceutically acceptable salt or solvate thereof, wherein:

Ring A is $C_{6-10}$ aryl, $C_{5-10}$ cycloalkyl, 5-10 membered heterocyclyl, or 5-10 membered heteroaryl, each of which is optionally substituted with from 1-5 substituents each independently selected from the group consisting of: halo, $C_{1-6}$ alkyl, $C_{1-6}$ haloalkyl, and $C_{1-6}$ alkoxy;

$R^1$, $R^2$ and $R^3$ are each independently selected from the group consisting of H and $C_{1-6}$ alkyl which is optionally substituted with from 1-6 substituents each independently selected from the group consisting of halo, —OH, and $C_{1-6}$ alkoxy;

$L^1$ is selected from the group consisting of: —C(=O)—, —$CH_2$—, —CH($C_{1-6}$ alkyl)-, and —S(=O)$_2$;

Ring B is selected from the group consisting of:

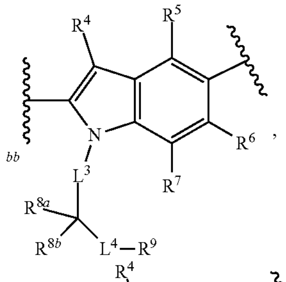
,
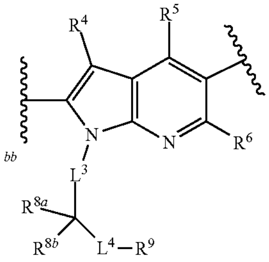
,
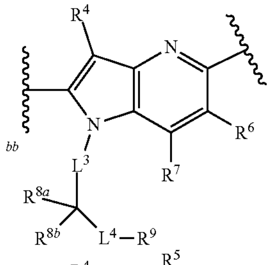
, and
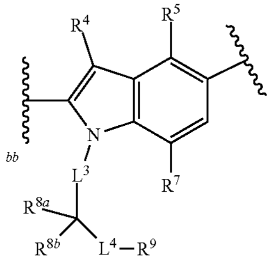
, wherein bb represents point of attachment to $L^1$;

$R^4$, $R^5$, $R^6$, and $R^7$ are independently selected from the group consisting of: H, halo, and $C_{1-6}$ alkyl;

$L^3$ is a bond or $C_{1-3}$ alkylene;

$L^4$ is a bond or $C_{1-5}$ alkylene;

$R^{8a}$ and $R^{8b}$ are independently selected from the group consisting of: H and $C_{1-6}$ alkyl optionally substituted with one or more substituents independently selected from the group consisting of: halo and $C_{3-15}$ cycloalkyl; or $R^{8a}$ and $R^{8b}$ taken together with the carbon atom to which each is attached forms a $C_{3-15}$ cycloalkyl ring which is optionally substituted with from 1-3 independently selected $C_{1-6}$ alkyl, wherein the $C_{1-6}$ alkyl is optionally substituted with from 1-6 independently selected $R^f$, $R^9$ is selected from the group consisting of: C(=O)OH, C(=O)(O$C_{1-6}$ alkyl), C(=O)N$R^{9a}R^{9b}$, (IX-1), (IX-2), (IX-3), and (IX-4):

(IX-1)

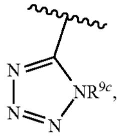

(IX-2)

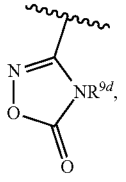

(IX-3)

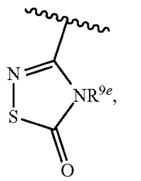

(IX-4)

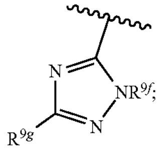

$R^{9a}$ is H or $C_{1-6}$ alkyl;

$R^{9b}$ is H, $C_{1-6}$ alkyl, C(=O)($C_{1-6}$ alkyl), S(O)$_{0-2}$($C_{1-6}$ alkyl), or cyano;

$R^{9c}$, $R^{9d}$, $R^{9e}$, $R^{9f}$, and $R^{9g}$ are each independently selected from the group consisting of: H; $C_{1-6}$ alkyl optionally substituted with from 1-6 independently selected halo and $C_{1-6}$ alkoxy; and C(=O)($C_{1-6}$ alkyl);

Ring C is selected from the group consisting of 3-12 membered heterocyclyl; $C_{3-10}$ cycloalkyl; and 5-10 membered heteroaryl, each of which is optionally substituted with from 1-3 $R^{Ca}$;

each $R^{Ca}$ is independently selected from the group consisting of: halo, $C_{1-6}$ alkyl, $C_{1-6}$ haloalkyl, $C_{1-6}$ alkoxy, and $NR^cR^d$;

or a pair of $R^{Ca}$ on the same or different ring atoms, taken together with the ring atom(s) to which each is attached, forms a carbocyclic ring including from 3-8 ring atoms;

$L^2$ is selected from the group consisting of:

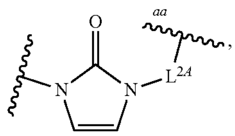, 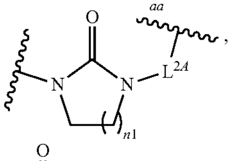,

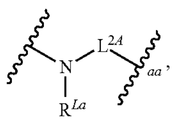, 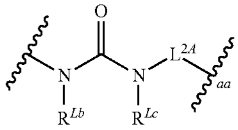, and

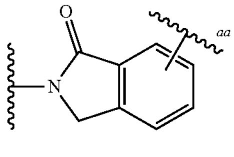, wherein aa represents the point of attachment to Q;

n1 is an integer from 1-3;

$L^{2A}$ is a bond or $C_{1-10}$ alkylene;

$R^{La}$ is selected from the group consisting of H, $C_{1-6}$ alkyl, and C(=O)($C_{1-6}$ alkyl);

each of $R^{Lb}$ and $R^{Lc}$ is independently selected from the group consisting of: H and $C_{1-6}$ alkyl;

Q is selected from the group consisting of: $C_{1-10}$ alkyl; $C_{3-15}$ cycloalkyl; 3-12 membered heterocyclyl; 5-10 membered heteroaryl; and $C_{6-10}$ aryl, each of which is optionally substituted with from 1-6 independently selected $R^Q$;

each $R^Q$ is independently selected from the group consisting of:

(a) halo;

(b) cyano;

(c) OH or oxo;

(d) —$NR^cR^d$, (e) —C(=O)$NR^cR^d$ or —$S(O)_2NR^cR^d$, (f) —$S(=O)_{0-2}R^e$;

(g) $C_{1-6}$ alkyl optionally substituted with from 1-6 independently selected $R^f$, (h) $C_{1-6}$ alkoxy optionally substituted with from 1-6 independently selected $R^f$;

(i) 3-12 membered heterocyclyl optionally substituted with from 1-6 independently selected $R^g$;

(j) $C_{6-10}$ aryl optionally substituted with from 1-6 independently selected $R^g$;

(k) 5-10 membered heteroaryl optionally substituted with from 1-6 independently selected $R^g$;

(l) $C_{3-8}$ cycloalkyl optionally substituted with from 1-6 independently selected $R^g$;

(m) —P(=O)$R^aR^b$, and (n) —$(CR^hR^h)_{q1}$—$S(O)_2$-$L^e$-$R^e$, wherein q1 is 1, 2, or 3;

$R^a$ and $R^b$ are independently selected from the group consisting of $C_{1-6}$ alkyl which is optionally substituted with from 1-6 substituents each independently selected from the group consisting of $C_{1-6}$ alkoxy, $C_{3-6}$ cycloalkyl, and halo; $C_{3-6}$ cycloalkyl optionally substituted with from 1-3 substituents each independently selected from the group consisting of $C_{1-3}$ alkyl and halo; and $C_{6-10}$ aryl optionally substituted with from 1-3 independently selected $C_{1-3}$ alkyl; or $R^a$ and $R^b$ taken together with the phosphorous atom to which each is attached forms a ring including from 5-8 ring atoms, wherein from 0-2 ring atoms (in addition to the phosphorous attached to $R^a$ and $R^b$) are heteroatoms each independently selected from the group consisting of: O, S, and N, wherein the ring is optionally substituted with from 1-3 independently selected $C_{1-6}$ alkyl;

each $R^c$ and $R^d$ are independently selected from the group consisting of: H, $C_{1-6}$ alkyl, $C_{3-6}$ cycloalkyl, C(=O)($C_{1-6}$ alkyl), C(=O)($C_{3-6}$ cycloalkyl), C(=O)O($C_{1-6}$ alkyl), $S(O)_{1-2}$($C_{1-6}$ alkyl), and $S(O)_{1-2}$($C_{3-6}$ cycloalkyl), wherein the $C_{1-6}$ alkyl, C(=O)($C_{1-6}$ alkyl), C(=O)($C_{3-6}$ cycloalkyl), C(=O)O($C_{1-6}$ alkyl), $S(O)_{1-2}$($C_{1-6}$ alkyl), and $S(O)_{1-2}$($C_{3-6}$ cycloalkyl) are each optionally substituted with from 1-6 substituents independently selected from the group consisting of: —OH, halo, and $C_{1-6}$ alkoxy;

$R^e$ is H, or $R^e$ is selected from the group consisting of: $C_{1-6}$ alkyl, $C_{1-6}$ haloalkyl, $C_{1-6}$ alkoxy, $C_{1-6}$ haloalkoxy, $C_{3-6}$ cycloalkyl, and 3-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $NH_2$, NH($C_{1-3}$ alkyl), N($C_{1-3}$ alkyl$)_2$, $C_{1-3}$ alkoxy, and $C_{1-3}$ haloalkoxy;

$L^e$ is a bond, $NR^c$, or O;

each $R^f$ is independently selected from the group consisting of halo, —OH, $NR^cR^d$, $C_{1-6}$ alkoxy, $C_{1-6}$ haloalkoxy, and 3-12 membered heterocyclyl which is optionally substituted with from 1-4 substituents each independently selected from the group consisting of —OH, $C_{1-6}$ alkyl, and 3-12 membered heterocyclyl;

each $R^g$ is independently selected from the group consisting of: $C_{1-6}$ alkyl, $C_{1-6}$ haloalkyl, $C_{1-6}$ alkoxy, $C_{1-6}$ haloalkoxy, $NR^cR^d$, cyano, halo, $C_{3-6}$ cycloalkyl, and 3 to 12 membered heterocyclyl optionally substituted with one or more substituents each independently selected from the group consisting of $C_{1-6}$ alkyl and C(=O)$C_{1-6}$ alkyl; and each occurrence of $R^h$ is independently selected from the group consisting of: H, $C_{1-6}$ alkyl, $C_{1-6}$ haloalkyl, $C_{3-6}$ cycloalkyl, and halo; or a pair of $R^h$ on the same or different carbon atom(s), taken together with the carbon atom(s) connecting them forms $C_{3-6}$ cycloalkyl or 4-8 membered heterocyclyl, each of which is optionally substituted with from 1-3 substituents each independently selected from the group consisting of: halo, cyano, $C_{1-3}$ alkyl, $C_{1-3}$ haloalkyl, —OH, $C_{1-3}$ alkoxy, and $C_{1-3}$ haloalkoxy.

2. The compound of claim 1, wherein Q is

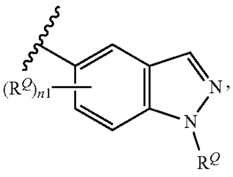, wherein n1 is 0 or 1.

3. The compound of claim 1, wherein Q is phenyl optionally substituted with from 1-6 independently selected $R^Q$.

4. The compound of claim 1, wherein the $R^Q$ para to $L^2$ is —P(=O)$R^aR^b$.

5. The compound of claim 4, wherein $R^a$ and $R^b$ are independently selected $C_{1-6}$ alkyl optionally substituted with from 1-6 substituents each independently selected from the group consisting of $C_{1-6}$ alkoxy, $C_{3-6}$ cycloalkyl, and halo.

6. The compound of claim 1, wherein $R^1$, $R^2$, and $R^3$ are H.

7. The compound of claim 1, wherein $R^1$ and $R^2$ are H; and $R^3$ is $C_{1-6}$ alkyl.

8. The compound of claim 7, wherein $R^3$ is methyl.

9. The compound of claim 1, wherein $L^2$ is

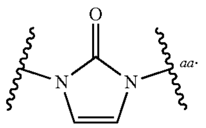 [SMILES: *n1ccn(*)c1=O]

10. The compound of claim 1, wherein Ring A is

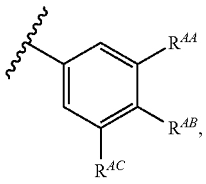

wherein $R^{AA}$, $R^{AB}$, and $R^{AC}$ are independently halo or $C_{1-6}$ alkyl.

11. The compound of claim 1, wherein $L^1$ is C(=O).

12. The compound of claim 1, wherein Ring B is

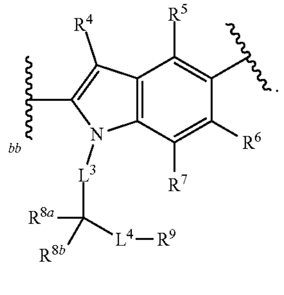

13. The compound of claim 12, wherein $R^4$, $R^5$, and $R^6$ are each H.

14. The compound of claim 12, wherein $R^7$ is H.

15. The compound of claim 1, wherein both of $L^3$ and $L^4$ are bonds.

16. The compound of claim 1, wherein $R^{8a}$ and $R^{8b}$ taken together with the carbon atom to which each is attached forms a $C_{3-5}$ cycloalkyl ring which is optionally substituted with from 1-2 independently selected $C_{1-6}$ alkyl, wherein the $C_{1-6}$ alkyl is optionally substituted with from 1-3 independently selected $R^f$.

17. The compound of claim 1, wherein $R^{8a}$ and $R^{8b}$ taken together with the carbon atom to which each is attached forms:

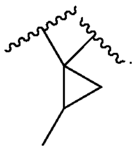 [SMILES: *C1(*)CC1C]

18. The compound of claim 1, wherein $R^9$ is (IX-2)

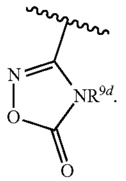

19. The compound of claim 1, wherein Ring C is tetrahydropyranyl which is optionally substituted with from 1-3 independently $R^{Ca}$.

20. A compound selected from the group consisting of the compounds in Table C1 or Table C2,

TABLE C1

| Compound No. | Structure |
|---|---|
| 101 | 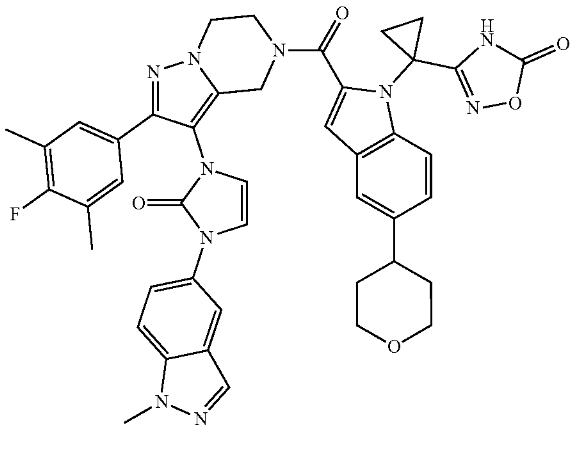 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CC2)CC3)cc(C)c1F] |

TABLE C1-continued
| Compound No. | Structure |
| --- | --- |
| 102 | 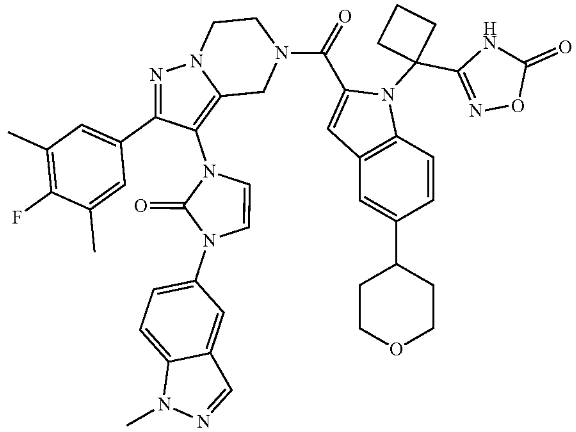 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CCC2)CC3)cc(C)c1F] |
| 103 | 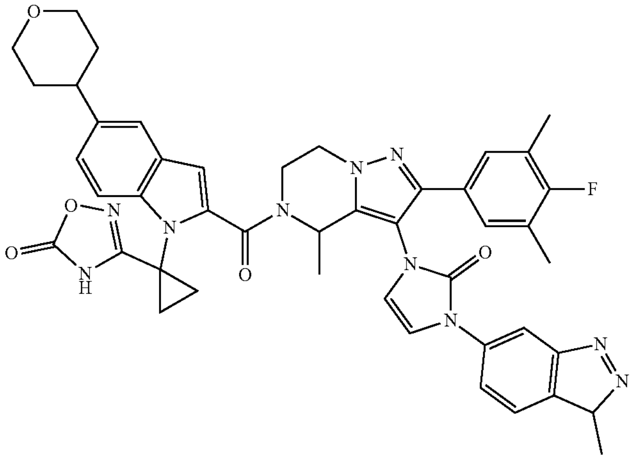 [SMILES: Cc1cc(-c2nn3c(c2-n2ccn(-c4ccc5c(c4)N=NC5C)c2=O)C(C)N(C(=O)c2cc4cc(C5CCOCC5)ccc4n2C2(c4noc(=O)[nH]4)CC2)CC3)cc(C)c1F] |
| 104 | 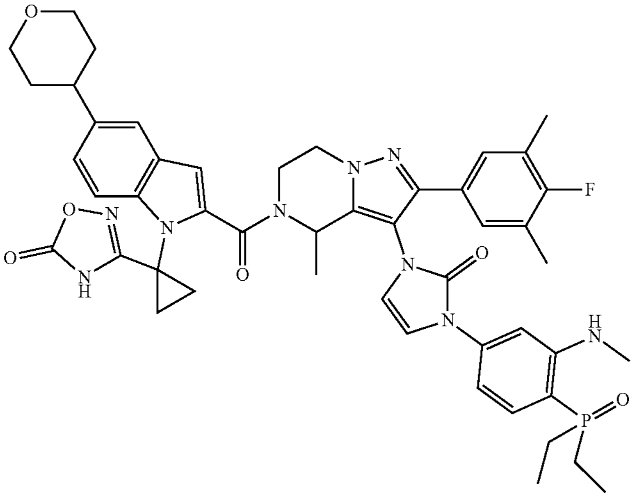 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3)CC4)c2=O)cc1NC] |

TABLE C1-continued
| Compound No. | Structure |
|---|---|
| 105 | 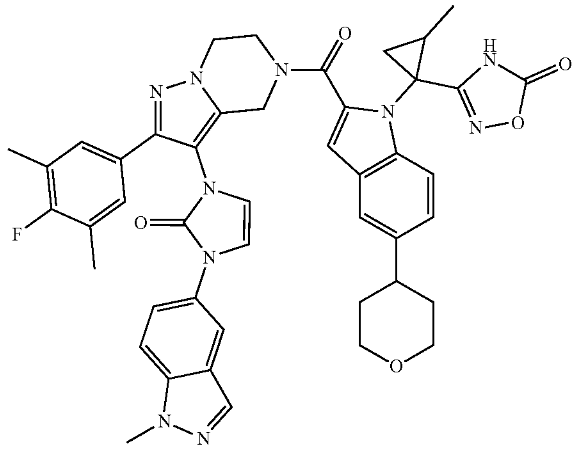 [SMILES: Cc1cc(-c2nn3c(c2-n2ccn(-c4ccc5c(cnn5C)c4)c2=O)CN(C(=O)c2cc4cc(C5CCOCC5)ccc4n2C2(c4noc(=O)[nH]4)CC2C)CC3)cc(C)c1F] |
| 106 | 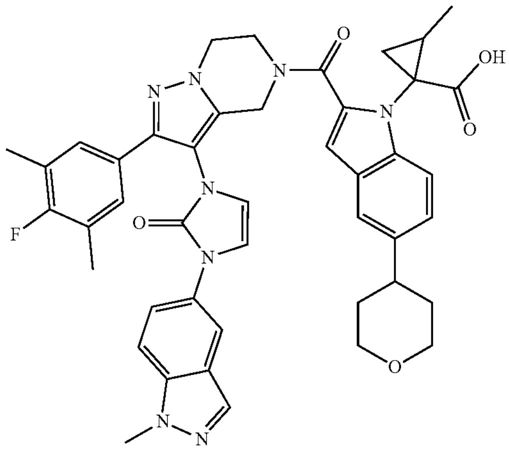 [SMILES: Cc1cc(-c2nn3c(c2-n2ccn(-c4ccc5c(cnn5C)c4)c2=O)CN(C(=O)c2cc4cc(C5CCOCC5)ccc4n2C2(C(=O)O)CC2C)CC3)cc(C)c1F] |
| 107 | 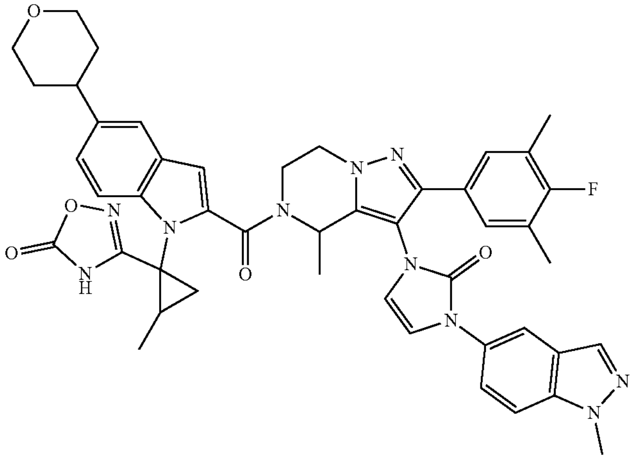 [SMILES: Cc1cc(-c2nn3c(c2-n2ccn(-c4ccc5c(cnn5C)c4)c2=O)C(C)N(C(=O)c2cc4cc(C5CCOCC5)ccc4n2C2(c4noc(=O)[nH]4)CC2C)CC3)cc(C)c1F] |

TABLE C1-continued
| Compound No. | Structure |
| --- | --- |
| 108 | 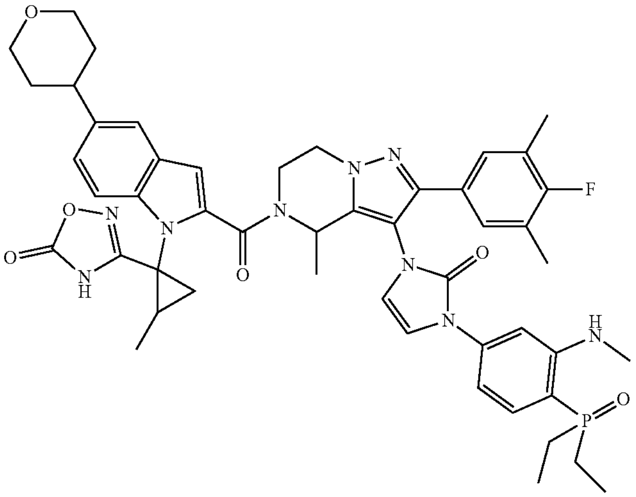 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)cc1NC] |
| 109/110 | 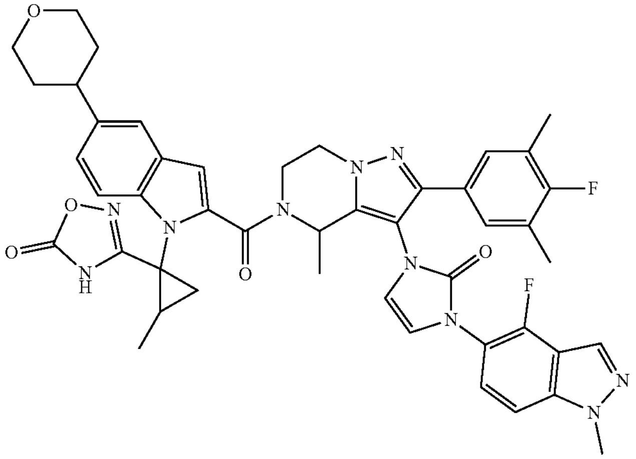 |
| 111/112 | 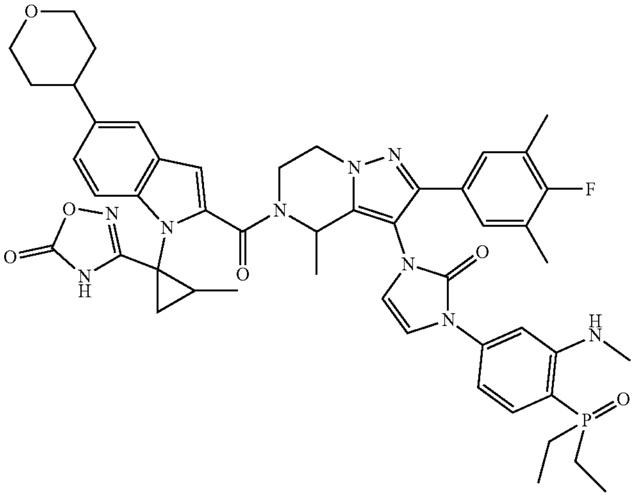 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)cc1NC] |

TABLE C1-continued
| Compound No. | Structure |
| --- | --- |
| 113 | 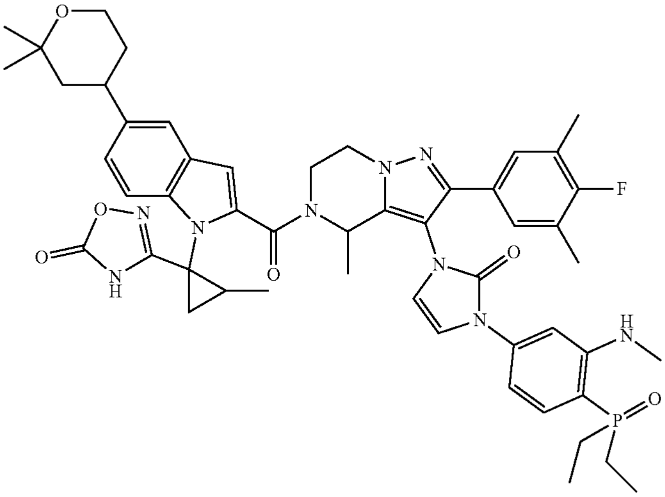 |
| 114 | 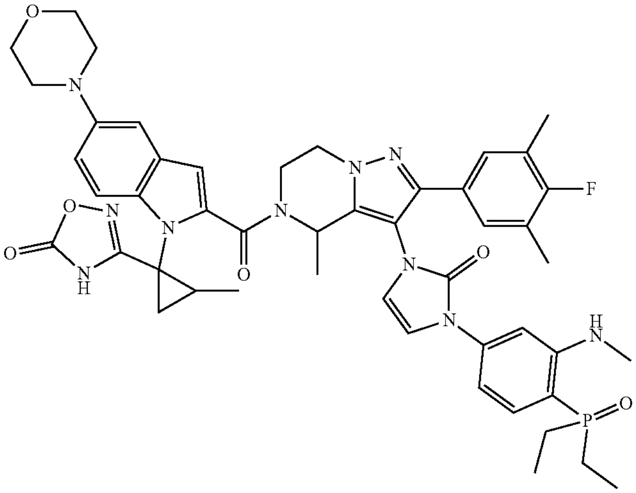 |
| 115 | 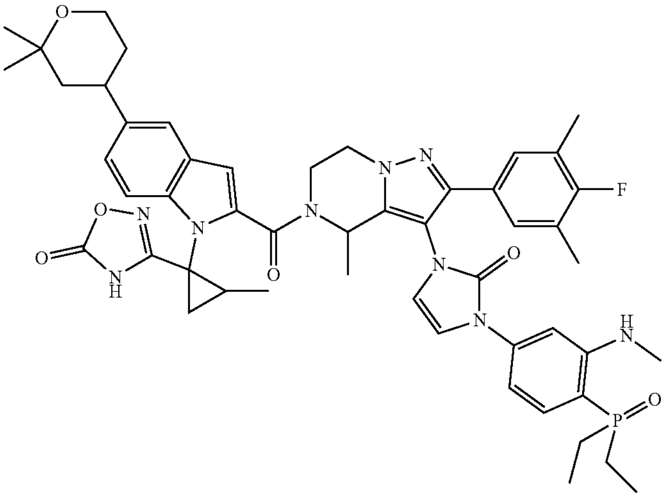 |

TABLE C1-continued
| Compound No. | Structure |
|---|---|
| 116 | 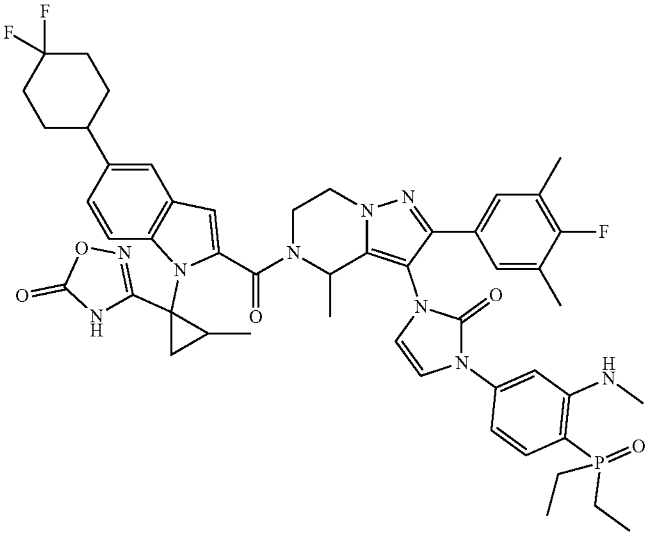 [SMILES: CCP(=O)(CC)c1ccc(-n2ccn(-c3c(-c4cc(C)c(F)c(C)c4)nn4c3C(C)N(C(=O)c3cc5cc(C6CCC(F)(F)CC6)ccc5n3C3(c5noc(=O)[nH]5)CC3C)CC4)c2=O)cc1NC] |
| 117 | 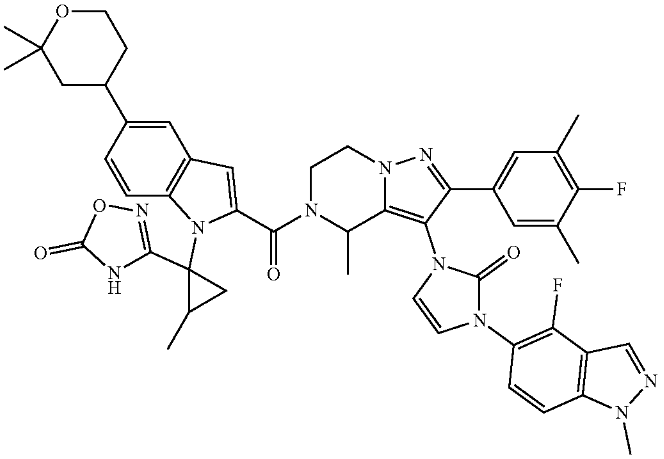 [SMILES: Cc1cc(-c2nn3c(c2-n2ccn(-c4ccc5c(cnn5C)c4F)c2=O)C(C)N(C(=O)c2cc4cc(C5CCOC(C)(C)C5)ccc4n2C2(c4noc(=O)[nH]4)CC2C)CC3)cc(C)c1F] |
| 118 | 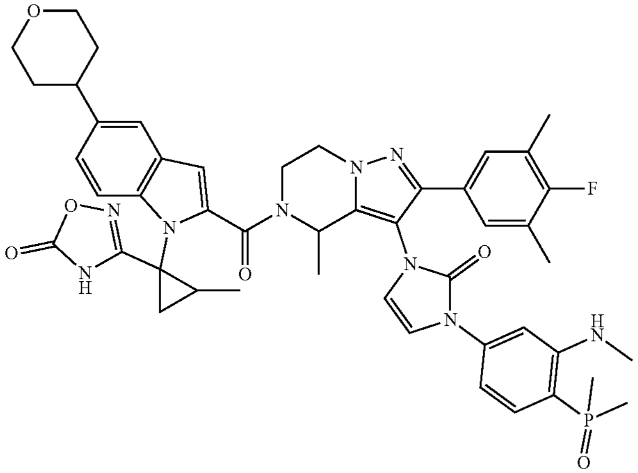 [SMILES: CNc1cc(-n2ccn(-c3c(-c4cc(C)c(F)c(C)c4)nn4c3C(C)N(C(=O)c3cc5cc(C6CCOCC6)ccc5n3C3(c5noc(=O)[nH]5)CC3C)CC4)c2=O)ccc1P(C)(C)=O] |

TABLE C2
| Compound No. | Structure |
|---|---|
| 105a | 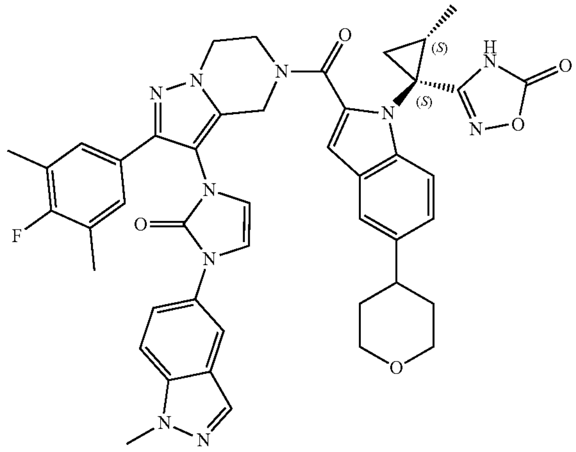 |
| 106a | 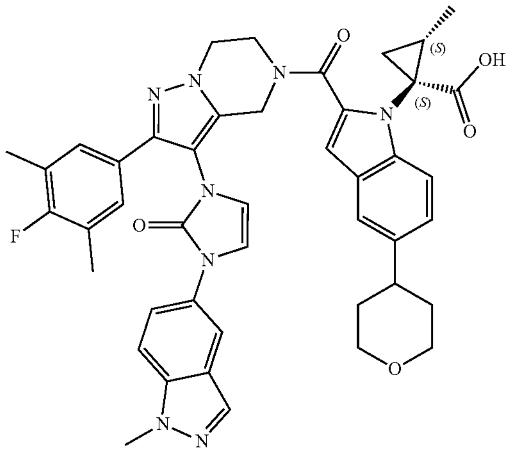 |
| 107a | 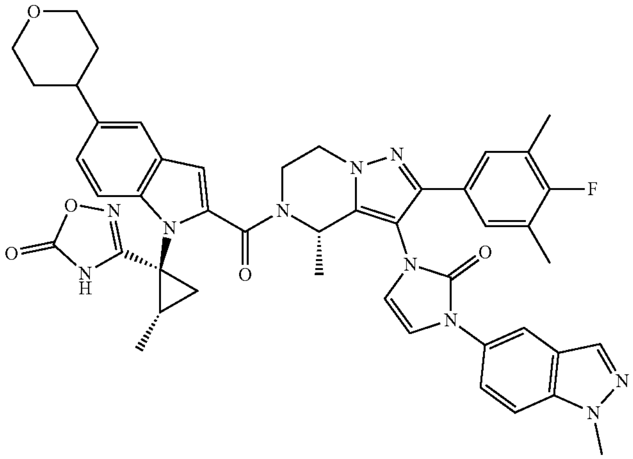 [SMILES: Cc1cc(-c2nn3c(c2-n2ccn(-c4ccc5c(cnn5C)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE C2-continued
| Compound No. | Structure |
|---|---|
| 108a | 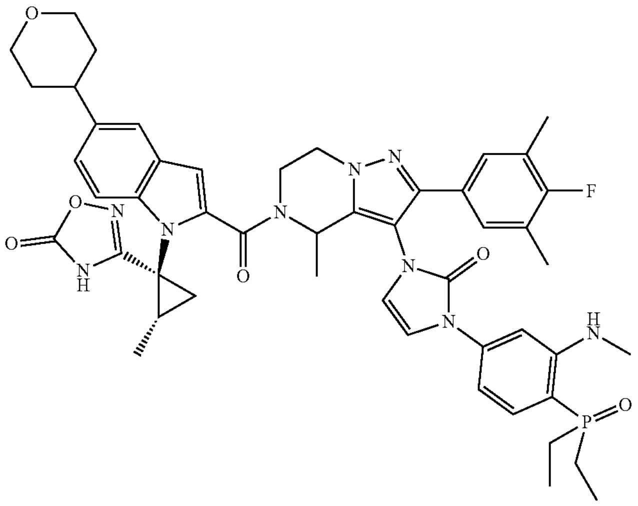 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3[C@@]3(c5noc(=O)[nH]5)C[C@@H]3C)CC4)c2=O)cc1NC] |
| 109a | 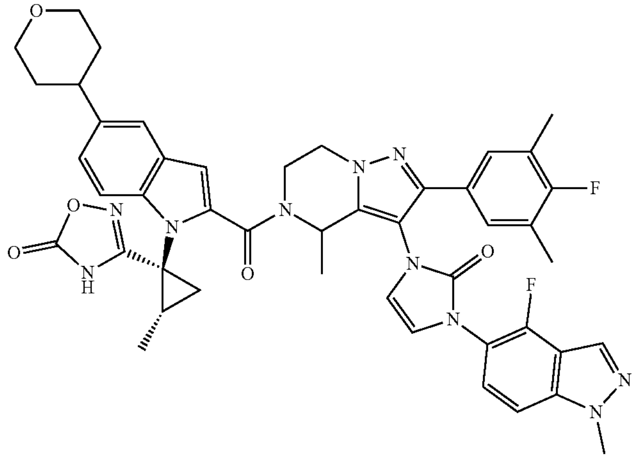 [SMILES: Cc1cc(-c2nn3c(c2-n2ccn(-c4ccc5c(cnn5C)c4F)c2=O)C(C)N(C(=O)c2cc4cc(C5CCOCC5)ccc4n2[C@@]2(c4noc(=O)[nH]4)C[C@@H]2C)CC3)cc(C)c1F] |
| 110a | 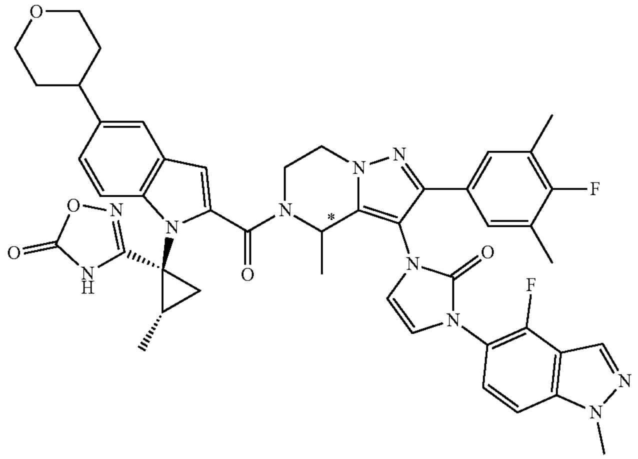 [SMILES: Cc1cc(-c2nn3c(c2-n2ccn(-c4ccc5c(cnn5C)c4F)c2=O)C(C)N(C(=O)c2cc4cc(C5CCOCC5)ccc4n2[C@@]2(c4noc(=O)[nH]4)C[C@@H]2C)CC3)cc(C)c1F]<br>single diastereomer 2 |

TABLE C2-continued
| Compound No. | Structure |
|---|---|
| 111a | 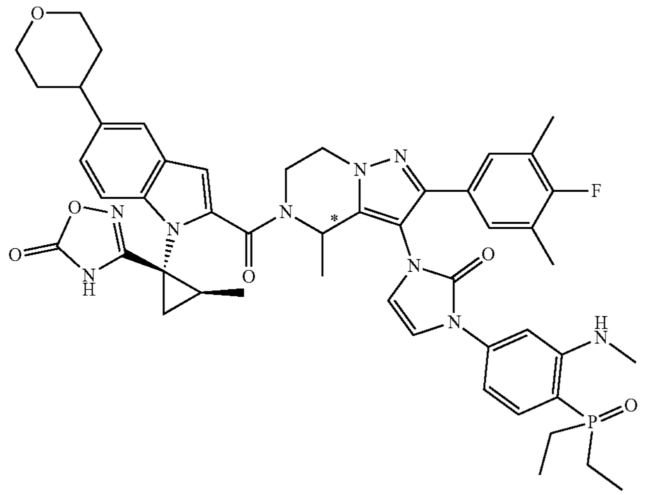 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3[C@@]3(c5noc(=O)[nH]5)C[C@@H]3C)CC4)c2=O)cc1NC] single diastereomer 2 |
| 112a | 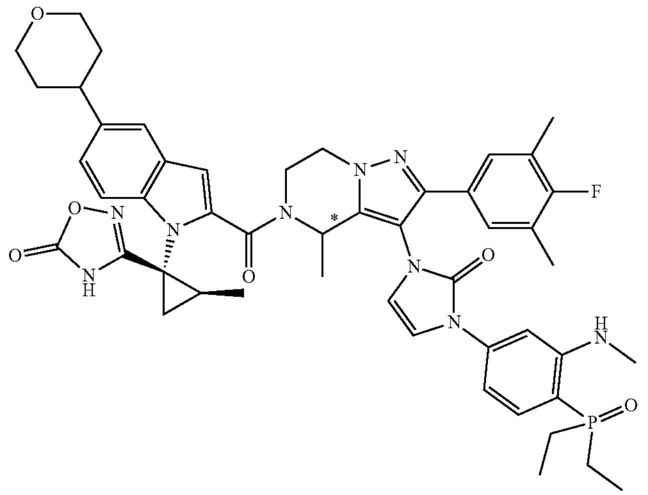 [SMILES: CCP(=O)(CC)c1ccc(-n2ccn(-c3c(-c4cc(C)c(F)c(C)c4)nn4c3C(C)N(C(=O)c3cc5cc(C6CCOCC6)ccc5n3[C@@]3(c5noc(=O)[nH]5)C[C@@H]3C)CC4)c2=O)cc1NC] single diastereomer 1 |
| 113a | 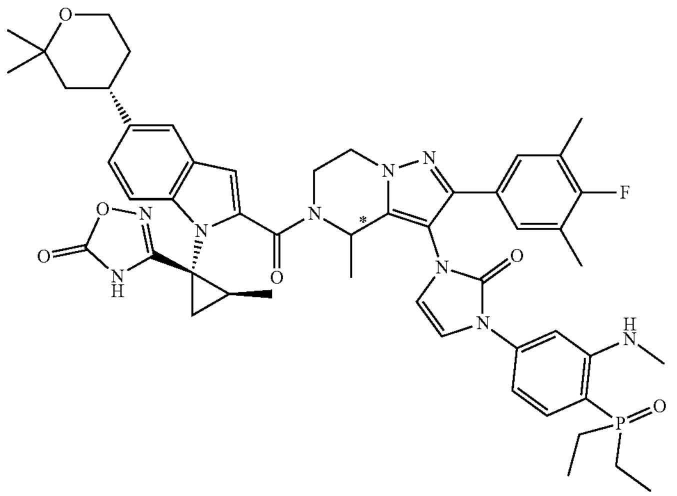 single diastereomer 2 |

TABLE C2-continued
| Compound No. | Structure |
| --- | --- |
| 114a | 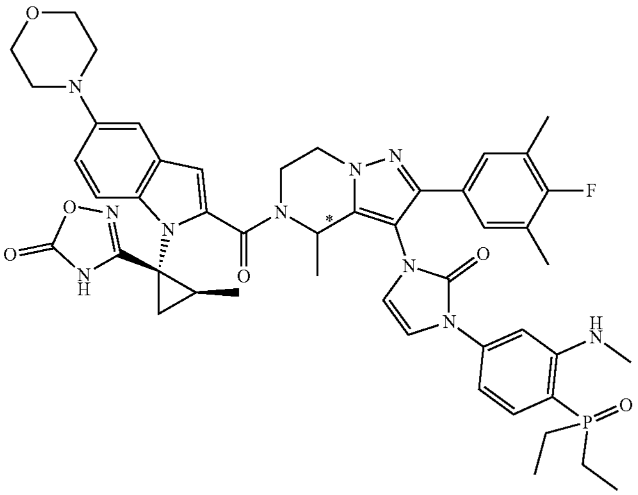 single diastereomer 2 |
| 115a | 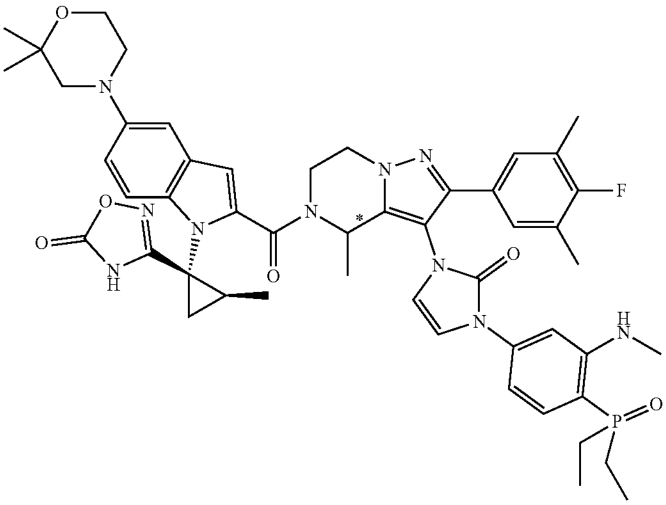 single diastereomer 2 |

TABLE C2-continued
| Compound No. | Structure |
| --- | --- |
| 116a | 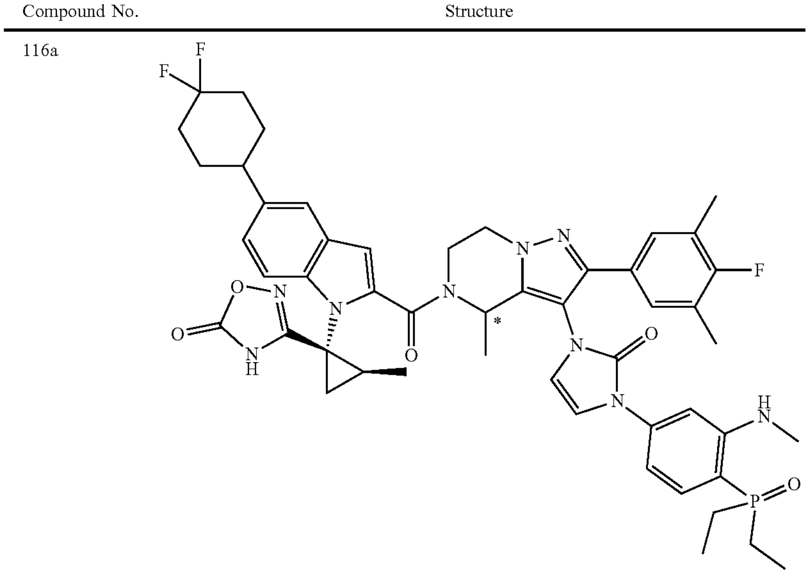 single diastereomer 2 |
| 117a | 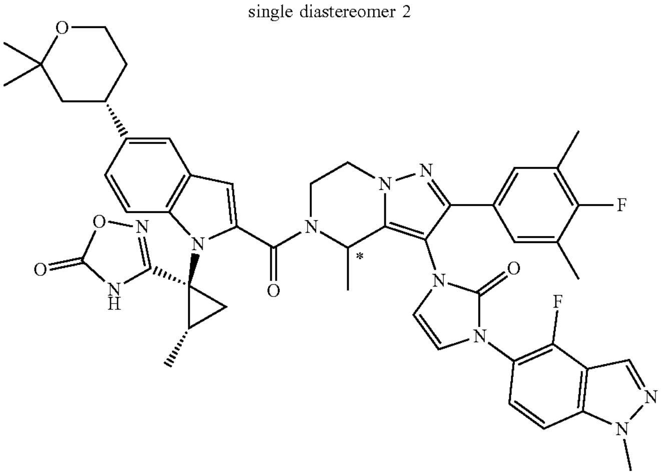 single diastereomer 2 |
| 118a | 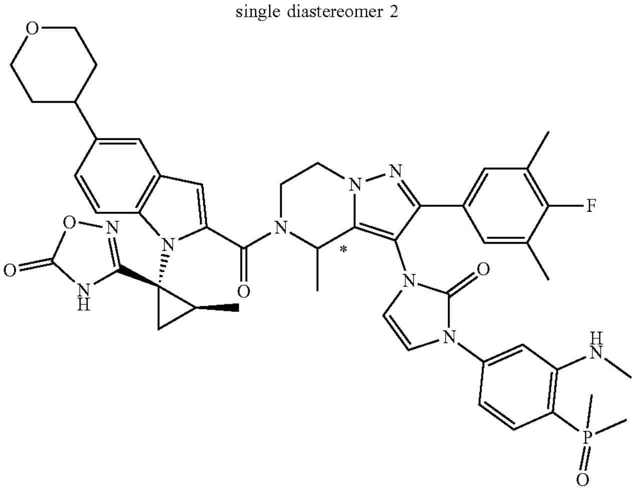 single diastereomer 2 |
or a pharmaceutically acceptable salt or solvate thereof.

21. A pharmaceutical composition comprising a compound of claim 1, or a pharmaceutically acceptable salt or solvate thereof, and a pharmaceutically acceptable excipient.

22. A method for treating a GLP-1 associated disease, disorder, or condition, the method comprising administering to a patient in need thereof an effective amount of a compound as claimed in claim 1, or a pharmaceutically acceptable salt or solvate thereof, or a pharmaceutical composition according to claim 21, wherein the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof.

23. The method of claim 22, wherein the disease, disorder, or condition is type 2 diabetes mellitus.

24. The method of claim 22, wherein the disease, disorder, or condition is obesity.

* * * * *